United States Patent
Wang et al.

(10) Patent No.: US 8,778,563 B2
(45) Date of Patent: Jul. 15, 2014

(54) NANODEVICES FOR GENERATING POWER FROM MOLECULES AND BATTERYLESS SENSING

(75) Inventors: Yinmin Wang, Tracy, CA (US); Xianying Wang, Shanghai (CN); Alex V. Hamza, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 0 days.

(21) Appl. No.: 13/451,796

(22) Filed: Apr. 20, 2012

(65) Prior Publication Data

US 2012/0237853 A1 Sep. 20, 2012

Related U.S. Application Data

(63) Continuation of application No. PCT/US2010/053827, filed on Oct. 22, 2010.

(60) Provisional application No. 61/253,890, filed on Oct. 22, 2009, provisional application No. 61/255,571, filed on Oct. 28, 2009, provisional application No. 61/286,858, filed on Dec. 16, 2009.

(51) Int. Cl.
 *H01M 14/00* (2006.01)

(52) U.S. Cl.
 USPC .............................. 429/523; 257/9

(58) Field of Classification Search
 USPC ............... 429/523; 257/9; 977/742, 755, 762
 See application file for complete search history.

(56) References Cited

U.S. PATENT DOCUMENTS

| | | | |
|---|---|---|---|
| 6,906,003 B2 | 6/2005 | Struthers et al. | |
| 7,045,240 B2 | 5/2006 | Yamada et al. | |
| 7,582,992 B2 | 9/2009 | Pinkerton et al. | |
| 2005/0118494 A1 | 6/2005 | Choi | |
| 2009/0075157 A1* | 3/2009 | Pak et al. | 429/44 |

OTHER PUBLICATIONS

Korean Intellectual Property Office (KIPO), International Search Report and Written Opinion issued on Jul. 13, 2011, including claims searched, related PCT International Application No. PCT/US2010/053827, pp. 1-17.

* cited by examiner

*Primary Examiner* — Mark F Huff
*Assistant Examiner* — Monique Wills
(74) *Attorney, Agent, or Firm* — O'Banion & Ritchey LLP

(57) ABSTRACT

A nanoconverter or nanosensor is disclosed capable of directly generating electricity through physisorption interactions with molecules that are dipole containing organic species in a molecule interaction zone. High surface-to-volume ratio semiconductor nanowires or nanotubes (such as ZnO, silicon, carbon, etc.) are grown either aligned or randomly-aligned on a substrate. Epoxy or other nonconductive polymers are used to seal portions of the nanowires or nanotubes to create molecule noninteraction zones. By correlating certain molecule species to voltages generated, a nanosensor may quickly identify which species is detected. Nanoconverters in a series parallel arrangement may be constructed in planar, stacked, or rolled arrays to supply power to nano- and micro-devices without use of external batteries. In some cases breath, from human or other life forms, contain sufficient molecules to power a nanoconverter. A membrane permeable to certain molecules around the molecule interaction zone increases specific molecule nanosensor selectivity response.

7 Claims, 37 Drawing Sheets

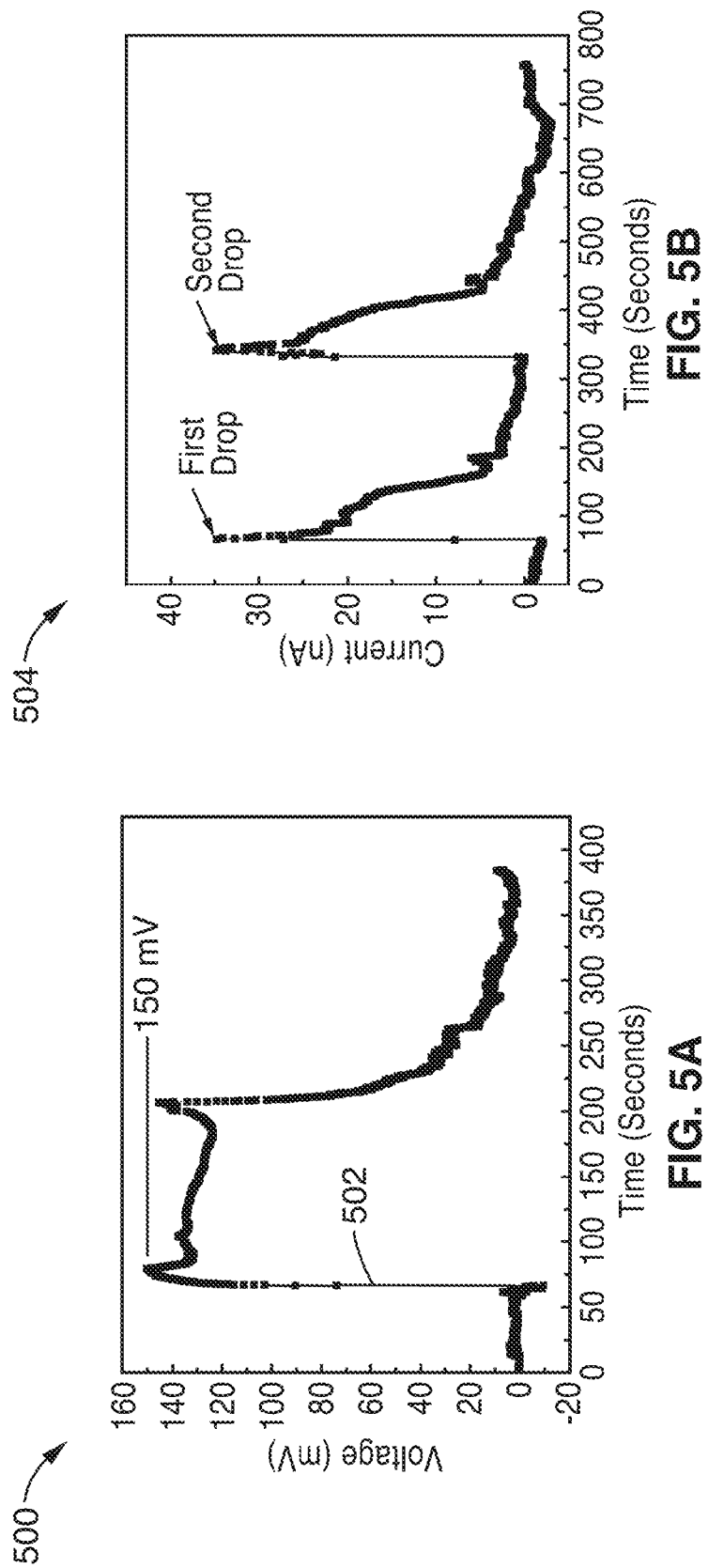

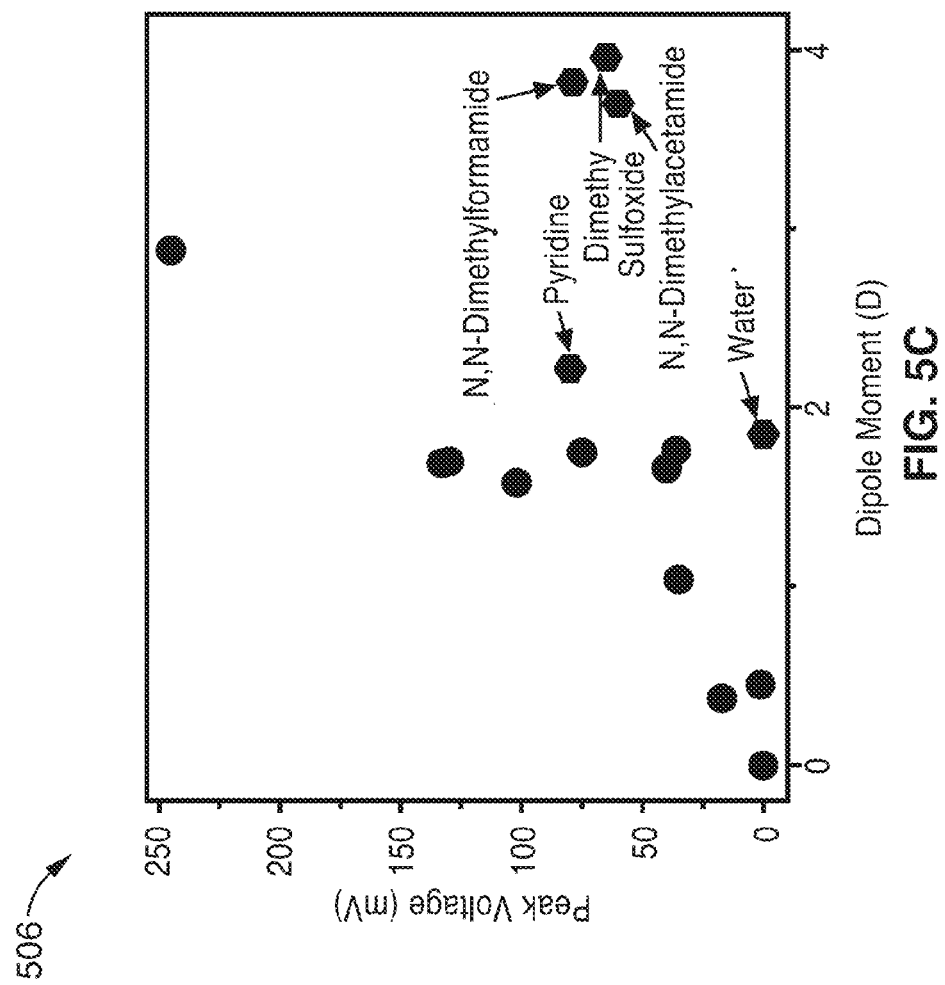

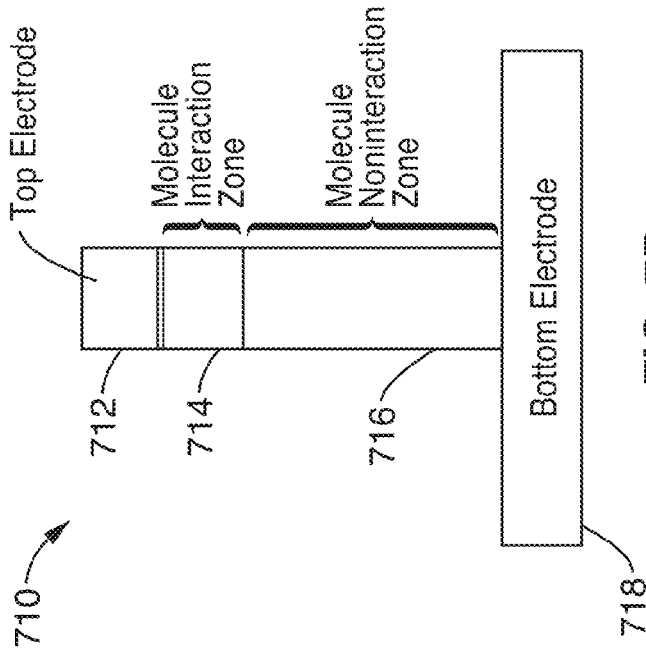
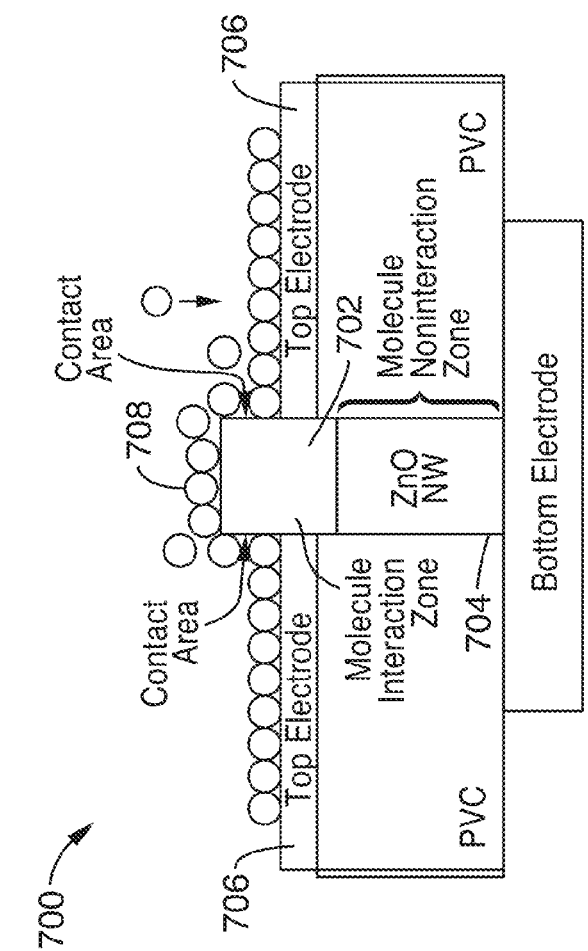

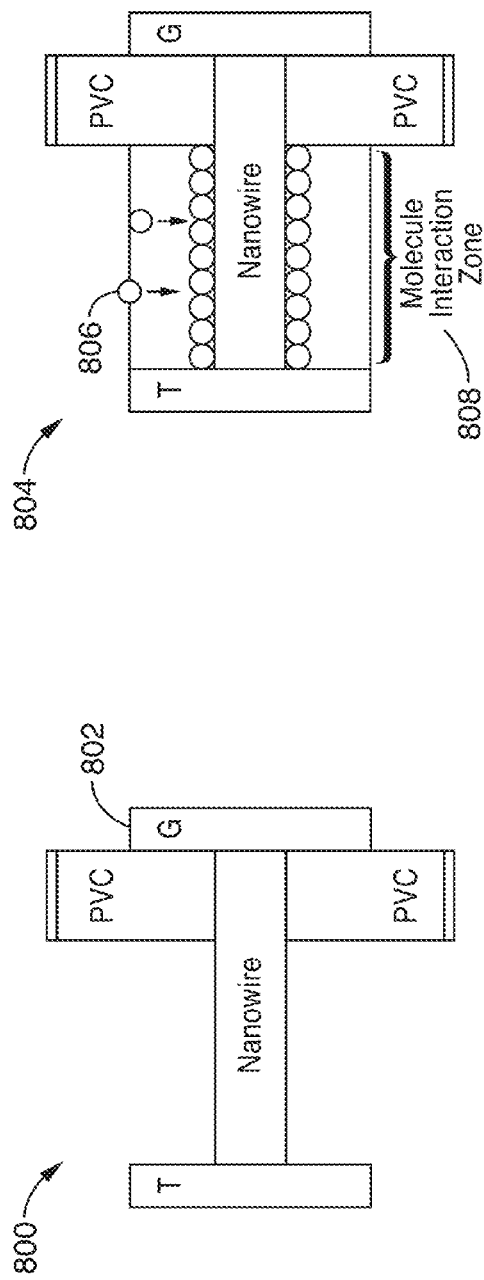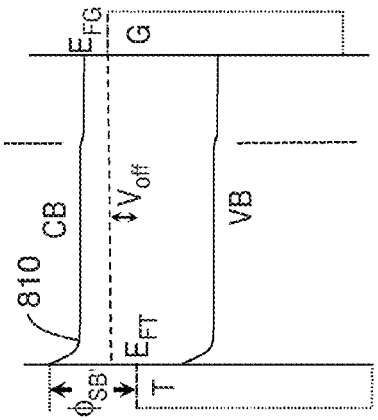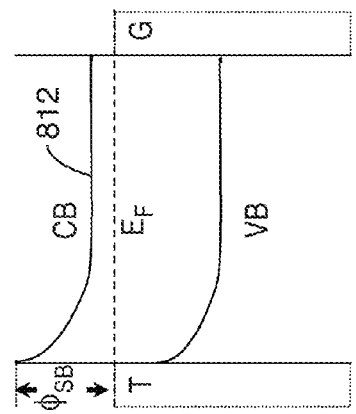
FIG. 8A
FIG. 8B
FIG. 8C
FIG. 8D

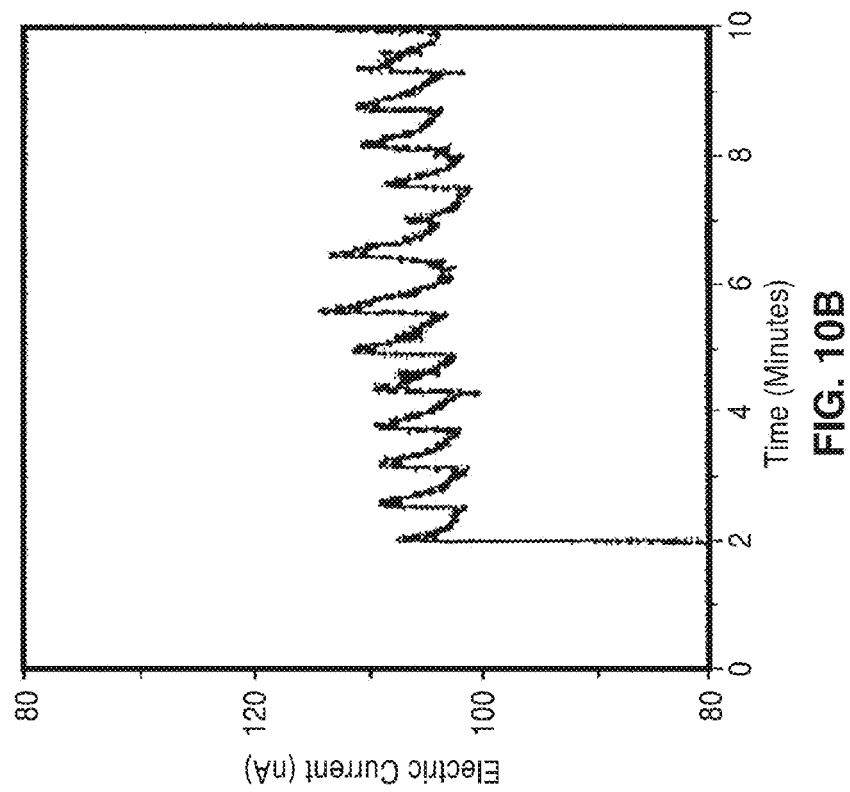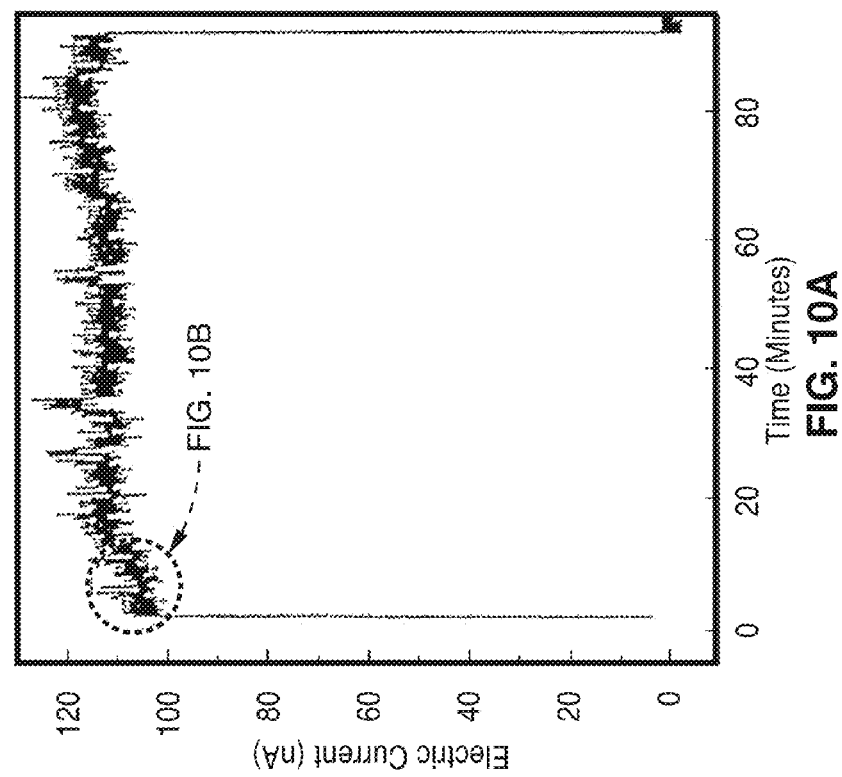

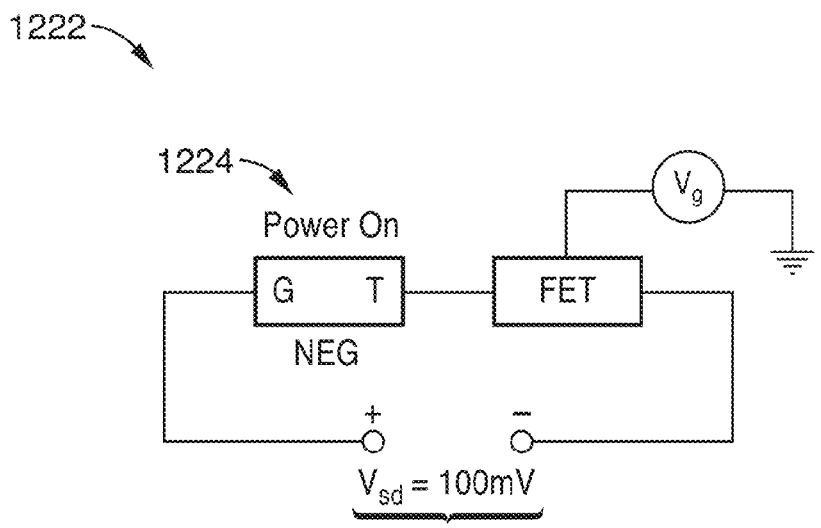
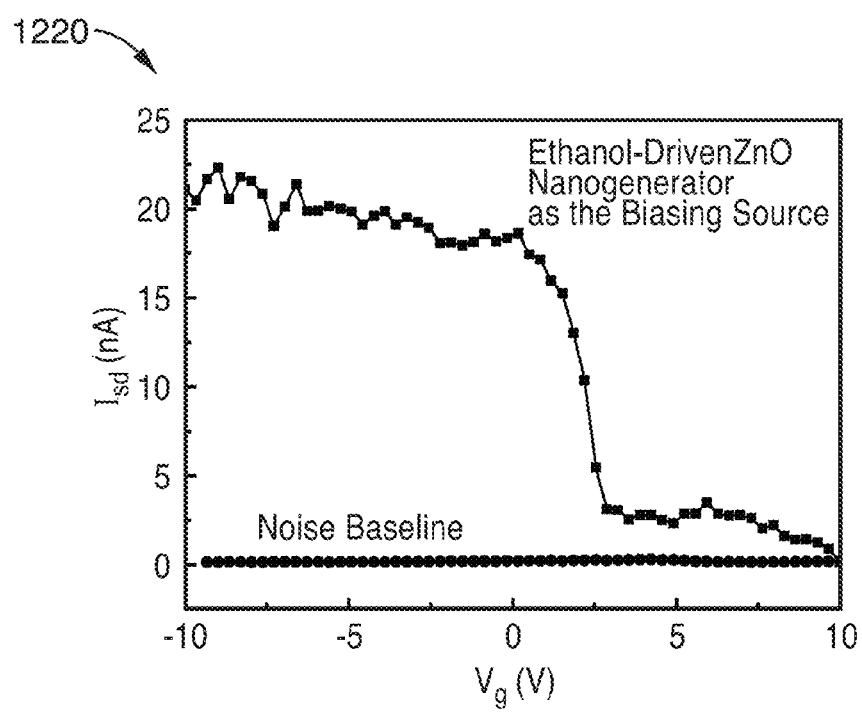
FIG. 12D

NANODEVICES FOR GENERATING POWER FROM MOLECULES AND BATTERYLESS SENSING

CROSS-REFERENCE TO RELATED APPLICATIONS

This application is a 35 U.S.C. §111(a) continuation of PCT international application number PCT/US2010/053827 filed on Oct. 22, 2010, incorporated herein by reference in its entirety, which is a nonprovisional of U.S. provisional patent application Ser. No. 61/253,890 filed on Oct. 22, 2009, incorporated herein by reference in its entirety, and a nonprovisional of U.S. provisional patent application Ser. No. 61/255,571 filed on Oct. 28, 2009, incorporated herein by reference in its entirety, and a nonprovisional of U.S. provisional patent application Ser. No. 61/286,858 filed on Dec. 16, 2009, incorporated herein by reference in its entirety. Priority is claimed to each of the foregoing applications.

The above-referenced PCT international application was published as PCT International Publication No. WO 2011/050307 on Apr. 28, 2011 and republished on Sep. 9, 2011, and is incorporated herein by reference in its entirety.

STATEMENT REGARDING FEDERALLY SPONSORED RESEARCH OR DEVELOPMENT

This invention was made with Government support under Contract No DE-AC52-07NA27344 awarded by the US Department of Energy (DOE). The Government has certain rights in this invention.

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to nanoscale power generation, more particularly to nanodevice power generation from or nanosensor detection of molecules, and still more particularly to power generation through physisorption of molecules onto nanostructures.

2. Description of Related Art

In a complex environment, there exists a variety of energy sources, such as mechanical energy, solar energy, and thermal energy. In additional to these "traditional" energy sources, there are other types of energy sources. For example, molecules contain chemical energy. When interacting with certain types of materials, molecules can either be decomposed (through catalytic activities) or directly interact with semiconductor surfaces through charge-transfer or dipole-interactions. Both processes provide a new mechanism to generate potentials inside materials and thus electric-current and voltage.

The present invention provides a system for generating electric current through molecule-semiconductor interactions. By monitoring the electric potentials generated through the molecule-semiconductor surface interaction, applicants have determined that one can also detect the types of molecules for sensing purposes. Prior to this invention, there was no early work related to this subject. Therefore this is a conceptually new approach.

The treatise, *Introduction to Nanotechnology*, by Charles P. Poole, Jr., and Frank J. Owens. John Wiley &. Sons, 2003, states: "Nanotechnology is based on the recognition that particles less than the size of 100 nanometers (a nanometer is a billionth of a meter) impart to nanostructures built from them new properties and behavior. This happens because particles which are smaller than the characteristic lengths associated with particular phenomena often display new chemistry and physics, leading to new behavior which depends on the size. So, for example, the electronic structure, conductivity, reactivity, melting temperature, and mechanical properties have all been observed to change when particles become smaller than a critical size."

BRIEF SUMMARY OF THE INVENTION

Features and advantages of the present invention will become apparent from the following description. Applicants are providing this description, which includes drawings and examples of specific embodiments, to give a broad representation of the invention. Various changes and modifications within the spirit and scope of the invention will become apparent to those skilled in the art from this description and by practice of the invention. The scope of the invention is not intended to be limited to the particular forms disclosed and the invention covers all modifications, equivalents, and alternatives falling within the spirit and scope of the invention as defined by the claims.

The present invention provides a nanoconverter system that will directly generate electricity through interactions with molecules. High surface-to-volume ratio semiconductor nanowires or nanotubes (such as ZnO, silicon, carbon nanotubes, etc.) are grown either aligned (typically substantially vertically, without limitation) or randomly-aligned on a substrate. Epoxy or other types of insulators are used to seal tips, portions, or certain percents of the nanowires or nanotubes to form a nanoconverter. The subsequent exposure of portions of the nanowires or nanotubes to molecules allows the nanoconverter to generate an electric current. The molecules contain chemical energy. When interacting with certain types of materials, these molecules can either be decomposed (through catalytic activities) or directly interact with semiconductor surfaces through charge-transfer or dipole-interactions. The nanoconverter system can also be used for sensing purpose without any external power supplies (i.e., batteryless sensing).

An aspect of the invention is a nanoconverter, comprising: one or more nanostructures; and means for generating power from the nanostructures. The means for generating power may comprise a molecule interaction zone wherein the nanostructures are capable of interaction with molecules. The means for generating power may also comprise a molecule noninteraction zone wherein the nanostructures are incapable of interaction with molecules.

In the nanoconverter above, the nanostructures may be selected from a group of nanocomponents comprising: a nanotube, a nanowire, a nanosheet, and a nanoribbon. The nanostructures may be selected from a group of nanostructures comprising: a ZnO nanowire, a silicon nanowire, a carbon nanotube, and a semiconductor nanostructure. The nanostructures may be either vertically- or randomly-aligned.

In the nanoconverter above, the means for generating power may comprise an interaction of the nanostructures with a molecule in a molecule interaction zone. The molecule may originate from a source consisting of an exhalation, an air sample, and a liquid sample. Such exhalation may originate from a group of exhalants consisting of: human breath, non-human animal breath, bacterial outgas, and plant outgas.

An array of one or more the nanoconverters may be combines so as to form a nanoconverter array, arranged to generate a specified current and voltage output when supplied with a molecule. The preferred molecules are dipole containing organic molecules. Specifically, the dipole containing organic molecule may be selected from a group consisting of: alcohols, amines, amides, carboxylic acids, esters, furans, pyridines, aldehydes, ketones, sulfoxides, carbohydrates, and similar and/or equivalent dipole containing species. More specifically, the molecule may be selected from a group of molecules consisting of: methanol, ethanol, toluene, trichoromethane, n-butanol, 1-propanol, 1-octanol, tetrahydrofuran, pyridine, acetone, N,N-dimethyacetamide, N,N-dimethyformamide, dimethyl sulfoxide, glucose, and their combinations.

The nanoconverter array described above may operate as a nanosensor to detect molecules by generation of a voltage. Further, a membrane permeable to the molecule may surround the molecule interaction zone.

In the nanoconverter array above, the means for generating power may generate output power for one or more of a group of devices consisting of: a cell phone, a smart phone, a glucose monitor, a pacemaker, a therapeutic or diagnostic device, a drug delivery device, an insulin pump, a left ventricular assist device, a cardioverter defibrillator, an artificial muscle device, a cochlear implant, a batteryless device, a powered nanomachine, an artificial vision device, and similar or equivalent devices.

In the nanoconverter array above, the means for generating power may generate output power for an insulin control system, comprising: a nanosensor glucose monitor that produces a voltage proportional to a glucose molecule concentration; a controller that senses the nanosensor glucose monitor voltage; and an insulin pump controlled by the controller whereby insulin is disseminated when the nanosensor glucose monitor voltage is exceeded.

In the nanoconverter above, the molecule noninteraction zone may be permeated by a sealant selected from the group of sealants consisting of: epoxy, poly(vinyl chloride-co-vinyl-co-2-hydroxypropyl acrylate) (PVC) polymer, and equivalent materials.

The nanoconverter above may comprise: an electrode that electrically connects to the nanostructure in the molecule interaction zone; and an electrode that electrically connects to the nanostructure in the molecule noninteraction zone.

Another aspect of the invention is a nanoconverter apparatus, comprising: a nanostructure with first and second ends; an electrode electrically connected to the nanostructure proximal to a molecule interaction zone at the first end of the nanostructure; a sealant matrix that surrounds at least a portion of the nanostructure, wherein the surrounded portion of the nanostructure forms a molecule noninteraction zone; an electrode electrically connected to the nanostructure proximal to the molecule noninteraction zone at the second end of the nanostructure; wherein the nanostructure generates a voltage and a current when the molecule interaction zone interacts with a molecule. Within the molecule noninteraction zone the nanostructures are incapable of interaction with molecules.

In the nanoconverter above, the nanostructure may be selected from a group of nanocomponents comprising: a carbon nanotube, a nanowire, a nanosheet, or a nanoribbon. Additionally, the nanostructure may be selected from a group of nanostructures comprising: a ZnO nanowire, a silicon nanowire, a carbon nanotube. The nanostructure may be an element of a vertically- or randomly-aligned forest of nanostructures.

In the nanoconverter above, the nanostructure may generate the voltage and the current through physisorption of the molecule onto the nanostructure. The molecule may originate from a source consisting of an exhalation, an air sample, and a liquid sample. The exhalation may originate from a group of exhalants consisting of: human breath, non-human animal breath, bacterial outgas, and plant outgas.

A nanoconverter array may be constructed, comprising: an array of one or more nanoconverters described above; wherein the nanoconverters are arranged to generate a specified current output and voltage output when supplied with a molecule.

In the nanoconverter array above, the preferred molecules are dipole containing organic molecules. Specifically, the dipole containing organic molecule may be selected from a group consisting of: alcohols, amines, amides, carboxylic acids, esters, furans, pyridines, aldehydes, ketones, sulfoxides, carbohydrates, and similar and/or equivalent dipole containing species. More specifically, the molecule is a dipole containing organic species that may be selected from a group of molecules consisting of: methanol, ethanol, toluene, trichoromethane, n-butanol, 1-propanol, 1-octanol, tetrahydrofuran, pyridine, acetone, N,N-dimethyacetamide, N,N-dimethyformamide, dimethyl sulfoxide, glucose, and their combinations. The molecule may be substantially polar.

The nanoconverter array above may operate as a nanosensor to detect molecules by voltage generation. Further, the nanoconverter array may, comprise a permeable membrane to the molecule that surrounds the molecule interaction zone; wherein the permeable membrane preferentially allows a specific molecule.

In the nanoconverter array above, the nanostructure generated voltage and current outputs may supply power for one or more of the group of devices consisting of: a cell phone, a smart phone, a glucose monitor, a pacemaker, a therapeutic or diagnostic device, a drug delivery device, an insulin pump, a left ventricular assist device, a cardioverter defibrillator, an artificial muscle device, a cochlear implant, a batteryless device, a powered nanomachine, an artificial vision device, and similar or equivalent devices.

In the nanoconverter array above, the nanostructure generated voltage and current outputs may supply power for an insulin control system, comprising:
a nanosensor glucose monitor that produces a voltage proportional to a glucose molecule concentration; a controller that senses the nanosensor glucose monitor voltage; and an insulin pump controlled by the controller whereby insulin is disseminated when the nanosensor glucose monitor voltage is exceeded.

In the nanoconverter above, the molecule noninteraction zone sealant may be permeated by a sealant selected from the group of sealants consisting of: epoxy, poly(vinyl chlorideco-vinyl-co-2-hydroxypropyl acrylate) (PVC) polymer, silicon carbide, and similar or equivalent materials A still further aspect of the invention is a method of constructing a nanoconverter, comprising: providing a substrate; growing one or more nanostructures on the substrate; permeating the nanostructures with a sealant to form a molecule noninteraction zone around the nanostructures; selectively etching the molecule noninteraction zone around the nanostructures to form a molecule interaction zone; and electrically connecting the nanostructures at two ends, wherein the two end have disposed between them the molecule interaction zone and the molecule noninteraction zone. The method of constructing the nanoconverter may further comprise exposing the molecule interaction zone to one or more molecules, thereby generating electrical power. Within the molecule noninteraction zone the nanostructures may be substantially incapable of interaction with molecules.

In the method of constructing the nanoconverter above, the nanostructures may be selected from a group of nanocomponents comprising: a nanotube, a nanowire, a nanosheet, and a nanoribbon.

In the method of constructing the nanoconverter above, the nanostructures may be selected from a group of nanostructures comprising: a ZnO nanowire, a silicon nanowire, a carbon nanotube, and a semiconductor nanostructure. The nanostructures may be vertically- or randomly-aligned.

The nanostructures may generate the electrical power through physisorption of the molecules onto the nanostructures. The molecules may originate from a source consisting of an exhalation, an air sample, and a liquid sample. The exhalation may originate from a group of exhalants consisting of: human breath, non-human animal breath, bacterial outgas, and plant outgas.

A nanoconverter array may be constructed by interconnecting an array of one or more nanoconverters constructed above; wherein the nanoconverters are arranged to generate a specified current output and voltage output when supplied with a molecule.

Again, the preferred molecules are dipole containing organic molecules. Specifically, the dipole containing organic molecule may be selected from a group consisting of: alcohols, amines, amides, carboxylic acids, esters, furans, pyridines, aldehydes, ketones, sulfoxides, carbohydrates, and similar and/or equivalent dipole containing species. For example, the molecules are dipole containing organic species that may be selected from a group of molecules consisting of: methanol, ethanol, toluene, trichoromethane, n-butanol, 1-propanol, 1-octanol, tetrahydrofuran, pyridine, acetone, N,N-dimethyacetamide, N,N-dimethyformamide, dimethyl sulfoxide, glucose, and their combinations. The molecules may be substantially polar.

The nanoconverter array described above may operate as a nanosensor to detect the molecules by generating a voltage. Further, a membrane permeable to the molecule may surround the molecule interaction zone; wherein the membrane preferentially allows permeation of a specific molecule.

The nanoconverter array described above may generate power output to one or more of the group of devices consisting of: a cell phone, a smart phone, a glucose monitor, a pacemaker, a therapeutic or diagnostic device, a drug delivery device, an insulin pump, a left ventricular assist device, a cardioverter defibrillator, an artificial muscle device, a cochlear implant, a batteryless device, a powered nanomachine, an artificial vision device, and similar or equivalent devices.

The nanoconverter array described above may generate power output to power to an insulin control system, comprising: a nanosensor glucose monitor that produces a voltage proportional to a glucose molecule concentration; a controller that senses the nanosensor glucose monitor voltage; and an insulin pump controlled by the controller whereby insulin is disseminated when the nanosensor glucose monitor voltage is exceeded.

The method of constructing the nanoconverter above may use as the molecule noninteraction zone sealant a permeation of a sealant selected from the group of sealants consisting of: epoxy, poly(vinyl chloride-co-vinyl-co-2-hydroxypropyl acrylate) (PVC) polymer, silicon carbide, and equivalent materials.

In still another aspect of the invention is a nanoconverter, comprising: a nanostructure; and means for generating power from the nanostructure. The means for generating power from the nanostructure may comprise a molecular interaction zone portion of the nanostructure that interacts with molecules to generate power.

In yet another aspect of the invention, is a nanoconverter, comprising: a nanostructure comprising a molecule interaction zone that interacts with molecules in the molecule interaction to generate power through physisorption.

A device may be powered by any of the nanoconverters described above, wherein the device has no other power source.

The invention is susceptible to modifications and alternative forms. Specific embodiments are shown by way of example. It is to be understood that the invention is not limited to the particular forms disclosed. The invention covers all modifications, equivalents, and alternatives falling within the spirit and scope of the invention as defined by the claims.

Further aspects of the invention will be brought out in the following portions of the specification, wherein the detailed description is for the purpose of fully disclosing preferred embodiments of the invention without placing limitations thereon.

BRIEF DESCRIPTION OF THE SEVERAL VIEWS OF THE DRAWINGS

The invention will be more fully understood by reference to the following drawings which are for illustrative purposes only:

FIG. 5A is graph of the voltage vs. time response for the nanoconverter FIG. 4.

FIG. 5B is a graph of current (nA) vs. time response for the nanoconverter of FIG. 4.

FIG. 5C is a graph of the generated $V_{ocp}$ reported in Table 1 versus the dipole moment for several solvents, which are individually evaluated and graphed below in FIGS. 5D-5G.

FIG. 7A is a cross sectional diagram of the geometry of molecular interactions in the context of a nanoconverter.

FIG. 7B is a cross sectional diagram of an alternate nanoconverter geometry, where the top electrode has been placed atop the molecule interaction zone.

FIG. 8A is a cross sectional view of the nanoconverter geometry of FIG. 7B with no molecules present.

FIG. 8B is a graph of the energy levels corresponding to the device of FIG. 8A.

FIG. 8C is a cross sectional view of the nanoconverter geometry of FIG. 8A with molecules present.

FIG. 8D is a graph of the energy levels corresponding to the device of FIG. 8A with molecules present.

FIG. 10A is a graph of current output of a vertically aligned ZnO nanoconverter over a period of about 90 minutes.

FIG. 10B is a zoomed detailed view of the first 10 minutes of FIG. 10A.

FIG. 12D is a graph of the I-V curve of the $I_{sd}$ (nA) versus $V_g$ (V) of the device embodiment of FIG. 12B with no external voltage source (as was used instead in FIG. 12C).

DETAILED DESCRIPTION OF THE INVENTION

Definitions

The following definitions are provided to facilitate an understanding of the terminology used herein. It is intended that those terms not present in these Definitions be given their plain meaning as understood by those persons having ordinary skill in the art.

Nanoconverter means a device comprising nanoscale components that generates power when exposed to molecules. Such power generation is, without limitation, generally due to surface chemistry interactions.

Nanodevice means a device comprising a nanoconverter, a nanosensor, or other nanoscale component.

Nanosensor means a device comprising nanoscale components that generates an electrical signal when exposed to molecules. Such electrical signal generation is, without limitation, generally due to surface chemistry interactions. While the nanosensor and nanoconverter may be identical in some applications, their intended use may be different when used as a detective device, or as a power source.

Nanostructure means an object of intermediate size between molecular and microscopic (micrometer-sized) structures. In describing nanostructures at least one of the dimensions describing the structure is on the nanoscale, i.e., a size between 0.1 and 100 nm. Nanotubes or nanowires have two dimensions on the nanoscale, i.e., the diameter of the tube or wire is between 0.1 and 100 nm; its length could be much greater. Typical nanostructures include, but are not limited to: nanowire, nanosheets, nanotubes, nanotubes, nanoribbon, nanocages, nanofabrics, nanoflakes, and quantum dots.

Vertically aligned means a forest of nanowires or nanotubes that are more or less perpendicular to a substrate. Such nanowires or nanotubes are not restricted to being perfectly orthogonal to a substrate.

DESCRIPTION

Introduction

The present invention provides a nanoconverter system that will directly generate electricity through interactions with molecules. High surface-to-volume ratio semiconductor nanowires or nanotubes (such as ZnO, silicon, carbon nanotubes, etc.) are grown either vertically- or randomly-aligned on a substrate. Polymers or other types of materials (for example, silicon nitride) are used to seal portions or certain percentages of the nanowires or nanotubes. Subsequent exposure of portions of the nanowires or nanotubes to molecules allows the nanoconverter to generate an electric current and voltage. The molecules contain chemical energy and dipole momentum. When interacting with certain types of materials, these molecules can either be decomposed (through catalytic activities) or directly interact with semiconductor surfaces through charge-transfer or dipole-interactions. The nanoconverter system can also be used for sensing purposes without any external power supplies (i.e., batteryless sensing).

Nanoconverter Construction

Figure 1A:
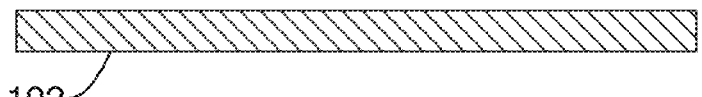
FIG. 1A is a cross section of a substrate for building a nanoconverter.

Refer now to FIGS. 1A thru 1E, which are cross sections illustrating the cumulative basic steps of construction of a nanoconverter 100 of the present invention. FIG. 1A shows the substrate 102 upon which the vertically aligned ZnO nanowires 104 will be grown. In this case the substrate 102 is a 2 mm×2 mm a-plane sapphire substrate. Other substrates including, but not limited to, SiC, silicon, glass, etc. may be used.

Figure 1B:
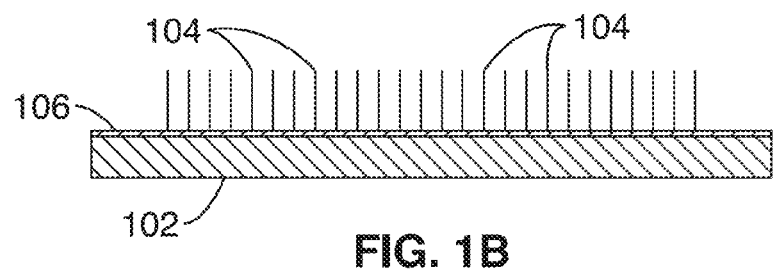
FIG. 1B is a cross section of the substrate of FIG. 1A with vertically aligned ZnO nanowires formed atop the substrate.

FIG. 1B shows a forest of epitaxially grown vertically aligned ZnO-nanowires 104 that have been grown on the sapphire substrate 102. The vertically aligned ZnO nanowires 104 were grown via a chemical vapor transport and condensation process or other method resulting in such vertically aligned nanowires 104. At the same that the vertically aligned ZnO nanowires 104 are grown, a thin layer of ZnO 106 forms on the substrate 102, which will subsequently become an electrode in the nanoconverter 100.

Figure 1C:
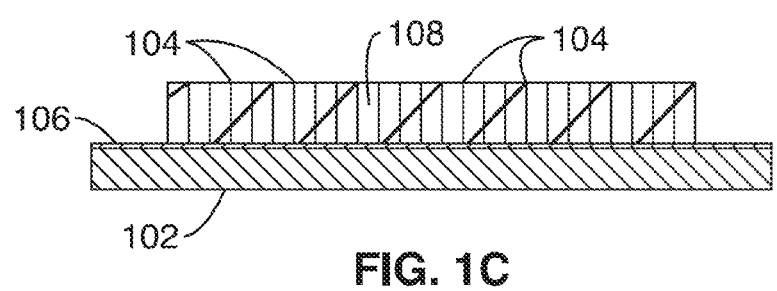
FIG. 1C is a cross section of the vertically aligned ZnO nanowires formed on the substrate of FIG. 1B, where the nanowires have been drop cast with PVC polymer layer or other insulator.

FIG. 1C shows the vertically aligned ZnO nanowires 104 after they have been infiltrated by drop casting a 1% PVC solution on the substrate 102. The physical and mechanical properties of PVC polymers allow for room temperature formation of uniform, flexible thin films. The polymer layer 108 at this stage completely covers the vertically aligned ZnO nanowires 104.

Figure 1D:
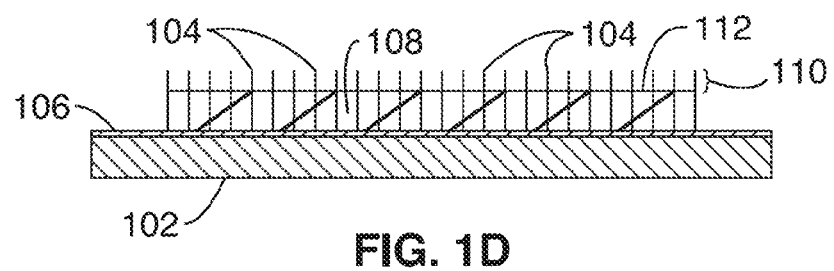
FIG. 1D is a cross section of the device of FIG. 1C, where a top layer of the PVC polymer layer has been oxygen etched for removal.

FIG. 1D shows that after curing the PVC film at room temperature, the top surface was oxygen plasma etched to clean and expose the vertically aligned nanowire 104 tips 110, leaving a cleaned plateau 112 below the tips 110. This cleaned plateau 112 is comprised of the polymer layer 108 of the previous FIG. 1C. The polymer layer 108 is generally impermeable to desired molecules, creating a molecule noninteraction zone for nanowires immersed and sealed within the polymer layer 108. A scanning electron microscopy image after the etching step will show the exposed nanowire tips 110 (which are ~0.1-0.5 μm long). The nanowire density is measured at ~15/μm$^2$.

Figure 1E:
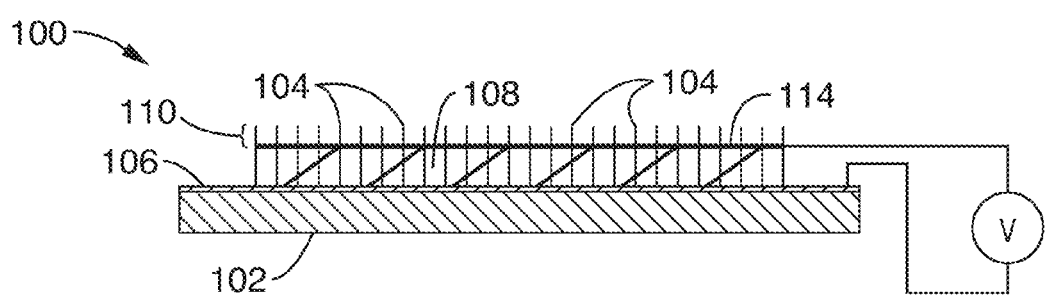
FIG. 1E is a cross section of the device of FIG. 1D, where a Au/Ti layer has been deposited over the oxygen etched polymer layer to form a second electrode.

FIG. 1E shows that a 200 μm Au/5 nm Ti layer 114 deposited via electron beam evaporation has been deposited on the exposed nanowire tips 110. This Au/Ti layer 114 will become the second electrode in the nanoconverter 100.

Figure 2A:
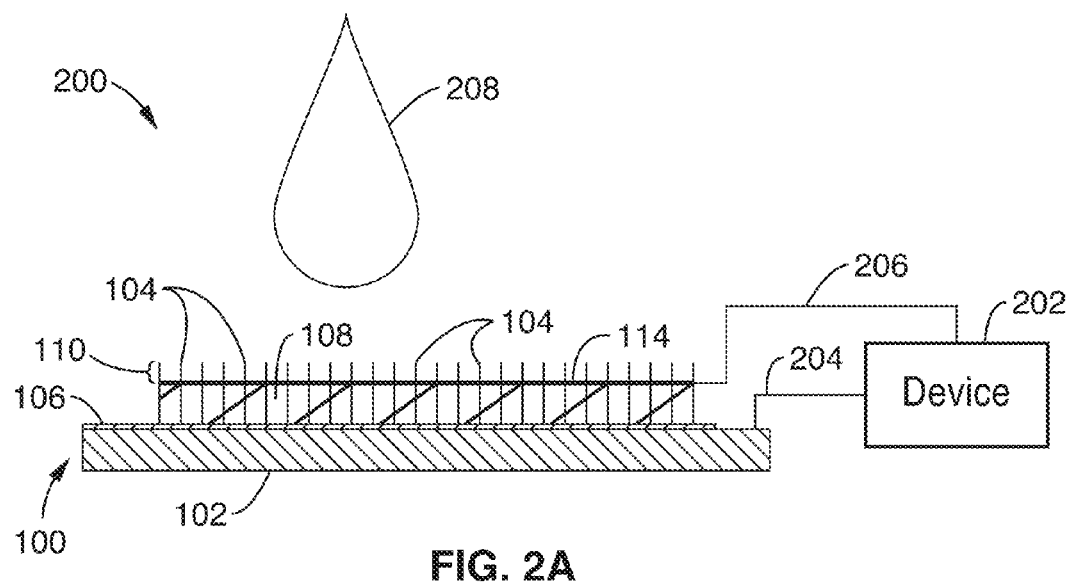
FIG. 2A is a cross section of the nanoconverter of FIG. 1E connected by electrical leads to an external device that is powered by the nanoconverter after the nanoconverter is wetted by a solvent molecule drop.

Refer now to FIG. 2A, which is a cross sectional view 200 of one embodiment of the nanoconverter 100 of FIG. 1E connected to a device 202 external to the nanoconverter. The nanoconverter 100 is connected to the device 202 by one connection 204 to the thin layer of ZnO 106 electrode of the nanoconverter 100, and by a second connection to the Au/Ti layer 114 electrode by a second electrical connection 206. The nanowires 104 are fabricated as previously described. The nanowires 104 form an interconnected nanowire network on the substrate 102. The two electrodes 106 and 114 electrically connect with nanowires 104. Part of the nanowire network is sealed below the Au/Ti layer 114 with a layer 108 comprising either a nonconductive polymer layer or epoxy, leaving the tips of the nanowires 110 exposed to molecules, usually wetted by drops 208. Electric voltage and current are generated when the molecule (polar solvents) drops 208 are contacted with the exposed tips 110 of the nanowires 104.

The nanoconverter 100 is connected by electrical leads to an external device 202 that will be powered by the nanoconverter 100. The external device 202 can be a device that provides a therapeutic or diagnostic function. For example, the device 202 in one embodiment is a glucose monitor. The device 202 in another embodiment is a pacemaker. The device 202 in another embodiment is a device enabling drug delivery. The device 202 in another embodiment is an insulin pump. The device 202 in another embodiment is a left ventricular assist device. The device 202 in another embodiment is cardioverter defibrillator. The device 202 other embodiments are devices for artificial muscles, artificial vision, and any such device that requires electrical power sources for operation. The generated electricity can also be directly stored in a battery.

Nanoconverter System for Producing Power Using Human Breath

Figure 2B:
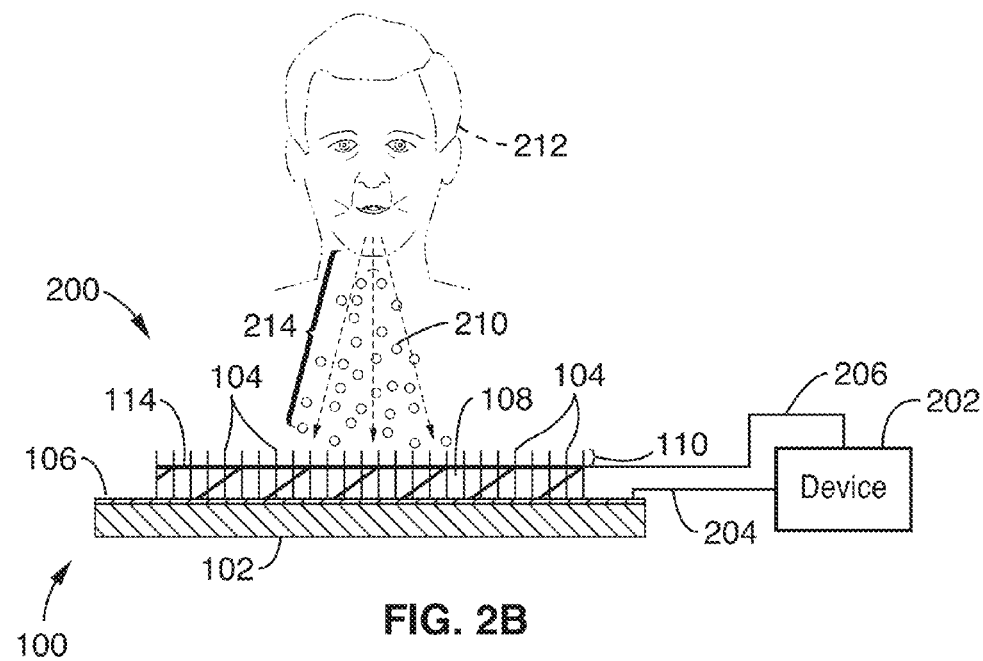
FIG. 2B is a cross section of the nanoconverter of FIG. 1E connected by electrical leads to an external device that is powered by the nanoconverter after the nanoconverter is breathed upon by a human or other living source.

Refer now to FIG. 2B, which is a nanoconverter system of FIG. 2A for producing power using human breath, with the nanoconverter shown in a cross sectional view. The nanoconverter is the same as previously described in FIG. 2A, but instead of being powered by a solvent molecule drop 208 in FIG. 2A, the ends of the nanowires are instead exposed to molecules 210 found in human 212 or other living breath 214. Electric voltage and current is generated when the polar solvents in breath 214 are exposed to the nanowire tips 110. The nanoconverter 100 is connected by electrical leads to an external device 202 that will be powered by the nanoconverter 100. Breath 214 allows the nanoconverter 100 to generate an electric current and power the external device 202.

The external device 202 can be a cell phone or other device that uses electricity. The external device 202 can be a device that provides a therapeutic or diagnostic function. For example, the device 202 in one embodiment is a glucose monitor. The device 202 in another embodiment is a pacemaker. The device 202 in another embodiment is a device enabling drug delivery. The device 202 in another embodiment is an insulin pump. The device 202 in another embodiment is a left ventricular assist device. The device 202 in another embodiment is cardioverter defibrillator. The device 202 in other embodiments may be devices for artificial muscles, artificial vision, and any such device that requires an electrical power source for operation.

Other Example Nanoconverter Embodiments

Figure 3A:
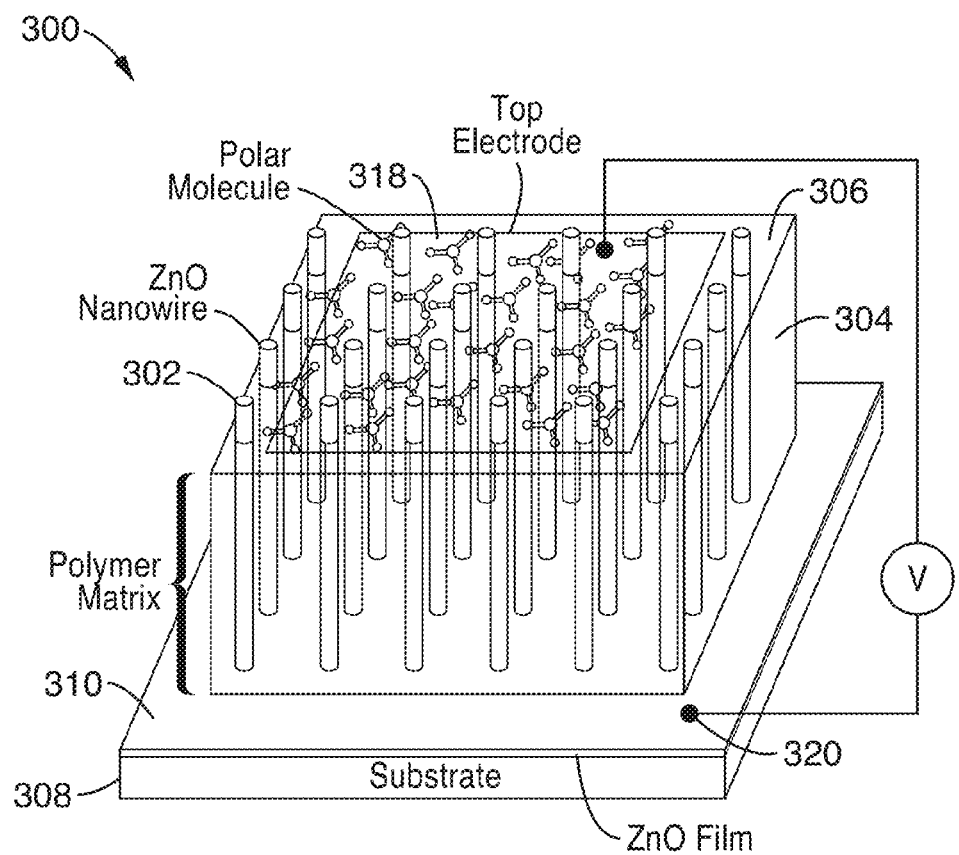
FIG. 3A is a perspective view of a nanoconverter of FIG. 1E based on vertically aligned ZnO nanowires (NWs) embedded in a polymer matrix.

Refer now to FIG. 3A, which is a perspective view of a nanoconverter 300 based on vertically aligned ZnO nanowires (NWs) embedded in a polymer matrix. This nanoconverter 300 was built to establish that electricity could be generated directly from molecules. Molecules exist ubiquitously in nature. To extract energy from molecules, a non-reversible oxidization process is typically required. Such chemical reactions occur endlessly inside the human body or other living systems as molecules (e.g., ribose, glucose, and fructose) diligently supply energy for animal daily activities. Provided that the chemical energy of these molecules can also be applied to generate the storable and clean electricity, an abundant amount of energy source could become available.

One key feature of the nanodevice invention here is the protrusion of ZnO NW tips 302 above the etched polymer matrix 304 surface 306. Single-crystalline semiconductor ZnO NWs are chosen as the functioning media as they are biocompatible and have fast electron transfer kinetics.

The crystal faces of ZnO, including the top polar (0001) or (000$\bar{1}$) and side nonpolar (10$\bar{1}$0) surfaces, can actively interact with various molecules. The NWs are epitaxially grown on an a-plane (110) sapphire substrate 308 via a chemical vapor transport and condensation process. The growth process produces a thin ZnO film 310 at the base of the NWs, which makes an ideal bottom contact for the vertically aligned ZnO nanowires.

Figure 3B:
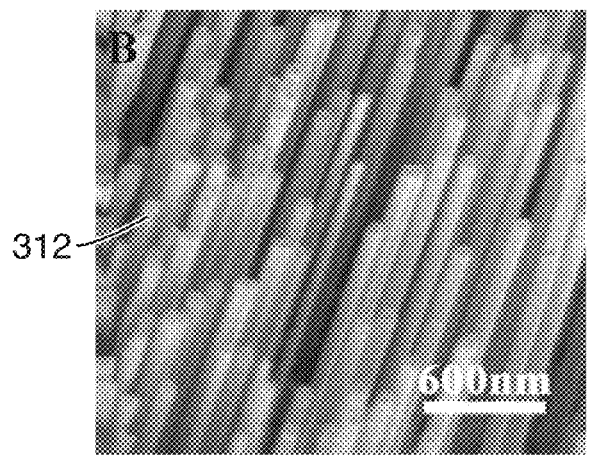
FIG. 3B is a scanning electron micrograph (SEM) of the as-grown NW diameters ranging from 60-120 nm and lengths span up to 10 μm prior to drop casting with a PVC polymer.

Refer now to FIG. 3B, which is a scanning electron micrograph (SEM) of the as-grown NW diameters ranging from 60-120 nm and lengths span up to 10 µm. The spacing between NWs is on the order of ~180 nm (i.e., with an areal density of ~30 NWs/µm$^2$). After growth, the NW forest is infiltrated with a poly(vinyl chloride-co-vinyl-co-2-hydroxypropyl acrylate) (PVC) polymer and etched in oxygen plasma so that ~5-10% of the NWs length is exposed for electric contacts as nanowire tips 312 and accessible to molecules.

Figure 3C:
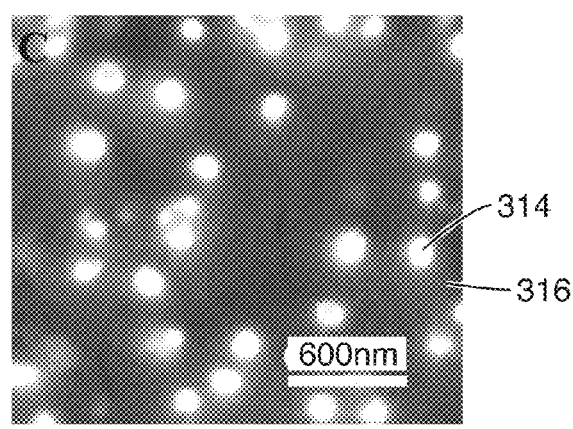
FIG. 3C is a scanning electron micrograph showing ZnO nanowire tips surrounded by an etched PVC polymer matrix.

Refer now to FIG. 3C, which is a scanning electron micrograph showing the nanowire tips 314 surrounded by the etched polymer matrix 316. An oxygen plasma etching process helps to remove contamination species such as hydroxyl or hydrocarbon groups on the NW surfaces so that a good electric contact can be made between the metal and ZnO nanowires. The etched polymer matrix 316 acts both as a sealant to block molecules from interacting with the bottom part of NWs.

Refer now back to FIG. 3A, the etched polymer matrix 304 surface 306 provides a supporting substrate for a top electrode (4 nm Ti/150 nm Au) 318. A silver paste 320 is chosen as the bottom electrical contact (with a thickness of 150 nm). After electrode patterning, all other areas of the device are sealed (not shown here) with epoxy (except for the exposed NW tips and the top surface) for environmental and electrical insulation.

Figure 3D:
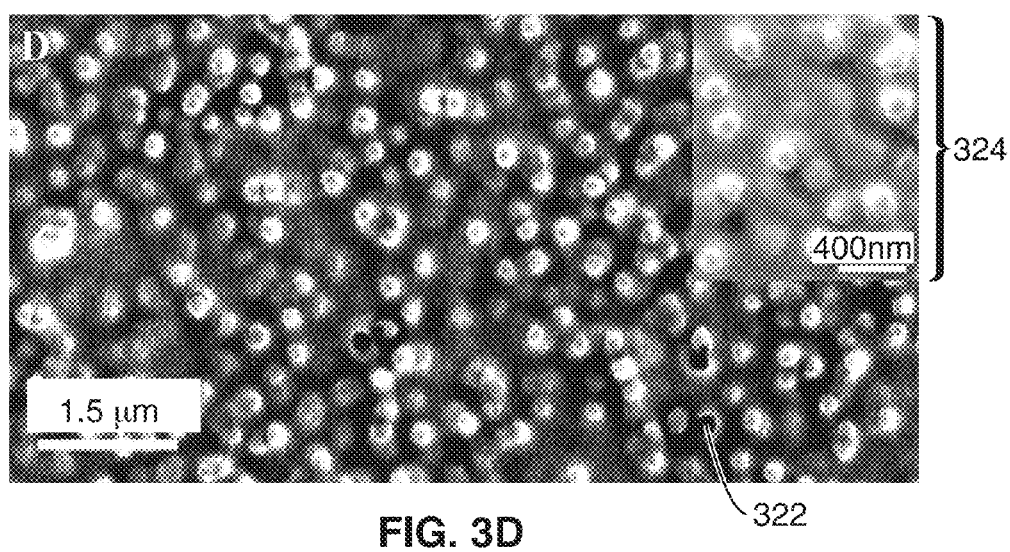
FIG. 3D is a scanning electron micrograph indicating that the metal coating is continuous but with some visible voids.

Refer now to FIG. 3D, which is a scanning electron micrograph image indicating that the metal coating is continuous but with some voids 322 apparent. The surface coverage area of top metal contact is ~1 mm×1 mm. Note that the exposed surface area of the nanodevice is not optimized, as the directional electron-beam evaporation process for the top electrode also coats some surfaces of the ZnO NW tips (as shown in the FIG. 3D inset 324).

Figure 3E:
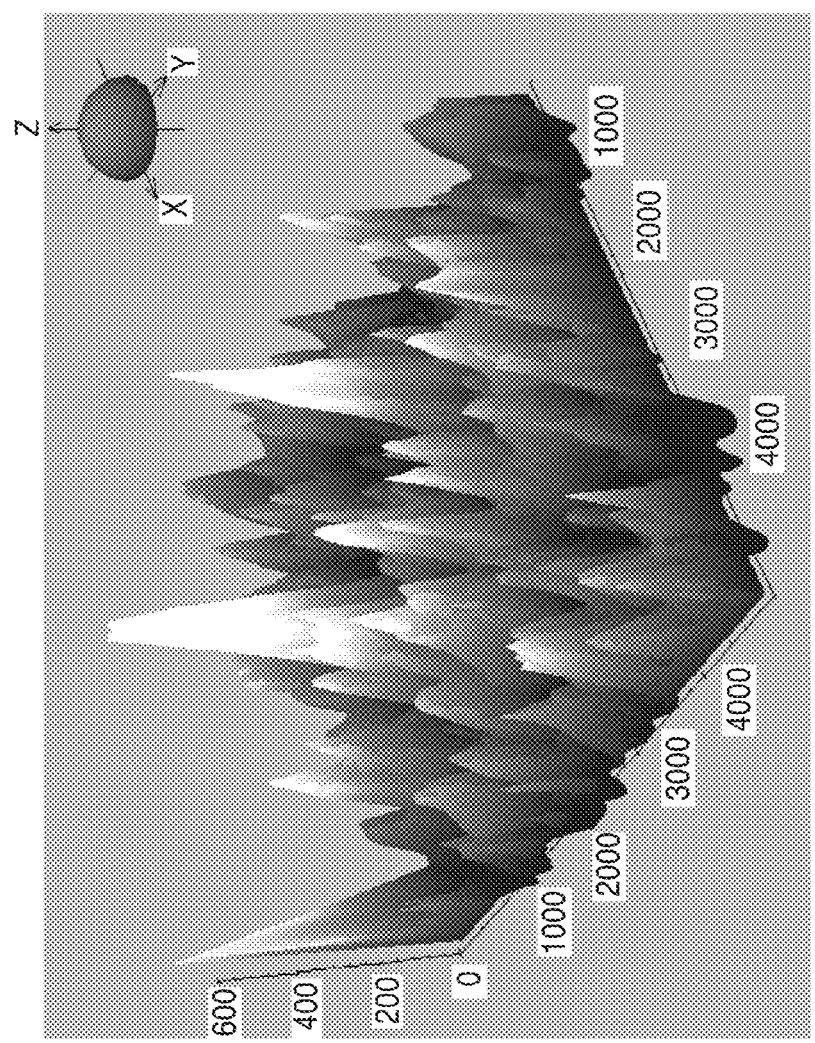
FIG. 3E is an atomic force microscopy (AFM) characterization of the surface Au/Ti coating of the nanoconverter of FIG. 3D, which shows that the height of exposed NW tips is 100-500 nm.

Refer now to FIG. 3E, which is an atomic force microscopy (AFM) characterization of the surface Au/Ti coating of the nanoconverter of FIG. 3D, which shows that the height of exposed NW tips is 100-500 nm.

Figure 4:
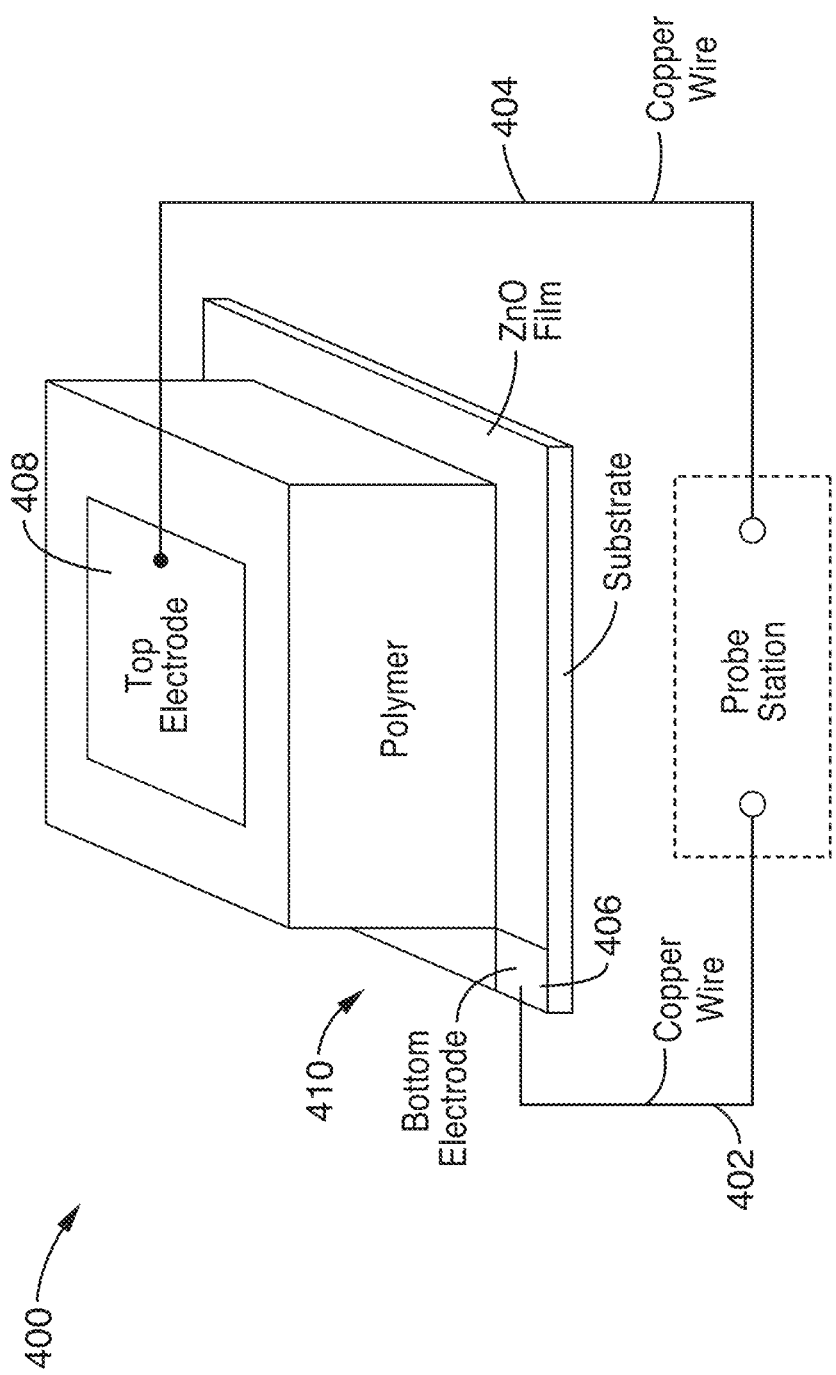
FIG. 4 is a perspective view of two floating contacts designed to circumvent noise generation from direct contact between probes and the electrodes for electrically testing the nanoconverter.

Refer now to FIG. 4, which is a perspective view 400 of two floating contacts designed to circumvent noise generation from direct contact between probes and the electrodes. Standard current versus voltage (I-V) measurements are applied to ensure that all test-bound devices have good metal contacts. Subsequent liquid solvent dripping experiments are carried out in ambient atmosphere without any external power source. Here, copper wires 402 and 404 respectively interconnect the bottom 406 and top 408 electrodes of the nanoconverter 410.

Figure 5E:
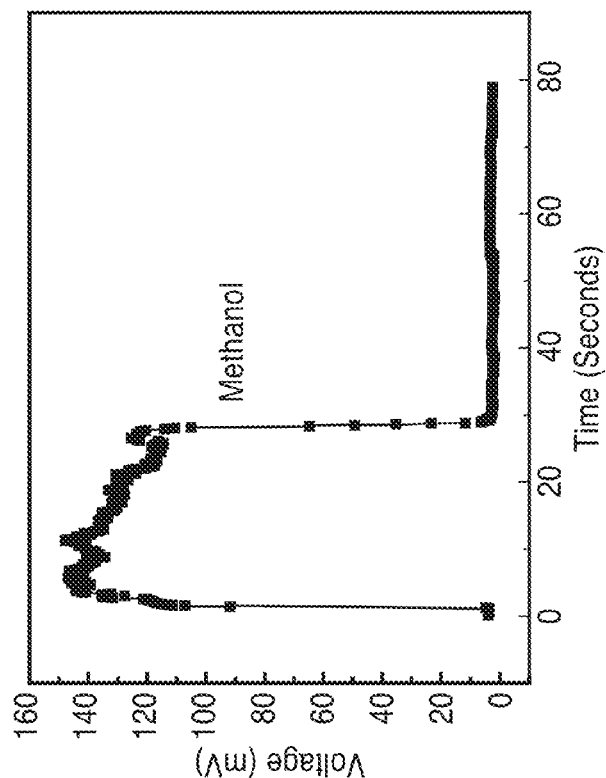
FIG. 5E is a graph of voltage vs. time of the nanoconverter response wetted with methanol.
Figure 5D:
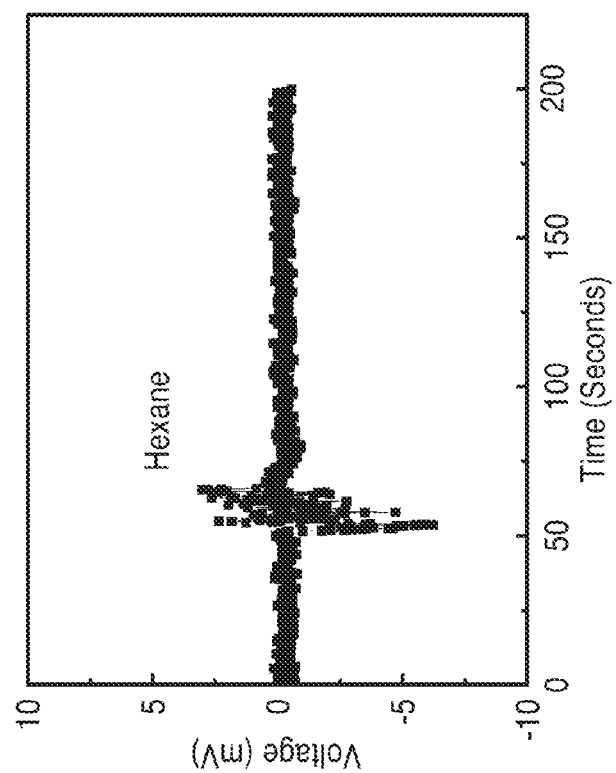
FIG. 5D is a graph of voltage vs. time of the nanoconverter response wetted with hexane.

Refer now to FIG. 5A, which is graph 500 of the voltage vs. time response for the nanoconverter 410 of FIG. 4. A sharp rise 502 of the open-circuit electric voltage ($V_{oc}$), with a peak value of over ~150 mV can be observed as a small volume (~2 µL) of ethanol is dripped onto the top surface of the nanoconverter 410 where ZnO NW tips are exposed. The rise of the voltage is relatively fast as the ethanol wets the device surface. The voltage signal maintains stable for a certain amount of time, but eventually decays due to the evaporation of ethanol solvent, typically within ~80-100 s. Significantly, the magnitude of the electric potential in the nanodevice is more than one order of magnitude higher than typically reported streaming potentials (up to ~10 mV) and piezoelectric voltages (~10-50 mV) generated by bending a ZnO (the system noise level of the probe station used here is ~50 µV). The electrochemical potential change of the top metal contact due to solvent wetting is measured using a device without nanowire protrusions, which shows a value in the range of 1-2 mV and corresponds to values reported elsewhere in the literature. These results suggest that the device function is dictated by interactions between solvents and semiconductor ZnO NWs (instead of the interactions between solvent molecules and metal surfaces). Importantly, the electric current reverses its sign but maintains a similar magnitude when the probes of the current/voltage meter are reversely connected, demonstrating that the measured current is not being generated by system noise but rather from the nanodevice itself.

Refer now to FIG. 5B, which is a graph 504 of current (nA) vs. time response for the nanoconverter 410 of FIG. 4. The measured short-circuit electric current ($I_{sc}$) shown in FIG. 5B indicates a value of tens of nanoamperes (nA). The rise of the electric current is sharp but decays rapidly with the time, leading to an asymmetric shape of the electric current signal. The device appears largely recoverable between two single drops as ethanol is highly volatile in the air and appears to largely evaporate between drops. The peak current and discharge times are nearly identical when additional drops of solvent interact with the NWs (after the preceding drop evaporates), which suggests that the electric potential for a given solvent type and volume is reproducible. The electric current reverses its sign but maintains a similar magnitude when the probes of the current/voltage meter are connected in reverse, demonstrating that the measured current is not being generated by system noise but rather by the nanodevice itself.

Note that the evaporation of volatile solvents such as ethanol can cause a measurable temperature fluctuation in the range of 2-5° C. on the nanodevice surface. The temperature fluctuations in turn invoke thermoelectric potentials between the two ends of ZnO NWs due to the Seebeck effect, or generate a piezoelectric voltage along ZnO NWs due to the thermal contraction/stretching of the PVC/NWs. To this end, temperature-controlled heating/cooling experiments have been performed, which indicate that such a combination of piezoelectric and thermoelectric voltages is no more than ~2 mV when the temperature change is less than 5° C. This value is almost two orders of magnitude lower than the voltage generated by the chemical solvents and is thus considered negligible.

Table 1 is shows an analysis of the open-circuit peak voltages ($V_{ocp}$) produced by drops of different chemical solvents, including volatile and non-volatile liquids, shows a complex correlation between the induced electric potential and physical properties of the solvents, with solvent drop volume fixed at 2 pL. Also listed are the dipole moment ($\mu$), heats of vaporization ($H_v$), and surface tension ($\gamma$) of the solvents at 25° C.

Refer now to FIG. 5C, which is a graph 506 of the generated $V_{ocp}$ reported in Table 1 versus the dipole moment for several solvents. For most solvents it is observed that a close relationship exists between their dipole moments and corresponding induced electric potentials. Nonpolar solvents such as benzene and hexane produce nearly zero voltage, while relatively polar molecules such as ethanol and methanol generate a large open-circuit voltage. Notably, several of the large dipole solvents, including water, dimethyl sulfoxide, N,N-dimethylformanmide, and N,N-dimethylacetamide produce a negligible or relatively small electric voltage. These observations suggest that molecular coverage (defined as C=n/m·100% where n and m are the numbers of solvent molecules and ZnO unit cells, respectively) may play an important role in generating the device potentials as the aforementioned solvents have either a high surface tension or a large molecular size. That the observed voltage signal is not correlated with $H_v$ of the solvents and non-volatile molecules also generate appreciable voltages supports the suggestion that the voltage source is not due to thermal fluctuation of our device and that the decay of voltage signals is likely attributed to the evaporation of solvents. The slow rise time of voltage signals for certain solvents (e.g., dimethyl sulfoxide and pyridine, respectively) offers another clue that electrochemical potential difference at the metal/ZnO nanowires interface may play a less important role in our devices.

Figure 5G:
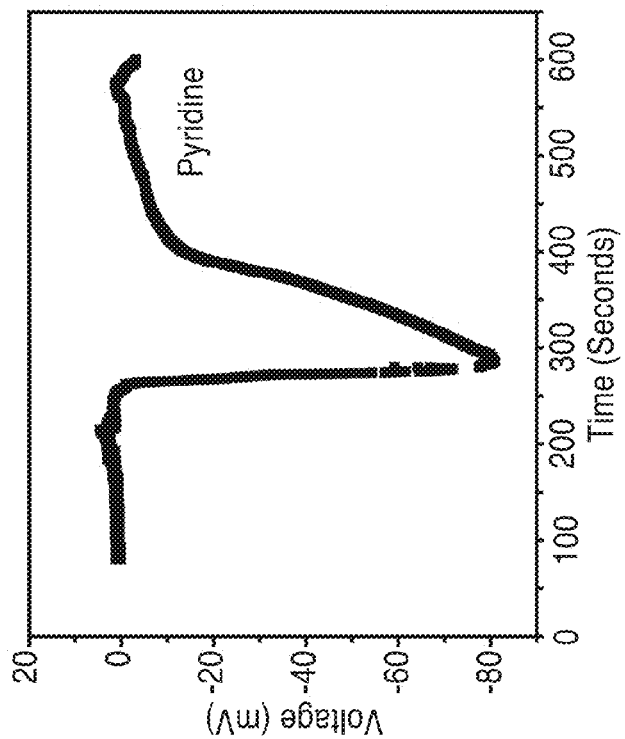
FIG. 5G is a graph of voltage vs. time of the nanoconverter response wetted with pyridine.
Figure 5F:
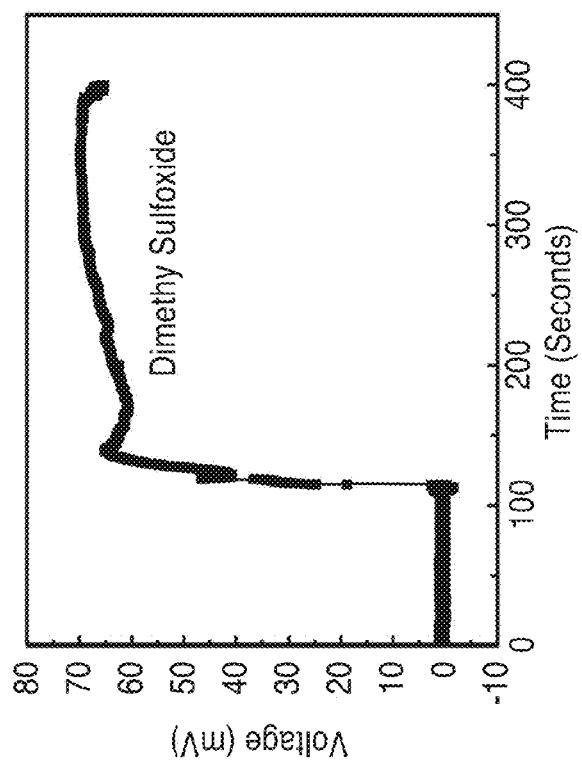
FIG. 5F is a graph of voltage vs. time of the nanoconverter response wetted with dimethyl sulfoxide.

Refer now to FIGS. 5D-5G, which are graphs of voltage vs. time of the nanoconverter response wetted with respectively hexane (FIG. 5D), methanol (FIG. 5E), dimethyl sulfoxide (FIG. 5F), and pyridine (FIG. 5G). These plots were used to develop the data of FIG. 5C.

To qualitatively understand the voltage generation mechanism in the nanoconverter, it is first noticed that as-grown ZnO NWs are n-type semiconductors with a carrier concentration on the order of ~5×10$^{17}$ cm$^{-3}$. The as-fabricated nanodevices typically have a non-ohmic top (T) contact due to the work function and electron affinity mismatch between Au (5.1 eV) and ZnO (4.5 eV), whereas the bottom/ground (G) contact is ohmic. An equivalent energy-band diagram of the nanoconverter device will be illustrated later, with the equilibrium Fermi level labeled as $E_F$.

Figure 6:
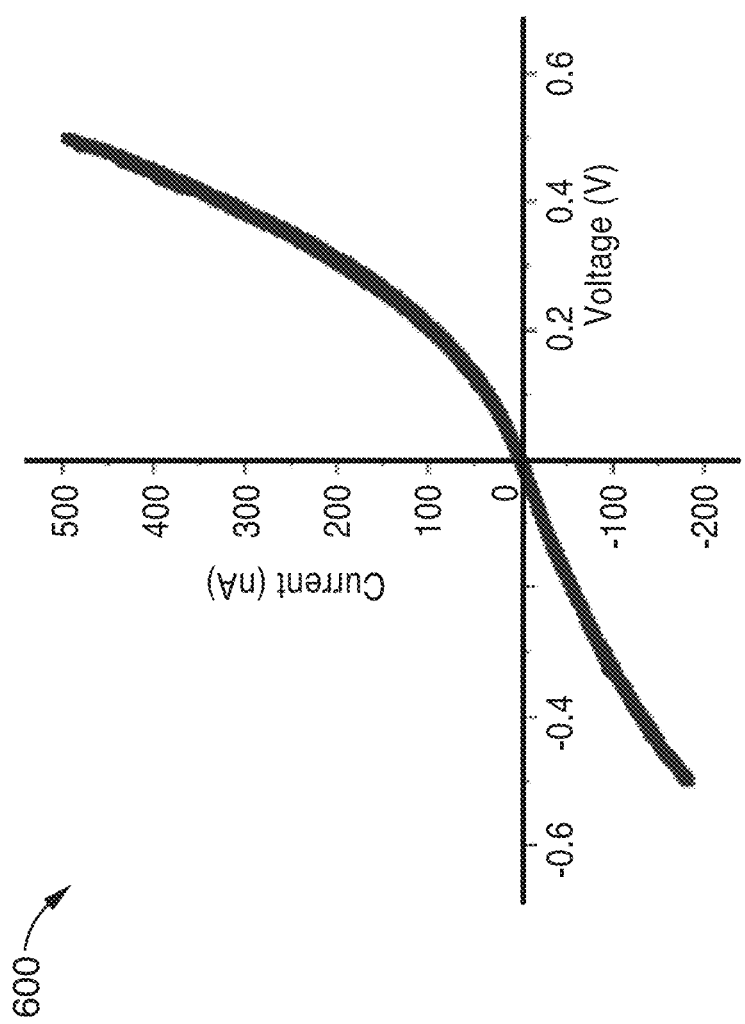
FIG. 6 is a graph of the electrical transport characteristics of a nanoconverter.

Refer now to FIG. 6, which is a graph of the electrical transport characteristics 600 of a nanoconverter. Next, the surface interaction between ZnO NWs and solvent molecules and its relationship with the chemical nature of these molecules is considered.

Refer now to FIG. 7A, which is a cross sectional diagram of the geometry of molecular interactions in the context of a nanoconverter 700. Here, a molecule interaction zone 702 appears at the top of the nanoconverter 700. A molecule interaction zone 702 generally appears at the tip of the ZnO nanowire 704 forest. The top electrode 706 may isolate permeation of the solvent molecule 708. Depending upon their charge transfer characteristic/ability relative to ZnO NWs, solvent molecules 708 can be divided into three different types: (1) electron-withdrawing type (e.g., methanol or ethanol), (2) electron-donating type (e.g., pyridine), and (3) neutral molecules (e.g., hexane).

Refer now to FIG. 7B, which is a cross sectional diagram of an alternate nanoconverter geometry 710, where the top electrode 712 has been placed atop the molecule interaction zone 714. The molecule interaction zone 714 is in turn atop the molecule noninteraction zone 716, then the bottom electrode 718. This is an alternate geometry embodiment of the initial geometry of FIG. 7A.

The molecule noninteraction zone 716 generally isolates a portion or percentage of a nanowire or nanotube from adsorptive contact with a molecule. Typically, the molecule noninteraction zone 716 may be created by impregnating a nanowire or nanotube forest with an epoxy or other polymer sealant so as to seal a region from access to molecules.

Generally it is much easier to create a forest of nanotubes or nanowires, and completely seal the forest with a sealant. Subsequently, the forest may be selectively etched to remove the sealant and consequently expose the nanotubes or nanowires. However, alternative methods of fabrication may require only selective sealing of a nanotube or nanowire forest with sealant, foregoing an etching process.

Refer now to FIGS. 8A and 8B. FIG. 8A is a cross sectional view 800 of the nanoconverter geometry of FIG. 7B with no molecules present. FIG. 8B is a graph of the energy levels corresponding to the device of FIG. 8A. Due to the ohmic nature of the ground electrode 802, this process equivalently elevates the Fermi level of ground contact/NWs to a new position $E_{FG}$, leading to a potential offset ($V_{off}$) between the top electrode ($E_{FT}$) and the ground contact ($E_{FG}$). The voltage sign we measured from the ethanol-driven devices agrees with the above qualitative picture (i.e., positive sign on the top contact). Conversely, one would expect a negative potential offset when electron-donating molecules are adsorbed onto the NW surfaces. This is likely to be the case for pyridine ($C_5H_5N$) (previously shown in FIG. 5G), which is a Lewis base with a lone pair of electrons to donate. The polarity switching ability of the nanodevices in response to different solvents further excludes the thermoelectric-dominant effects.

Refer now to FIGS. 8A through 8D. FIG. 8C is a cross sectional view 804 of the nanoconverter geometry of FIG. 7B and FIG. 8A with molecules 806 present. FIG. 8D is a graph of the energy levels corresponding to the device of FIG. 8C with molecules 806 present. Upon adsorption of ethanol molecules onto ZnO NW tips at the molecule interaction zone 808, the electron-withdrawing ability of these molecules shifts the conduction band (CB) 810 of ZnO away from the original Fermi level CB 812.

As a first order approximation, a value of maximum potential offset can be estimated from the change of the electron affinity of ZnO ($\Delta\chi$) after molecular adsorption. Assuming a single layer of molecular coverage, for bulk semiconductor materials the change in the electron affinity can be approximated by $$\Delta\chi^{ZnO} = N\mu \cos(\theta)/\in\in_0$$

where $\mu$ is the dipole moment of adsorbed molecule, N is the surface density of dipoles, $\theta$ is the average tilt angle of the dipoles normal to the ZnO surface, $\in$ is the layer's dielectric constant, and $\in_0$ is the dielectric permittivity of vacuum. The estimated $\Delta\chi$ value is on the order of ~350 mV for ethanol molecules (assuming 100% molecular coverage, $\mu$=1.39 D, $\theta$=0o, $\in$=8.91).

Figure 9A:
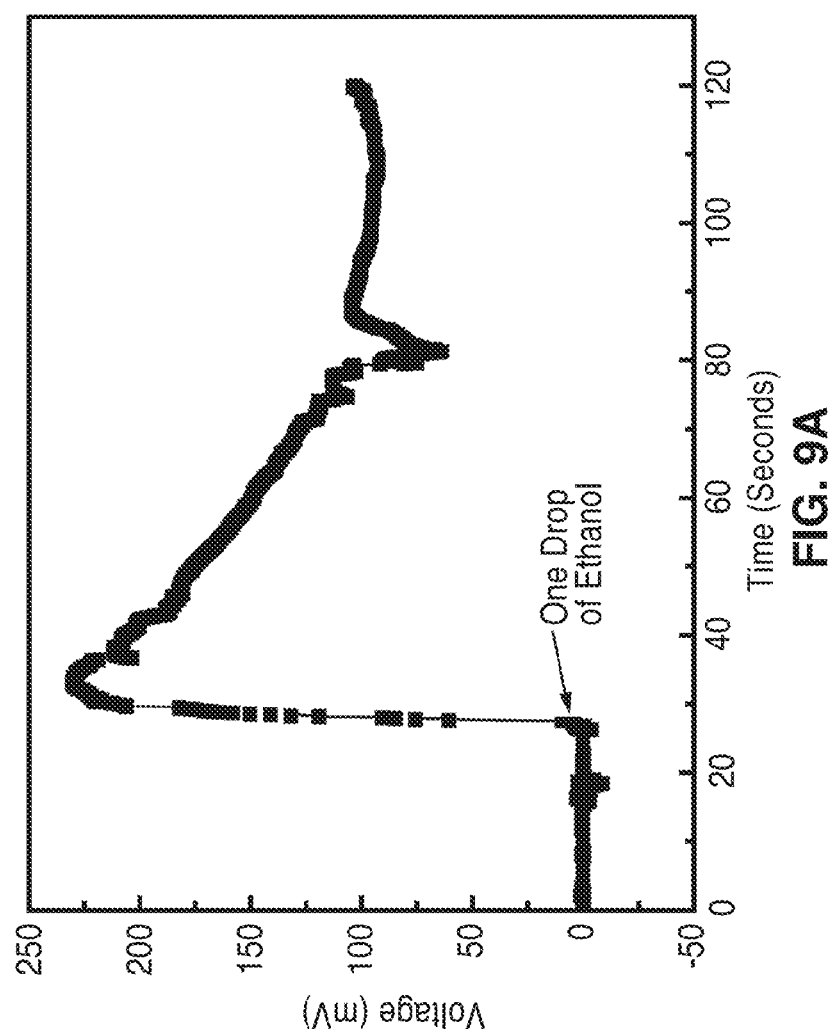
FIG. 9A is a graph of the electric potential signal (measured from a carbon nanotube nanoconverter after placing on drop of ethanol on the molecule interaction zone) versus time in seconds.
Figure 9B:
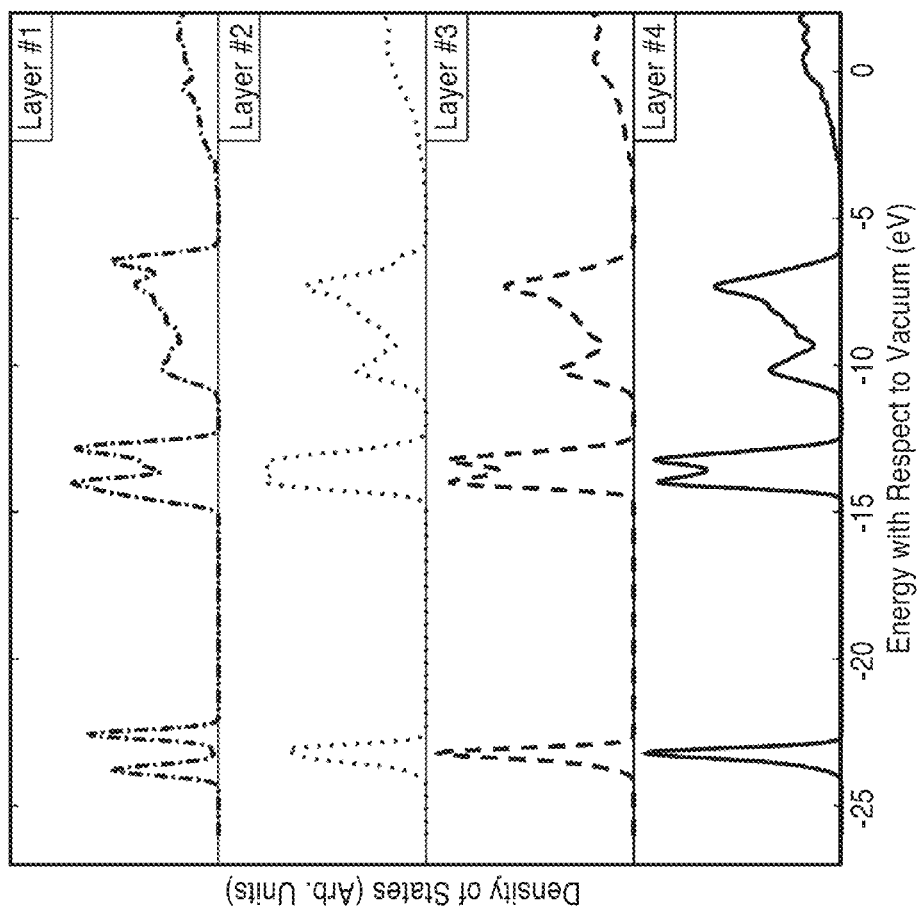
FIG. 9B is a plot of Densities of States (DOS) (in arbitrary units) for four different atomic layers of ZnO perpendicular to the (10$\bar{1}$0) surface, versus energy with respect to vacuum in eV.

Refer now to FIGS. 9A and 9B. FIG. 9A is a graph of the electric potential signal (measured from a carbon nanotube nanoconverter after placing on drop of ethanol on the molecule interaction zone) versus time in seconds. FIG. 9B is a plot of densities of states (in arbitrary units) for four different atomic layers of ZnO perpendicular to the (10$\bar{1}$0) surface, versus energy with respect to vacuum in eV. A device consisting of vertically aligned double-walled carbon nanotubes (CNTs) and silicon nitride sealant was fabricated, which yielded a relatively high electric voltage (~230 mV) when exposed to ethanol as shown in these FIGS. 9A and 9B. These results suggest a universal behavior of molecule-induced voltages.

In FIG. 9B, the density of states (DOS) for the third and fourth layers was the same as the bulk DOS. For the second and in particular for the first layer, marked changes occur in the splitting of the O-2s and Zn-3d peaks and the DOS near the valence band edge exhibits a surface related feature.

Although above qualitative hypotheses could explain various voltage signs and magnitudes observed in the experiments presented here, it is important to investigate whether these pictures represent true mechanisms of the nanoconverters and to understand the atomistic origin of molecule adsorption on ZnO NWs surfaces. Therefore, quantum mechanical calculations were carried out using density functional theory (DFT) and modeled the adsorption of both polar and nonpolar molecules on ZnO surfaces.

Electron Transport Characteristics Molecule-Surface Interactions

The width of molecule depletion (interaction) region can be estimated using the following equation:

$$W = \sqrt{\frac{2\varepsilon V_{bi}}{\rho}}$$

where $\in$ is the dielectric constant of ZnO, $V_{bi}$ is the built-in potential, and $\rho$ is the free-carrier density in ZnO nanowires. By using $\in$=8.91×8.85×10$^{-12}$ F/m² $V_{bi}$=1V for the case of ethanol based on our density-functional calculations, and $\rho$=5×10$^{17}$/cm³, one may obtain W=44 nm. This value suggests that the entire cross section of the nanowires is likely affected by molecule adsorptions.

Comparison Results of Vertically Aligned Double-Walled Carbon Nanotubes

The nanodevice based on vertically-aligned double-walled carbon nanotubes was fabricated using a procedure described in the literature, where the sealant material was silicon nitride. The as-grown double-walled nanotubes have diameters in the range of ~1-2 nm and a height of ~3-5 μm. Silver was used as top and bottom electrodes, respectively.

Modeling Details

A set of quantum mechanical calculations was carried out using the density functional theory (DFT), within the Vienna ab-initio simulation package (VASP) in order to study the interactions between solvent molecules and the (10$\bar{1}$0) ZnO surface at the atomic and electronic level. The projector augmented wave method was employed to represent the potential due to the ionic cores and the core electrons where the Zn-3d electrons were treated as part of the valence. The plane wave cutoff-energy was set to 500 eV to ensure proper convergence. We applied the generalized gradient approximation (GGA) to express the exchange-correlation potential. Using conventional exchange correlation potentials such as the GGA, the binding of the Zn-3d derived states is, however, strongly under-estimated due to their localized character. To compensate for this shortcoming, we used the GGA+U method in the form derived by Dudarev et al. 7 with U−J=7 eV.

Details on the choice of the U-J-parameter and a comparison with X-ray photoemission spectroscopy (XPS) data can be found in the literature. The occupation numbers for the electronic states were determined using a Gaussian smearing method with a standard deviation of sigma=0.1 eV. Using these computational parameters we obtained lattice parameters of a=3.196 Å and c=5.132 Å with an internal parameter of u=0.381. These values appear to be in good agreement with experimental data.

The majority of the surface calculations were carried out using periodic slab models with 16 atomic layers and 16 vacuum layers along the [10$\bar{1}$0] direction. The number of vacuum layers is equivalent to a distance of 24.9 Å between two opposing surfaces. These large values were chosen to converge the surface structures, energies and the local potential in the vacuum which is needed for calculating work functions.

Brillouin zone integrations were carried out using a 4×1×2 Monkhorst-Pack grid for cells with a 1×1 cross section and an equivalent 2×1×1 grid for cells with a 2×2 cross section. Structures were optimized until all forces were below 30 meV/Å. Work functions for clean and covered surfaces were calculated as the difference between the Fermi level of the slab model and the electrostatic potential in the vacuum region.

For the clean stoichiometric (10$\bar{1}$0) surface a surface energy of 1.08 J/m² is obtained, which is in very good agreement with values from the literature that vary from 1.0 to 1.2 J/m². The work function is calculated to be 5.25 eV, which somewhat overestimates the experimental value of 4.64 eV. The difference could be related to the fact that the literature experiments carried out for n-type material for which the Fermi level is close to the conduction band minimum, whereas in the calculations here the Fermi level is located in the centre of the band gap.

Several polar and non-polar molecules were considered here, but the focus was on methanol and methane as prototypes for polar and non-polar adsorbents, respectively. Prior to placing the molecule in question onto the surface, its structure was relaxed in a cubic cell with a side length of 20 Å. Subsequently a variety of possible surface configurations were generated, for example, in the case of methanol we considered a total of 32 different models. For each configuration we obtained the relaxed structure, the total energy, and the local electrostatic potential from which we determined adsorption energies, work functions and electron affinities.

Electronic Structure of ZnO Surface and the Solvent

To improve an understanding of the changes in the electronic structure of both ZnO and the solvent (methanol as an example) during the adsorption process, a careful analysis of the density of states was performed. To this end, a non-self-consistent set of calculations was carried out with a finer k-point mesh and projected the DOS onto sites and decomposed them by orbital quantum number. The main results are summarized in FIGS. 9C-9E described below.

Figure 9C:
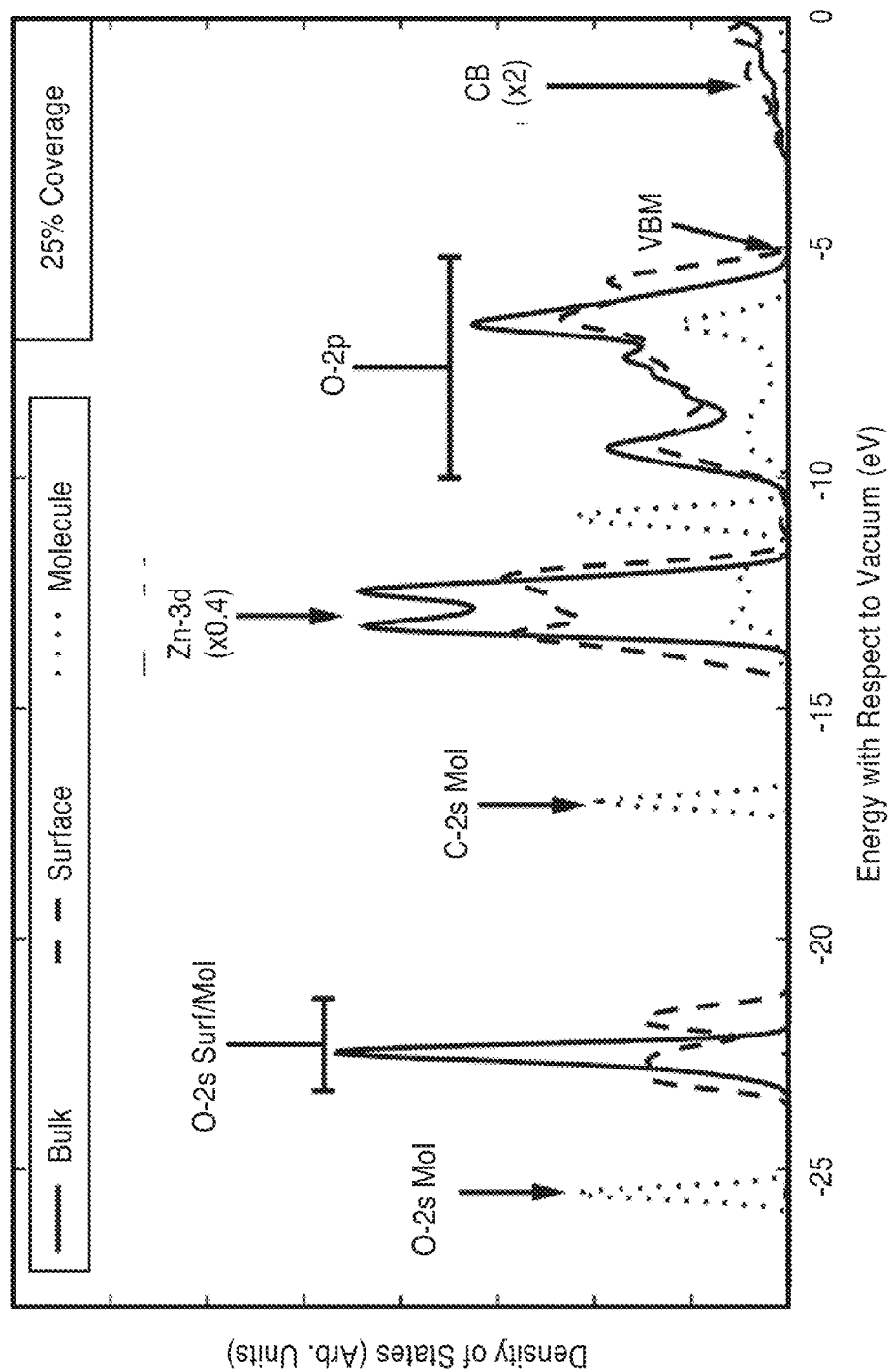
FIG. 9C is plot of the calculated differences in the electronic structure Densities of States (DOS) for different atomic layers perpendicular to the surface of a 25% methanol covered ZnO surface, with the most prominent features indicated and labeled.

Refer now to FIG. 9C, which is plot of the calculated differences in the electronic structure Density of States (DOS) for different atomic layers perpendicular to the surface of a 25% methanol covered ZnO surface, with the most prominent features indicated and labeled. First, the DOS of an ideal ZnO surface is considered. For the third and fourth layer, the DOS is virtually identical to the bulk DOS (calculated independently and not shown here). The second and specially the first layer, however, show several features that are clearly distinct from the bulk behavior. One of the most notable features is the splitting of the deep O-2s state, which can be related to the two different bonding environments for O-atoms in the first layer.

Similar conditions for the Zn ions give rise to a broadening of the Zn-3d peak. Finally, a pronounced state near the valence band edge may be observed that is primarily composed of O-2p states.

Figure 9D:
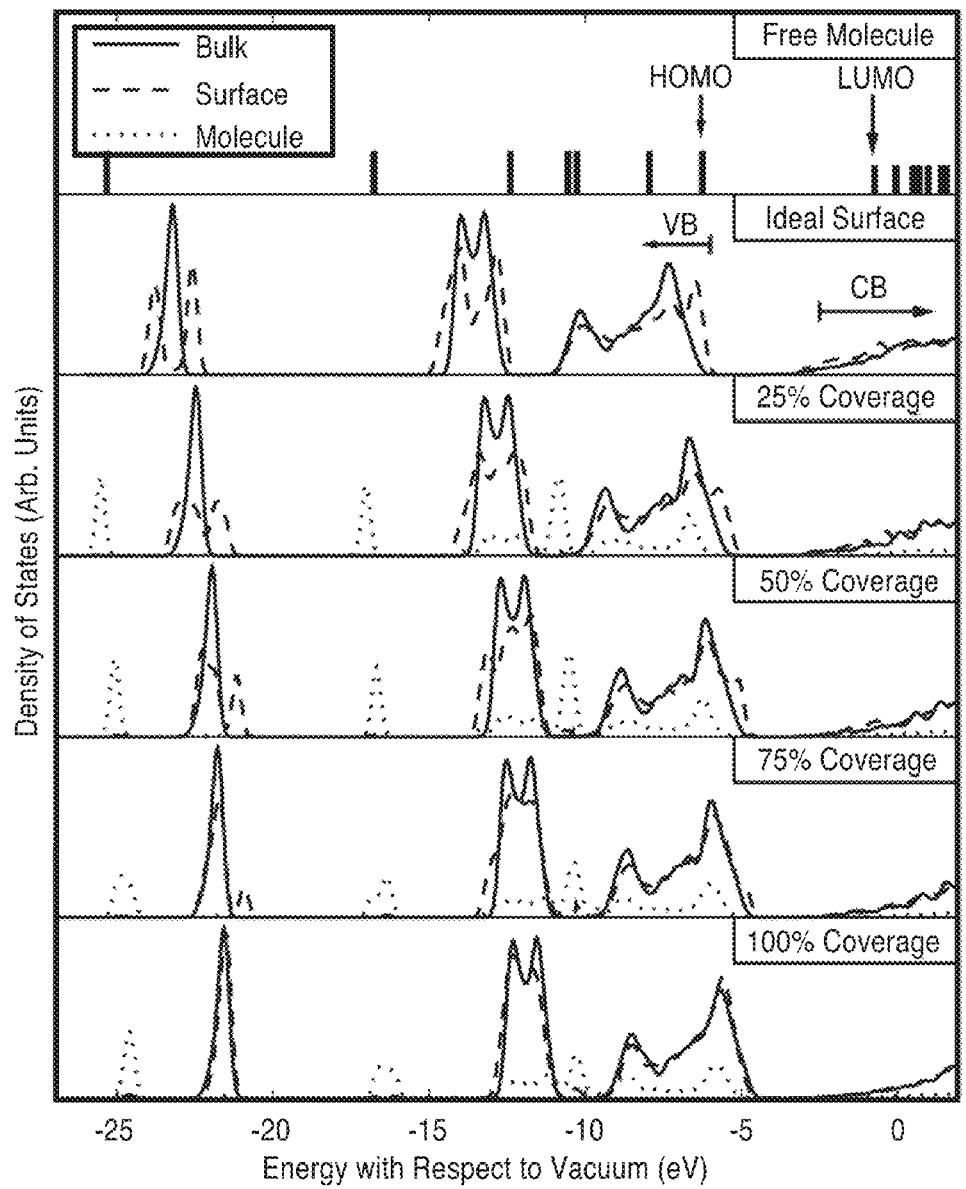
FIG. 9D is a plot of the DOS that reveals the changes in the electronic structure for various percentages of methanol coverage.

Refer now to FIG. 9D, which is a plot of the DOS that reveals the changes in the electronic structure for various percentages of methanol coverage. Comparison of the clean and the 100% covered surface shows the most dramatic differences. As discussed above, the ideal surface shows a splitting of the O-2s peak, a broadening of the Zn-3d peak, and a pronounced peak near the valence band edge. All of these features have practically vanished at 100% coverage and the DOS for the first (surface) layer is indistinguishable from the bulk DOS. The DOS at 25%, 50%, and 75% coverage show a gradual transition between the two extreme cases.

With regard to the molecular states, one must first allude to the levels of the free methanol molecule. Calculations here indicate that the highest occupied molecular orbital (HOMO) lies just below the valence band maximum (VBM) of the semiconductor, whereas the lowest unoccupied molecular orbital (LUMO) is located just above the conduction band minimum (CBM). When the molecule adsorbs onto the ZnO surface, its electronic structure changes markedly. The O-2p and C-2s states, which energetically overlap with the upper valence band of the semiconductor, display a pronounced hybridization with the surface orbitals. In particular, they exhibit a maximum right below the VBM, which correlates with the HOMO of the free molecule. In contrast, the O-2s and C-2s states remain largely unaffected except for the broadening which is a result of methanol—methanol interaction. Since the O-2s orbitals of the molecule and the surface are localized near the ionic cores, they do not interact with each other. It is, however, noteworthy that there is an energetic offset between the O-2s states of the molecule and the surface.

As the coverage increases, one observes a broadening of the molecular states (compare e.g., the near-VBM peak or the C-2s peak) because of the decreasing methanol—methanol separation, and a slight shift of the molecular levels with respect to the bulk and surface states.

Figure 9E:
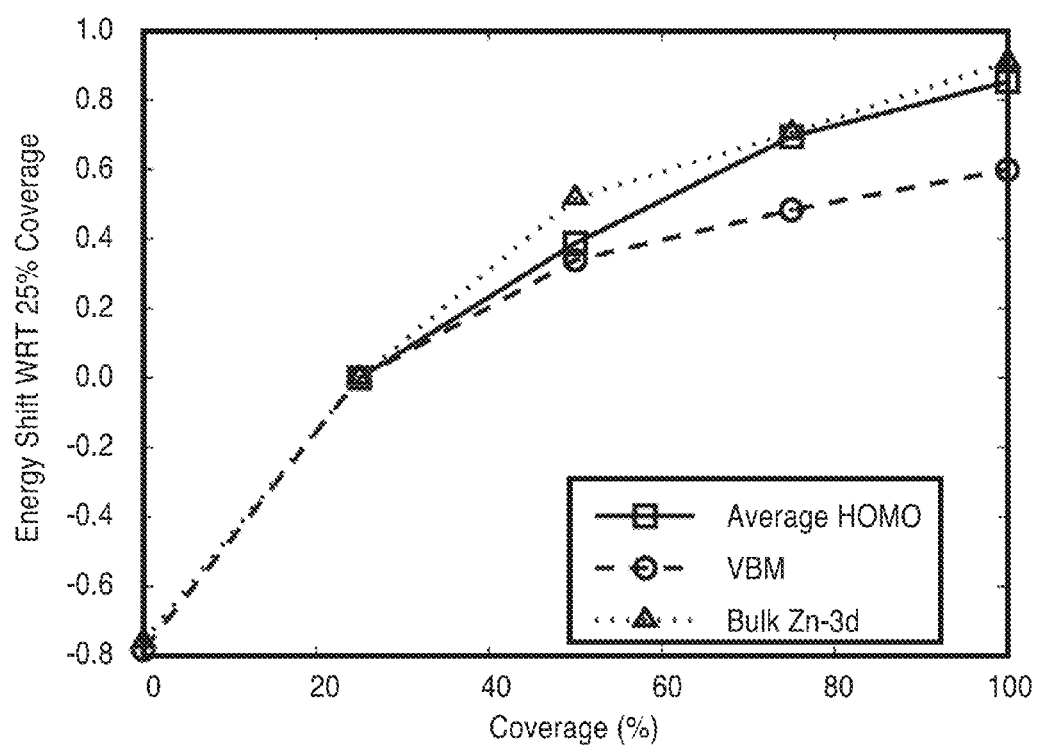
FIG. 9E is a graph that shows the position of the highest occupies molecular orbital (HOMO)-derived molecular state near the conduction band minimum (VBM) as a function of coverage, in comparison with the energetic position of the VBM and the Zn-3d states, where the conduction band (CB) shown.

Refer now to FIG. 9E, which is a graph that shows the position of the HOMO-derived molecular state near the VBM as a function of coverage, in comparison with the energetic position of the VBM and the Zn-3d states. This is visualized more clearly in FIG. 9E, where acronyms HOMO means highest occupied molecular orbital, and LOMO means lowest occupied molecular orbital. As the coverage increases, the HOMO-derived level not only broadens but also moves closer to the valence band edge, indicating that the barrier for carrier transfer shifts with the amount of methanol on the surface.

Nanoconverter Generation of Continuous Power

To generate constant power with a vertically aligned ZnO NW nanoconverter, it is necessary to maintain an electric potential difference (i.e., electron affinity gradient) along the NWs.

Refer now to FIGS. 10A and 10B. FIG. 10A is a graph of current output of a vertically aligned ZnO nanoconverter over a period of about 90 minutes. FIG. 10B is a zoomed detailed view of the first 10 minutes of FIG. 10A.

It was found that continuous power could be realized by constantly adding new molecules to the surface of the nanoconverter in the molecule interaction zone. Using methanol as a test solvent, a continuous and stable-direct-current was observed when the dripping frequency of the solvent reached approximate 1 droplet per 40 seconds with 2.2 µL per droplet.

FIG. 10B reveals that the apparently stable current of FIG. 10 A instead consists of numerous overlapping discharge cycles. Notably, this nanoconverter has been operated in direct-current mode for more than 90 minutes without seeing any degradation in electrical performance.

It is proposed that dynamic adsorption and evaporation processes of solvent molecules on the ZnO NW surfaces play a key role in maintaining the continuous current. As molecular dipoles adsorb to the surfaces of a ZnO NW, its tip is charged and diffuse double layers (DL) are formed at the solvent-NW interfaces. The subsequent discharge process not only neutralizes the potential along the NW, but also destroys the DL structures, leading to a change in the solvent-NW interactions. In the meantime, the thermal evaporation of the solvents changes the molecular coverage and thus the potential of ZnO NWs. It is not well-understood at present, however, whether the charge transfer between the ZnO and molecules and/or the heterogeneous chemical reactions occurs on the surfaces of ZnO nanowires during this discharge process. To re-establish new potential difference, one needs to add new polar molecules to the system to compensate for the loss of solvents due to evaporation and/or chemical reactions.

The nanoconverter has also been tested for longevity. Even after sitting periods of 8 months or more in a desiccator, the nanoconverters performed nearly identically to newly fabricated ones. Long-term exposure of the nanoconverter in air does appear to increase the accumulation of contaminating species on the device surface. However, by treating the nanoconverter to a short oxygen plasma exposure, the nanoconverter can be recovered to a functional state.

DFT Modeling

DFT calculations were chosen instead of other surface characterization techniques (such as thermal desorption spectroscopy or x-ray photoelectron spectroscopy) because nanoconverters contain various types of surfaces (metal, polymer, and ZnO) that tend to compromise these measurements. The simulations show a strong correlation between the adsorption energy ($E_{ad}$), electron affinity of ZnO ($\chi^{ZnO}$), and the dipole moment of the molecules. They also allude to the dependence of $\chi^{ZnO}$ on the surface coverage. The basic tenets of molecule-surface interactions and their effects on the electron affinity of ZnO and the adsorption energy are illustrated in FIGS. 11A-E, as described below.

Figure 11A:
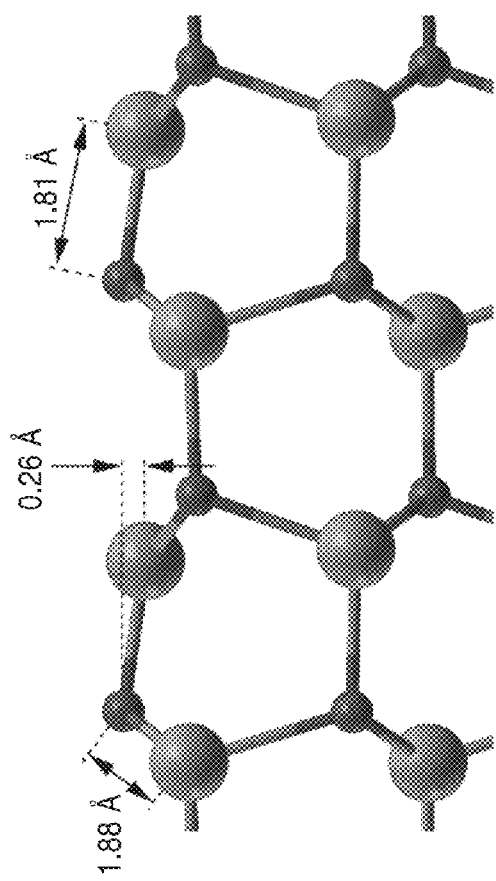
FIG. 11A is a DFT model of solvent interactions on the nonpolar, (10$\bar{1}$0) oriented side surfaces of the ZnO nanowires (NWs).

Refer now to FIG. 11A, which is a DFT model of solvent interactions on the nonpolar, $(10\bar{1}0)$ oriented side surfaces of the ZnO NWs. For simplicity, we assume the majority of the solvent interactions occur with the nonpolar, $(10\bar{1}0)$ oriented side surfaces of the ZnO NWs.

Figure 11B:
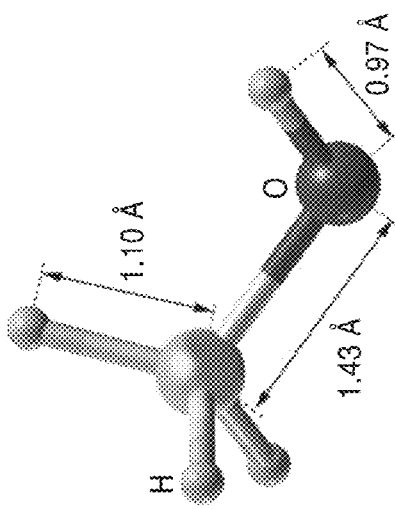
FIG. 11B is a DFT model of polar molecules, such as methanol, interacting with the nonpolar, (10$\bar{1}$0) oriented side surfaces of the ZnO NWs.

Refer now to FIG. 11B, which is a DFT model of polar molecules, such as methanol, interacting with the nonpolar, $(10\bar{1}0)$ oriented side surfaces of the ZnO NWs. When polar molecules such as methanol ($CH_3OH$) interact with this surface, the adsorption energy is found to be large and negative.

Figure 11C:
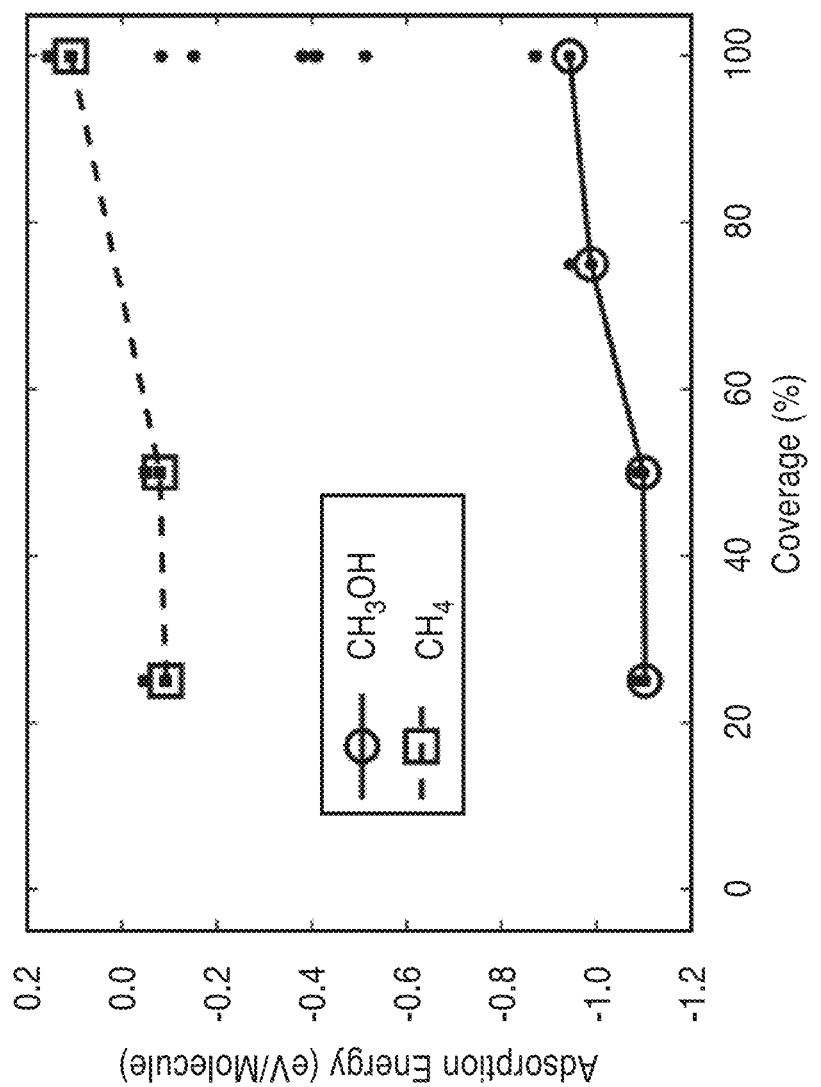
FIG. 11C is a graph of the modeled adsorption energy versus coverage percent for propane and methanol.

Refer now to FIG. 11C, which is a graph of the modeled adsorption energy versus coverage percent for propane and methanol. Both such adsorption energies are found to be exothermic, implying that the adsorption is energetically favorable.

Figure 11D:
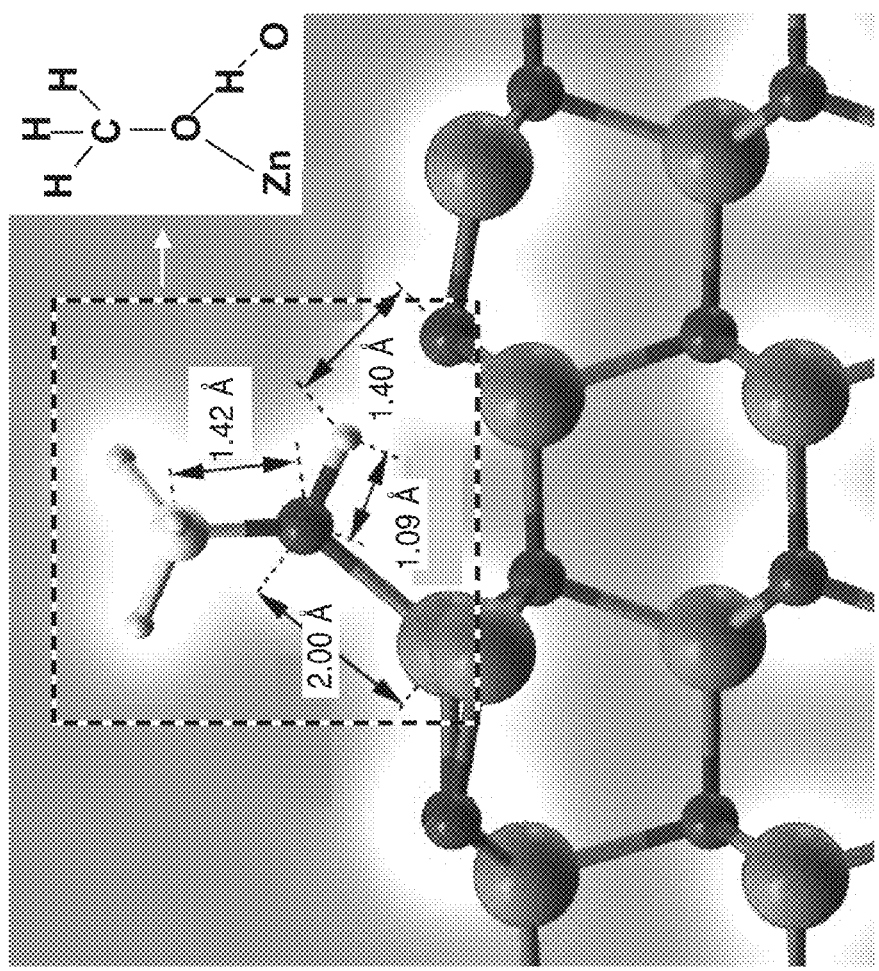
FIG. 11D is a DFT model of a methanol interaction on the nonpolar, (10$\bar{1}$0) oriented side surfaces of the ZnO NWs.

Refer now to FIG. 11D, which is a DFT model of a methanol interaction on the nonpolar, $(10\bar{1}0)$ oriented side surfaces of the ZnO NWs. The minimum energy configuration for a methanol molecule adsorbed on a $(10\bar{1}0)$ surface according to the DFT calculations is shown, indicating that the large adsorption energy is mostly attributed to the formation of a coordination bond between the O-atom of the molecule and a surface Zn-atom, leading to a charge transfer (the electronic structures of ZnO and solvents after adsorption was previously shown in FIGS. 9C-9E).

Referring back now to FIGS. 11B through 11D, it is noted that when the free methanol molecule geometry is compared to the adsorbed configuration, not much change in the bond lengths is observed when comparing FIG. 11B to FIG. 11D. The adsorption energy per molecule (as shown in FIG. 11C) as well as the adsorption geometry is relatively insensitive to the surface coverage except for the highest coverage level where steric repulsion between molecules causes a slightly less negative adsorption energy.

Figure 11E:
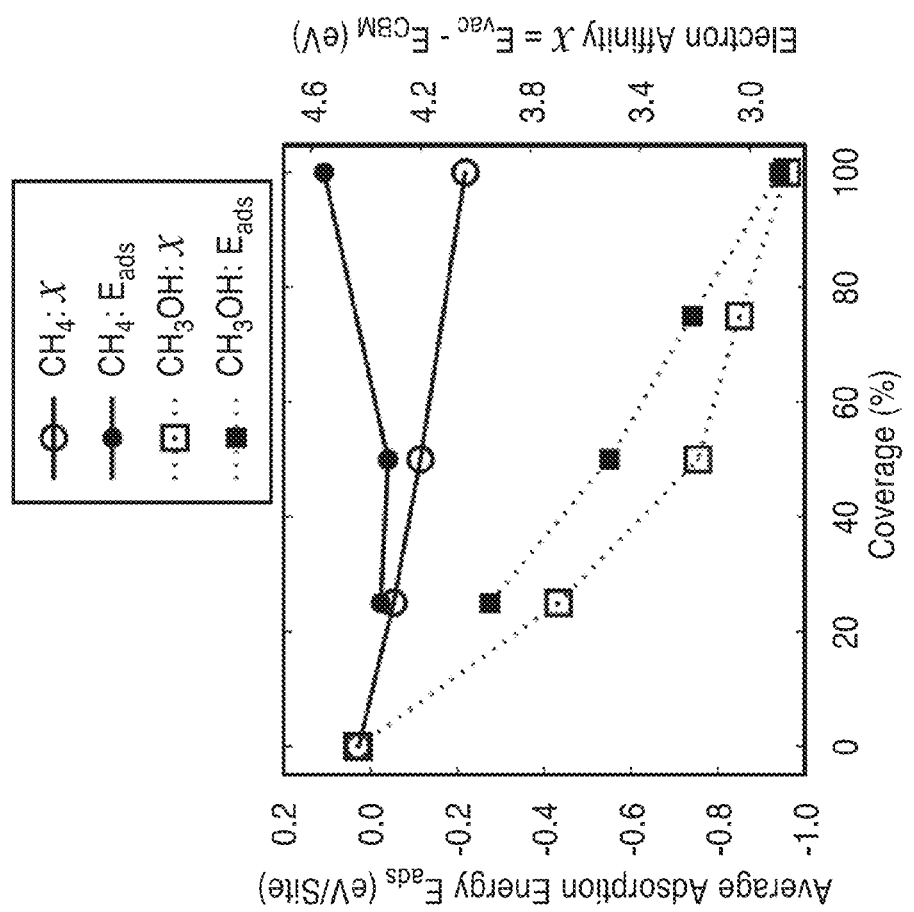
FIG. 11E is a graph of the modeled adsorption energy versus coverage percent for propane and methanol electron affinity and energy of adsorption.

Refer now to FIG. 11E, which is a graph of the modeled adsorption energy versus coverage percent for propane and methanol electron affinity and energy of adsorption. As illustrated in FIG. 11E, the adsorption process not only affects the surface energetics but also leads to a pronounced change in the electron affinity of the surface. This effect increases monotonically with the number of molecules on the surface and appears to be generic for polar molecules. A Bader analysis suggests that the static charge transfer between the molecule and the surface is relatively small (~0.01 eV per molecule) during the initial adsorption process, but causes a substantial change of the electron affinity of ZnO)($\chi^{ZnO}$) NW surfaces.

Refer now to FIGS. 11C and 11E. In contrast to the case of polar molecules, the interaction between nonpolar molecules such as methane and the ZnO surfaces is rather weak with regard to the calculated adsorption energy (FIG. 11C) as well as the electron affinity (FIG. 10E). In fact, the adsorption energy is only slightly negative for low molecular coverage and becomes even positive for maximum coverage. For a 100% surface coverage of methanol, the electron affinity of ZnO ($\chi^{ZnO}$) is reduced from a value of 4.5 eV (calculated for a clean surface) to 2.8 eV, whereas only a small change (~0.3-0.4 eV) is observed for methane. Calculations reveal a similar trend for other polar and nonpolar molecules interacting with the nonpolar ($10\bar{1}0$) surface, as well as with the polar (0001) and (000$\bar{1}$) surfaces. This disparity between polar and nonpolar molecules directly affects their charge-transfer ability, and agrees well with experimental observations that nonpolar molecules do not give rise to a macroscopically measurable voltage/current. Although these calculations were limited by the number of ZnO unit cells in the slab, it is expected that the change in electron affinity occurs over the entire cross-section of ZnO NWs due to their nanometer scale diameters.

It is noted that these qualitative analyses and DFT calculations have not considered the potential catalysis of ZnO surfaces to solvent molecules and other possible molecular excitation mechanisms. However, it is expected that these effects would be small as the appreciable catalytic activities of ZnO surfaces to organic molecules only occur at elevated temperatures (>150° C.), and as ZnO is a wide-band gap material (e.g. =3.37 eV at room temperature), making direct molecular excitation nearly impossible.

Human Breath Powered Nanoconverter

Since polar molecules (dipole containing species) exist ubiquitously in living systems or exhaustion gases (or exhalation gases), nanoconverters have been tested for output device signals using exhaled human breath. The molecular profile of breath contains a bulk matrix of carbon dioxide, nitrogen, oxygen, water vapor, inert gases, and other gaseous species, with as many as 500 different compounds. Even though the majority of these molecules are nonpolar, many volatile molecules contributed from blood, cells or tissues in the nose, sinuses, mouth, and the gastrointestinal tract carry a tangible dipole moment.

Figure 12A:
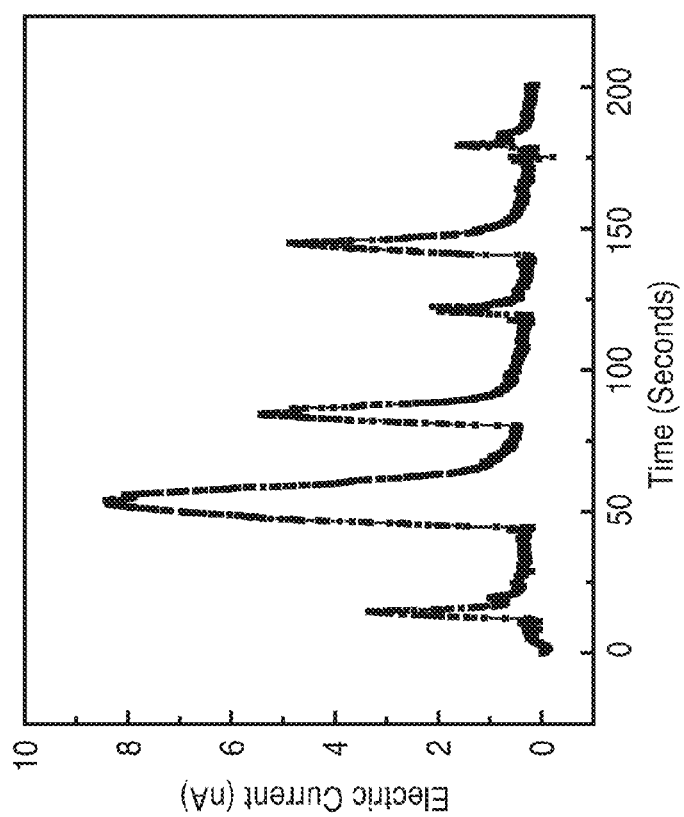
FIG. 12A is a graph of vertically aligned ZnO nanoconverter current (nA) versus time while exposed to human exhalation.

Refer now to FIG. 12A, which is a graph of vertically aligned ZnO nanoconverter current (nA) versus time while exposed to human exhalation. Though relatively small and nonuniform, the electric current signal is clearly visible as consecutive human breaths are exhaled onto the surface of the nanodevice. Each electric current pulse corresponds to a single exhalation. The electric current generated by human breath is understandably small as the bulk profile of breath molecules is nonpolar in nature and the surface coverage is lower (note that water does not generate voltages in the nanodevices described here). These results nonetheless demonstrate the potential of using molecule-induced electrical signature from biological samples or chemical species to garner energy or to sense without the need for an external power (i.e., batteryless sensors).

The relatively large voltage generation capability of the nanoconverter suggests that it may be suitable to supply nanoscale power to other nanoelectronics. Recent success in this direction has been demonstrated in a photovoltaic and a piezoelectric device, respectively. To further validate that the observed voltage signals in nanodevices described here are not due to environmental or instrumental noises, the possibility of using the nanodevice to power a carbon nanotube (CNT) field-effect transistor (FET) by connecting the two electrodes of a nanodevice to the source and drain contacts of the FET was explored.

Figure 12B:
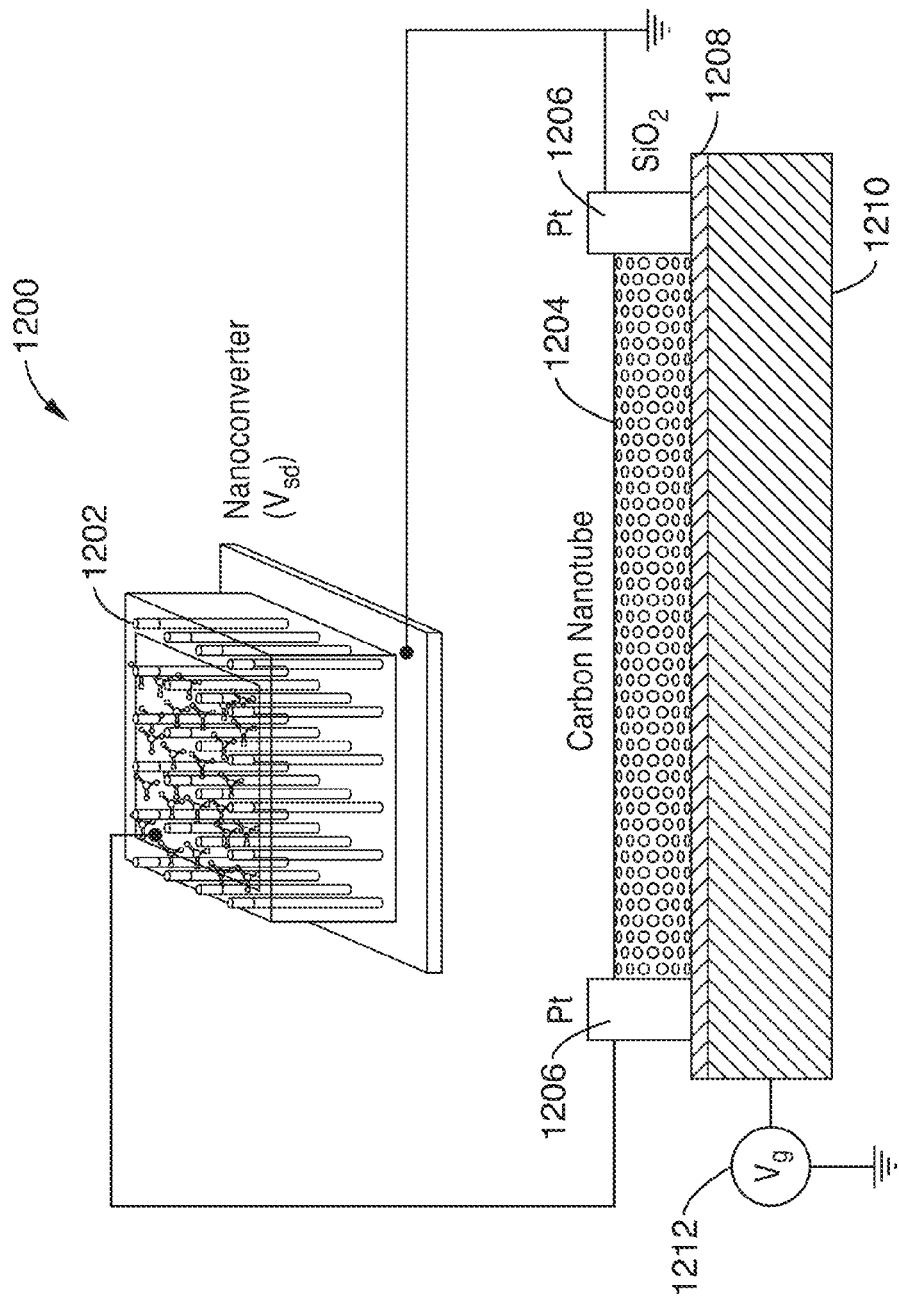
FIG. 12B is a schematic of a nanoconverter electrically connected to a carbon nanotube (CNT) at both ends by Pt contacts.

Refer now to FIG. 12B, which is a schematic 1200 of a nanoconverter 1202 electrically connected to a CNT 1204 at both ends by Pt contacts 1206. The CNT 1204 and Pt contacts 1206 are deposited upon a $SiO_2$ insulator 1208 atop a Si substrate 1210 that acts as gate to the CNT 1204 FET. The Si substrate 1210 is in turn electrically connected to a voltage source 1212 to control the CNT 1204 FET.

Figure 12C:
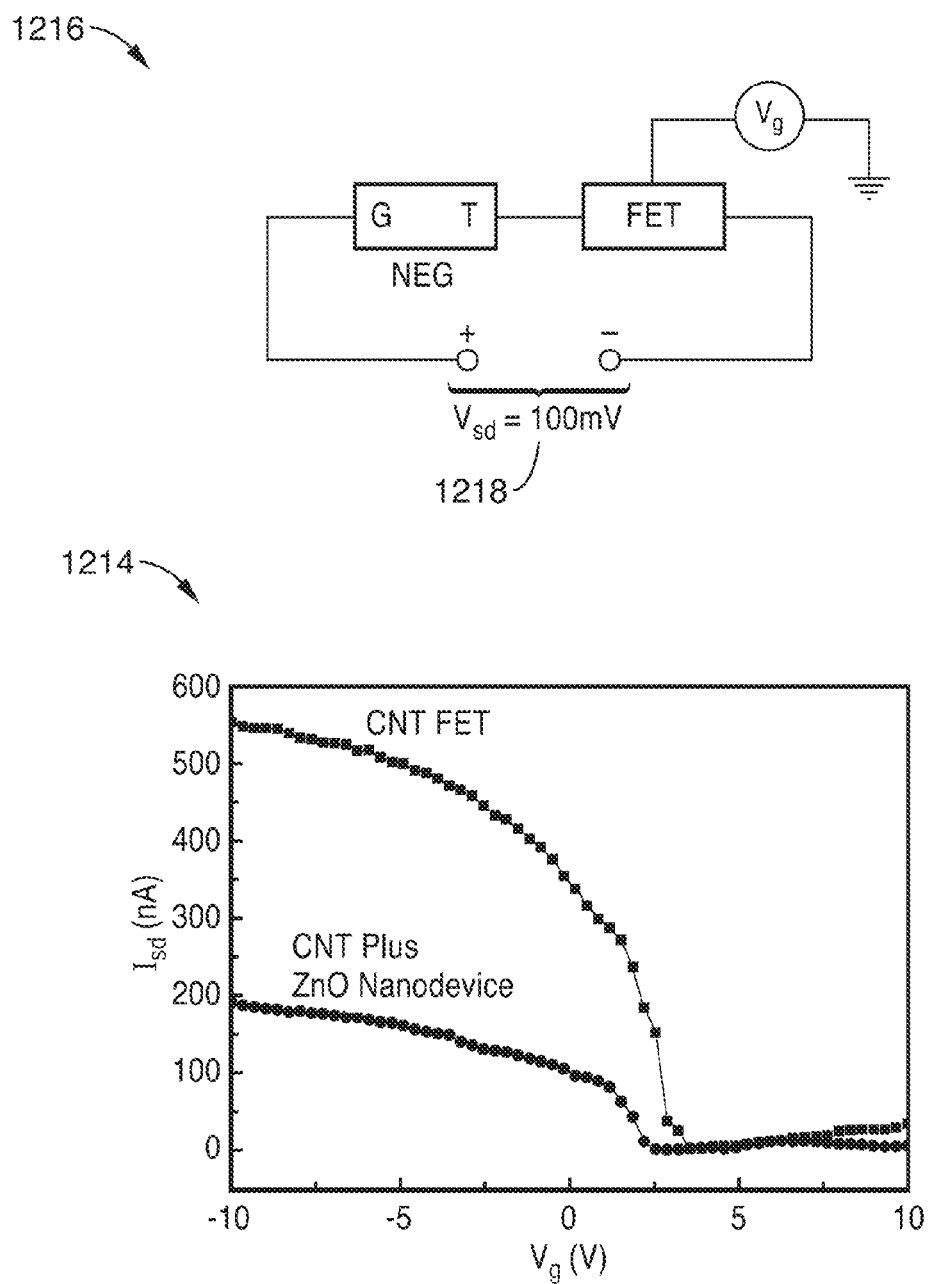
FIG. 12C is a graph of the I-V curve of the $I_{sd}$ (nA) versus $V_g$ (V) of the device embodiment of FIG. 12B with an external voltage source acting as the CNT bias source.

Refer now to FIG. 12C, which is a graph 1214 of the I-V curve of the $I_{sd}$ (nA) versus $V_g$ (V) of the device embodiment of FIG. 12B with an external voltage source acting as the CNT bias source. Above graph 1214 shows the equivalent circuit schematic 1216, where the device is driven by an external voltage source 1218 set at 100 mV.

Refer now to FIG. 12D, which is a graph 1220 of the I-V curve of the $I_{sd}$ (nA) versus $V_g$ (V) of the device embodiment of FIG. 12B with no external voltage source (as was used instead in FIG. 12C). Above graph 1220 is the equivalent circuit schematic 1222, where the ZnO nanoconverter 1224 is driven by an ethanol solvent.

Referring now to both FIGS. 12C and 12D, FIG. 12C shows the characteristic transport behavior of the FET before and after the voltage nanoconverter is connected to the circuit without solvent dripping. In this experiment, the external source-drain voltage was fixed at $V_{sd}$=100 mV and the gate voltage ($V_g$) was swept from −10 V to +10 V. The resistance of the CNT FET can be calculated at $V_g$=0 as $R_{CNT}$=294 kΩ, and the total resistance of the nanoconverter before power generation can be estimated from FIG. 12C ("CNT Plus ZnO Nanoconverter" curve) at $V_g$=0 as $R_{ZnO}$=658 kΩ.

After replacing the external power source $V_{sd}$ with the ethanol-powered nanoconverter, a transient behavior similar to the external power supply and an on-and-off ratio ($I_{on}/I_{off}$) of ~10 was observed, as shown in FIG. 12D. The power generated from the nanoconverter can be calculated as $P=I^2R$=308 pW. With an active substrate area of ~1.0 mm$^2$, and a power density of ~31 nW/cm$^2$, this nanoconverter platform could provide sufficient power to drive certain NW or nanotube-based electrical devices.

A useful aspect of the nanoconverter is that it directly utilizes the interactions between molecules and the device surface for operation, eliminating the need for external power and enabling dynamic signal generation. As most macromolecules (polysaccharides, triglycerides, polypeptides, and nucleic acids) important to living systems have relatively large dipole moments, the use of molecule-driven nanodevice in complex biological systems, for sensing or energy-conversion, is a potential embodiment.

Other Nanoconverter Chemistries

Importantly, the surface interaction mechanism reported here is applicable to other semiconducting materials. Voltage generation has been observed in vertically aligned semiconducting carbon nanotubes after exposing segments of the tubes to solvent molecules, as well as in bulk single crystal ZnO and Ge. Since the nanoconverter relies on large surface areas to function, it is not surprising that high surface-to-volume ratio nanostructures are preferred building blocks for future molecule-driven electronic systems.

Nanoconverter Fabrication Methods

Nanowire Growth

The ZnO nanowire (NW) arrays were synthesized via a carbothermal reduction process at 915° C. A 2 mm by 2 mm a-plane oriented (110) sapphire substrate (MTI Corporation) was used for epitaxial growth. After cleaning, the substrate was coated with a 2.5 nm Au layer deposited by e-beam evaporation, which acted as the catalyst for the ZnO NW growth. Equal amounts (by weight) of ZnO powder (99.99%, Alfa Aesar) and graphite powder (99.99%, Alfa Aesar) were ground together for 30 min. and loaded into an alumina boat. The substrate and the alumina boat were placed near the centre of a double quartz tube furnace, with the sapphire substrate located downstream 5-6 cm away from the ZnO/graphite powder. The flow rate of Ar was kept at a constant value of 12 standard cubic centimeters per minute (sccm). During NW growth, the mini-tube-furnace (Lindberg/Blue, Thermo Fisher Scientific) was heated to 915° C. at a ramping rate of ~50° C./min. After holding the temperature at 915° C. for 10 min., the furnace was cooled down to room temperature.

Nanodevice Fabrication and Electrical Measurements

Before infiltrating the ZnO NWs with polymer, the NW samples were examined using a field-emission SEM (JEOL JSM-7401F). The reported nanowire density was measured from a number of top-view SEM images by counting NW numbers per μm$^2$ area. A thermal plastic poly(vinyl chloride-covinyl-co-2-hydroxypropyl acrylate) (PVC) with a molecular amount of ~24,000 was dissolved in 1,4-dioxane to a concentration of 1 wt. %. The PVC solution was drop cast (25 to 40 μL of solution) onto the ZnO NW arrays to completely coat the NW tips and form a uniform film at the top surface of the nanodevice.

After infiltrated with the polymer, an oxygen plasma etching process was employed to preferentially etch away the PVC and expose the NW tips. This process was carried out on a reactive ion etching system with an operation power of 300 W and an oxygen flow rate of 90 sccm. After 3-5 minutes of etching time, the samples were examined by SEM to ensure that the NW tips were exposed. For the above described etching condition, we observed a typical NW exposure percentage of ~50-60% (i.e., ~15 NWs/μm$^2$). A 4 nm Ti/150 nm Au contact layer was deposited on the top surface by e-beam evaporation. The deposition rate was ~1 Å/s. An aluminum foil mask with a 1 mm×1 mm hole was used to ensure that the metal layer was deposited on the centre area of the substrate where NWs tend to grow more uniformly. After top-contact fabrication, one edge of the device was carefully scratched under an optical microscope until the ZnO film was exposed and silver paste was deposited as the bottom electrode. The PVC film is nonconductive and therefore acts as an insulator between the top and bottom electrodes. SEM and AFM (MFP-3D, Asylum Research) were performed to examine the surface morphology of the as-fabricated devices.

The fabrication details of the carbon nanotube field-effect transistors used here are available in the literature. The carbon nanotube we used is single-walled at 1.2 nm diameter and 5 μm long.

For electrical property measurements, a Signatone S-1160 probe station with a Keithley 2602 source meter was used. All the data presented here were obtained in an ambient environment. The experiments for driving single carbon-nanotube field-effect transistor were carried out using one-single drop of ethanol with data acquisition rate of 20 points/second. It took 6 seconds to finish one cycle of scan. Experimental environment and ethanol properties. All the solvent dripping experiments were carried out in an ambient atmosphere within a fume hood, where the temperature was measured to be 21° C. The ethanol liquid used in the experiment was purchased from SIGMA-ALDRICH (St. Louis, Mo., USA), which has a purity ≥99.5% (200 proof) and a density of 0.789 g/mL (at 20-25° C.). The vapor pressure of the ethanol at 20° C. is 44.6 mmHg. Therefore, it evaporates in ambient environment with the evaporation residue ≤0.001%. During a single drop ethanol dripping experiments, the temperatures of top and substrate sides of the devices were monitored with two separate K-type thermocouples, which indicated that the substrate temperature of the devices maintains relatively stable at 21° C., while the temperature at the top surface fluctuates slightly in the range of 21° C. to 17° C.

Randomly-Aligned Silicon Nanowire Nanosensor

Figure 13A:
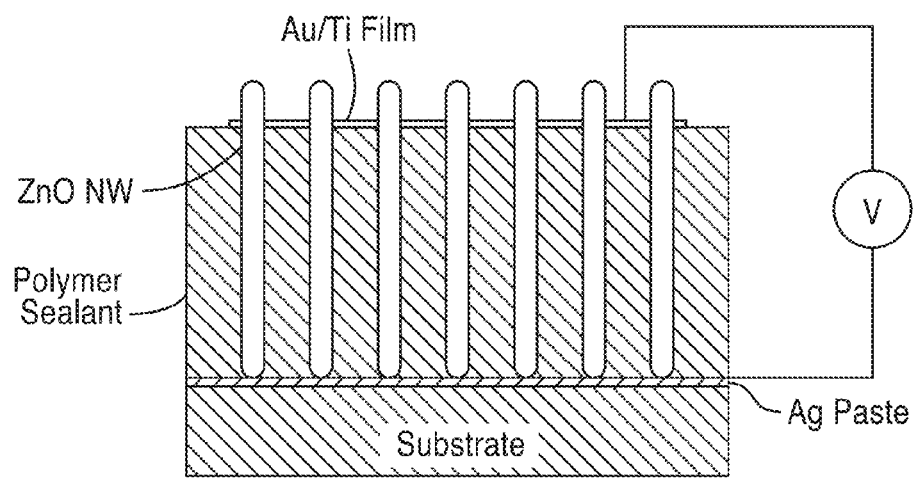
FIG. 13A is a cross section of the vertically aligned ZnO nanoconverter previously described in FIG. 3A, and is used here as a comparison geometry.
Figure 13B:
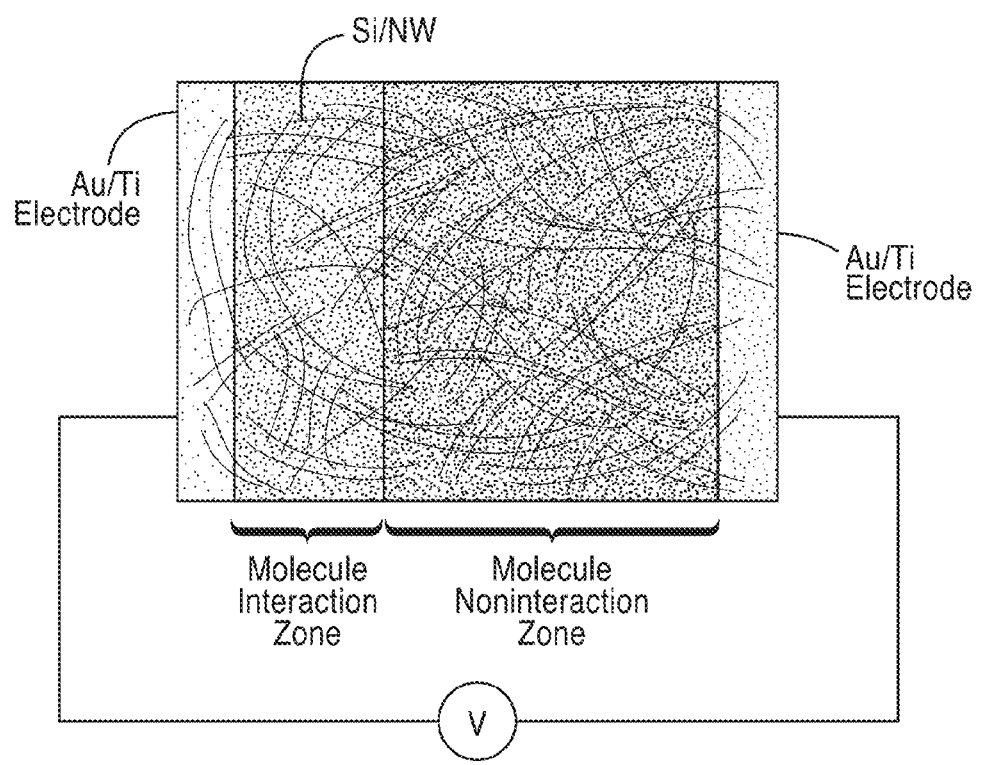
FIG. 13B is a cross section of a randomly-aligned silicon nanowire nanoconverter or nanosensor.

Refer now to FIGS. 13A-13D. FIG. 13A, which is a cross section of the vertically aligned ZnO nanoconverter that has already been described, and is used here as a comparison geometry. FIG. 13B, which is a cross section of a randomly-aligned silicon nanowire nanosensor. FIGS. 13A and 13B show the designs of two different sensing platforms, respectively. The first platform, FIG. 13A, is fabricated from the vertically-aligned single-crystalline ZnO nanowires (n-type), and the second one, FIG. 13B, utilizes randomly-aligned boron-doped silicon nanowires (p-type). ZnO and Si nanowires were chosen as they have been proven to be good sensor materials. In the first sensing platform, the tips of nanowires are exposed to chemical species and the change of the electric potential along the two ends of nanowires is monitored (FIG. 13A). In the second platform, about 80% of silicon nanowire network is sealed with insulating glue, leaving the rest of nanowires exposed to chemical species. In this platform, the potential difference between the exposed and unexposed nanowires is monitored (FIG. 13B).

Figure 13C:
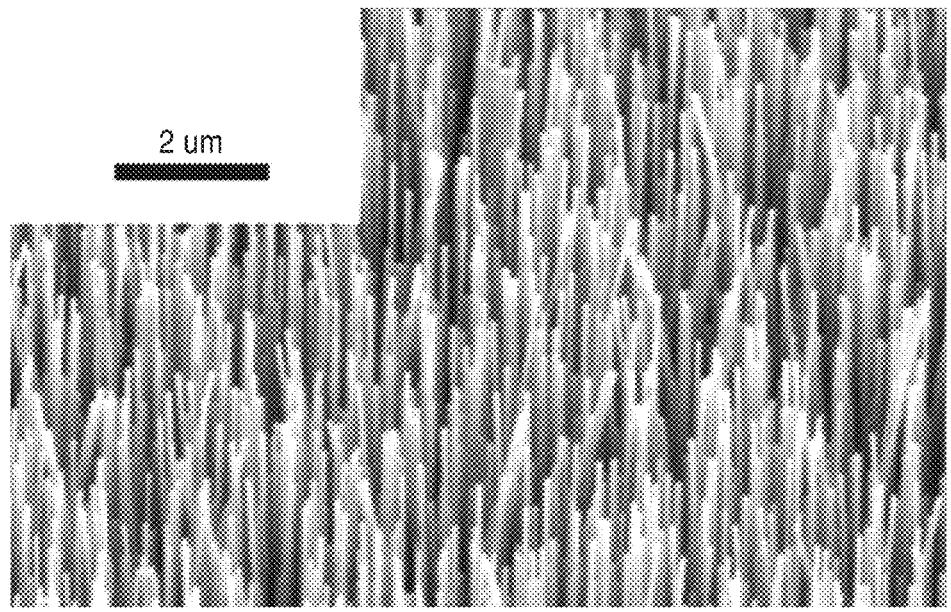
FIG. 13C is a scanning electron micrograph of the nanowire tips of the nanoconverter of FIG. 13A.

Refer now to FIG. 13C, which is a scanning electron micrograph of the nanowire tips of the nanosensor of FIG. 13A. The aligned as-grown ZnO nanowires have a length of ~6-7 µm and an areal density of ~30/µm$^2$. After growth, ZnO nanowire forest was infiltrated with a poly(vinyl chloride-co-vinyl-co-2-hydroxypropyl acrylate) (PVC) polymer and etched with oxygen plasma, leaving ~0.1-0.5 µm nanowire tips exposed. Based on the nanowire density given above, the exposed surface area of the nanowires is estimated to be 6.6 µm$^2$ per µm$^2$ device area. The carrier concentration of these as-synthesized ZnO nanowires is on the order of 5.2±2.5×10$^{17}$ cm$^{-3}$. For sensing experiments, Au/Ti (100 nm/4 nm) film and Ag paste were used to make the top and bottom electrical contacts, respectively. Standard electric current versus voltage (I-V) measurements (−0.5V~0.5V) are applied to check that good electrical contacts are made.

Figure 13D:
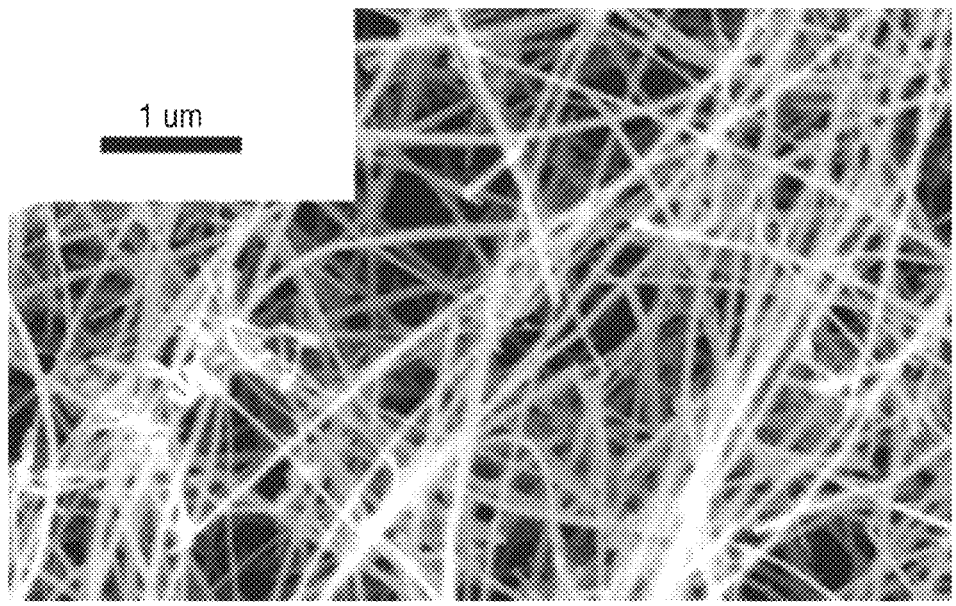
FIG. 13D is a scanning electron micrograph of the randomly oriented Si nanowires of the device of FIG. 13B.

Refer now to FIG. 13D, which is a scanning electron micrograph of the randomly oriented Si nanowires of the device of FIG. 13B. The diameters of the Si nanowires are around 30-55 nm and the lengths are up to tens of micrometers. To test the sensing property of Si nanowire interconnection network, Au (100 nm)/Ti (4 nm) film was evaporated on two opposite sides of the substrate as electrical contacts. Insulation glue was then applied to seal one side of electrode and 80% of silicon nanowire network. Again, a standard I-V scan is adopted to ensure that good electrical contacts are made on all test-bound devices.

To probe the effectiveness of ZnO nanosensor (i.e., platform one in FIG. 13A) on chemical species at room temperature, we drip a small volume (~2 µL) of ethanol (≥99.5%, SIGMA-ALDRICH, St. Louis, Mo., USA. ≥0.005% water) on the device surface and monitor the change of the electric voltage along the two ends of nanowires.

Figure 14A:
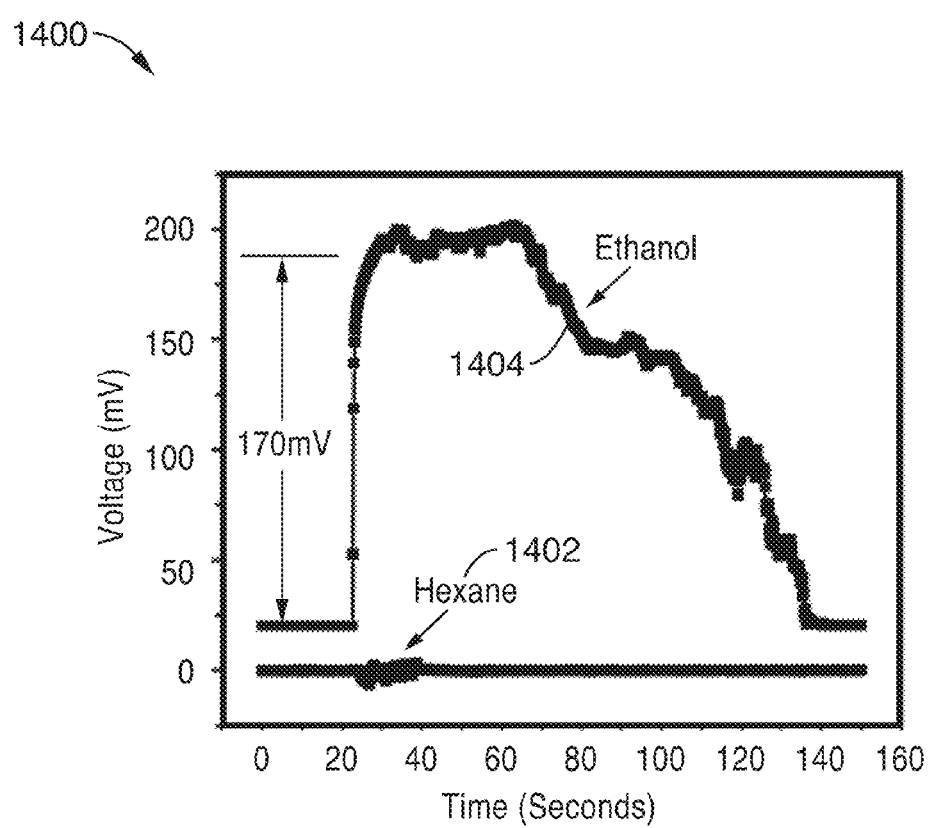
FIG. 14A is a graph of voltage vs. time for a single drop placed on the nanoconverter of FIG. 13A, where the drops are pure hexane in one instance, and pure ethanol in the second instance.

Refer now to FIG. 14A, which is a graph 1400 of voltage vs. time for a single drop placed on the nanosensor of FIG. 13A, where the drops are pure hexane 1402 in one instance, and pure ethanol 1404 in the second instance. A sharp rise of an electric voltage with the peak value on the order of ~170 mV is observed. The rise of the electric signal is almost instantaneous but decays slowly to zero level as the ethanol solvent evaporates. This result indicates that the chemical sensor made of ZnO nanowires is recoverable. Interestingly, little electric voltage is observed when a small amount of hexane solvent (≥99.0%, SIGMA-ALDRICH, St. Louis, Mo., USA. ≤0.001% water) is dripped onto the surface of the same device, suggesting that the nanosensor selectively responds to different types of solvent molecules. These experiments, together with measurements using more than 15 different types of organic solvents (e.g., hexane, acetone, benzene, chloroform, toluene, 1,4 Dioxane, n-butanol, 1-propanol, pyridine, N,N-dimethylacetamide, and dimethyl sulfoxide), strongly suggest that the magnitude of the peak voltage scales sensitively on the dipole moment (µ) and surface coverage of the tested solvents, with non-polar solvents such as hexane and benzene generating essentially zero electric voltage. Thus, dipole containing organic molecules are examples of molecules that: 1) cause power generation employing the subject invention; and 2) may be detected utilizing the subject invention. Additionally, this trait makes it possible for these nanosensors to detect different types of chemical species and their concentration levels. The preferred molecules are dipole containing organic molecules. Specifically, the dipole containing organic molecule may be selected from a group consisting of: alcohols, amines, amides, carboxylic acids, esters, furans, pyridines, aldehydes, ketones, sulfoxides, carbohydrates, and similar and/or equivalent dipole containing species of detectable formulation and configuration.

It is noteworthy to point out that, unlike other types of high dipole moment molecules, de-ionized water (µ=1.85 D) produces little voltage signal in the tested nanodevices. This is likely due to the fact that the surface tension of water (71.99 nN/m) is more than three times higher than that of ethanol (21.97 nN/m), leading to poor surface wetability in our nanodevices. The negligible voltage signal observed by water eliminates the possibility of water (in the air or in some solvents) contamination/contribution to the nanosensors described here.

Figure 14B:
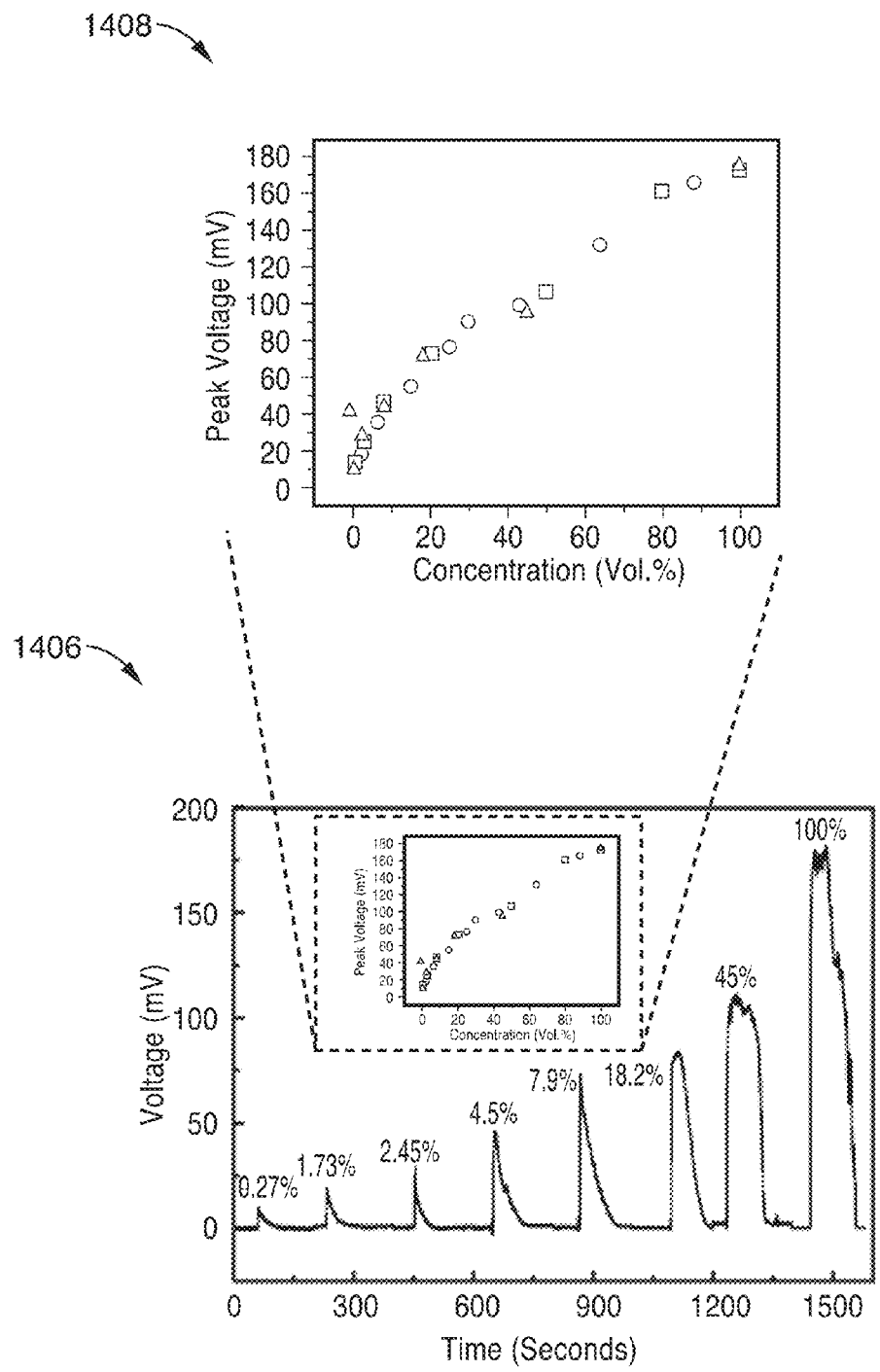
FIG. 14B is a graph of voltage vs. time for the ZnO nanosensor of FIG. 13A, with different concentrations of ethanol in hexane.

Refer now to FIG. 14B, which is a graph 1406 of voltage vs. time for the ZnO nanosensor of FIG. 13A, with different concentrations of ethanol in hexane. The sensing ability of the ZnO nanosensor platform to small concentrations of ethanol solvent is shown as different percentages of ethanol with hexane are mixed (note that hexane does not generate voltage signal in our device) and dripped onto the surface of the ZnO nanosensor. The dripping volume is fixed at ~2.2 µL per drop. The voltage measurement results demonstrate that the induced peak electric voltage increases stepwise with the concentrations of ethanol solvent, and that the voltage signal is reversible for decreasing or increasing ethanol concentrations. The lowest concentration level tested so far using ZnO nanowire platform is 0.27 vol. %, which yields a peak voltage signal of 11.7 mV. A higher detection limit is possible as the electric probe station has a voltage resolution better than one tenth of mV (~50 µV, equivalent to 10 ppm ethanol concentration level).

To establish the reproducibility, three independent measurements were carried out on one single device, as displayed in the inset 1408 of FIG. 14B, showing that the concentration dependence of the voltage signal is slightly non-linear. This non-linearity was observed in all five good devices tested. There are two possible reasons that could have contributed to this behavior. First, the vertically-aligned ZnO nanowires have different exposure heights (~0.1-0.5 µm), which may lead to different magnitudes of voltage signals for each individual nanowire and collectively contribute to the overall output voltage. Second, the observed nonlinear response may also suggest that the change of the electron affinity of ZnO nanowires after molecular adsorption is non-linear, as it could have a complex dependence behavior on surface coverage, molecular size, dipole moment, and surface tension of the solvents. It was found that, independent of the ethanol concentration levels, the recovery time of the nanosensor is relatively short (<100 s). The fast recoverable time of the nanosensor is due to the volatile nature of ethanol and hexane in ambient atmosphere, and is advantageous over other nanowire-based sensors that, because of large surface-to-volume ratios, often have a much longer recovery time.

Refer back to FIGS. 13A and 13B. It is noted that in both platforms, the tested solvents also wet one metal contact on each of the nanodevices. It is known that the electrochemical potential of metal contact can be shifted once immersed into liquid solutions/solvents. Therefore, additional experiments were carried out to quantify the accuracy of the electrochemical potential shift using devices without nanowire protrusions, as well as a device fabricated from single-crystal ZnO. In both cases when ethanol solvent was used, a voltage signal was observed on the order of ~1 mV, consistent with the results reported by Ghosh et al. on carbon-nanotube metal interfaces, and supports the suggestion that the active functioning ingredients in the nanosensors here are semiconducting nanowires rather than the metal contacts.

Figure 14C:
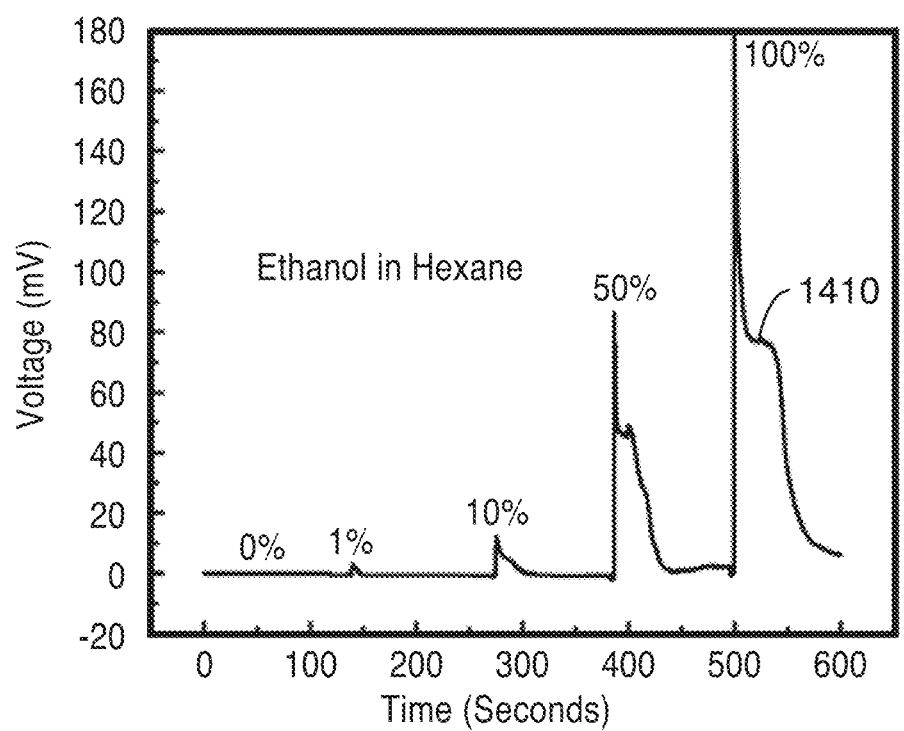
FIG. 14C is a plot of electric voltage of the silicon nanowire device of FIG. 13B in response to different concentrations of ethanol solvent in hexane.

Refer now to FIG. 14C, which is a plot of electric voltage of the silicon nanowire device of FIG. 13B in response to different concentrations of ethanol solvent. A similar decreasing trend is observed in this device with decreasing ethanol concentrations. Furthermore, it was found that the decay shape of the electric voltage as a function of time was drastically different from that of ZnO nanowire sensors, possibly due to the change of the wetting area difference between ZnO and silicon nanowire devices. The irregular decay shape of voltage signal 1410 in the silicon nanowire device is currently not well-understood and requires further investigation. Nevertheless, these results demonstrate that it is possible to extend a batteryless sensing platform to randomly-aligned semiconductor nanowire systems.

Figure 15B:
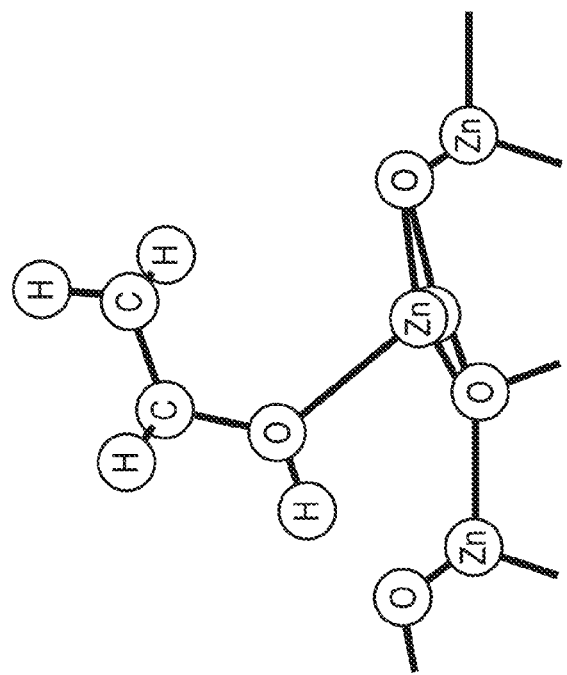
FIG. 15B is a rendered output of a DFT calculation, indicating that under the minimum energy configuration condition, the adsorption of ethanol onto ZnO surfaces is characterized by the formation of a chemical bond between the O-atom in ethanol and a Zn-atom, as well as a hydrogen bridging bond between an H-atom and an O-atom in ZnO.
Figure 15A:
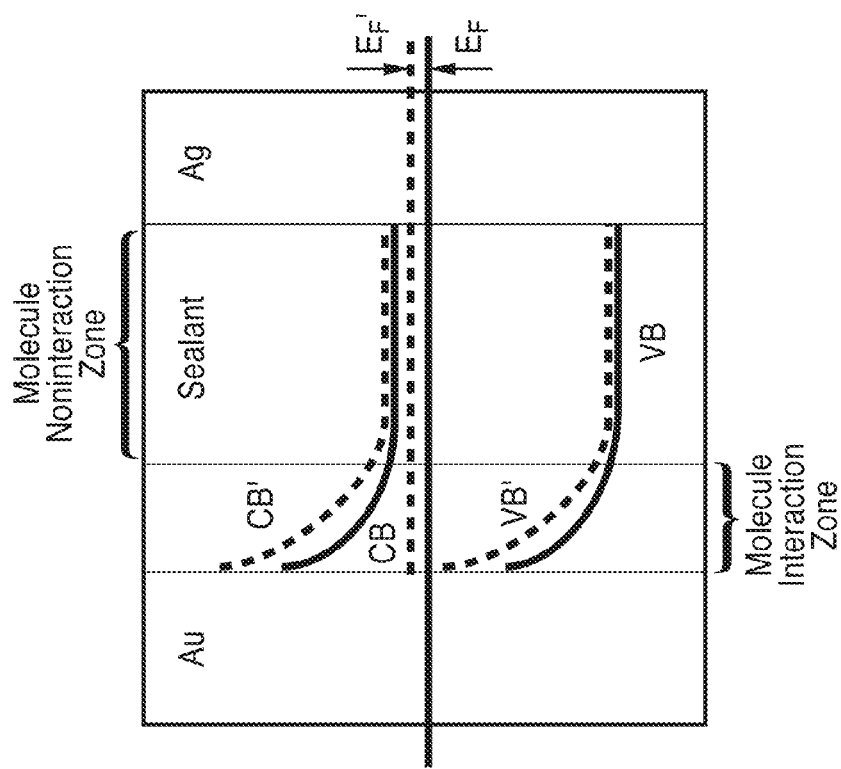
FIG. 15A is a qualitative energy-band diagram of the nanosensors described herein.

Refer now to FIG. 15A, which is a qualitative energy-band diagram of the nanosensors described herein. The working principle of the nanosensors relies on partial exposure of semiconducting nanowires to target chemical species and a non-ohmic contact that is necessary for the nanosensors to function. The Fermi level, conduction band, and valence band of the devices before chemical exposure are denoted as $E_F$, CB, and VB, respectively. Note that there exists a non-ohmic contact and band bending (upwards bending for ZnO, and downwards bending for Si) in both devices. Upon adsorption of molecules (such as ethanol), it is known that the carrier density (electrons for n-type ZnO nanowires, and holes for p-type Si nanowires) of the exposed nanowire segment is altered, leading to profile modification of CB to CB'. This process metastably tilts the Fermi level of nanowires from EF to EF', and renders a detectable potential offset between the top (Au) and ground (Ag) contacts. The thermodynamic re-equilibration of the Fermi level will require electron drift/diffusion through the non-ohmic contact or through a discharge process by short-circuiting the top and ground contacts. This qualitative picture suggests that the magnitude and shape of the voltage signals observed here are closely tied to the electron donating/withdrawing ability of molecules (as well as their other physical properties), the nature of the non-ohmic contact (which can be modified by molecules), and the charge carrier density (electrons or holes) within the nanowires. In the case of an ohmic top contact or near metallic nanowires (for example, highly-doped Si nanowires), appreciable voltage signals from ethanol solvent was not seen, which is in accord with the above hypotheses.

To quantitatively understand the physical origin/mechanism of the nanosensors described herein, quantum mechanical calculations were further carried out using density functional theory (DFT). For simplicity, the calculations focus on the chemisorptions effect (using ethanol molecule as prototype study) on the electron affinity ($\chi$) and work function ($\phi$) of semiconducting ZnO nanowires. The results indicate that ethanol molecule has a negative adsorption energy when it interacts with ZnO nanowire top ((0001) or (000$\bar{1}$)) or side (10$\bar{1}$0) surfaces. This negative adsorption energy is the main driving force that allows ethanol molecules to be adsorbed.

Refer now to FIG. 15B, which indicates that under the minimum energy configuration condition, the adsorption of ethanol onto ZnO surfaces is characterized by the formation of a chemical bond between the O-atom in ethanol and a Zn-atom, as well as a hydrogen bridging bond between an H-atom and an O-atom in ZnO.

Figure 15C:
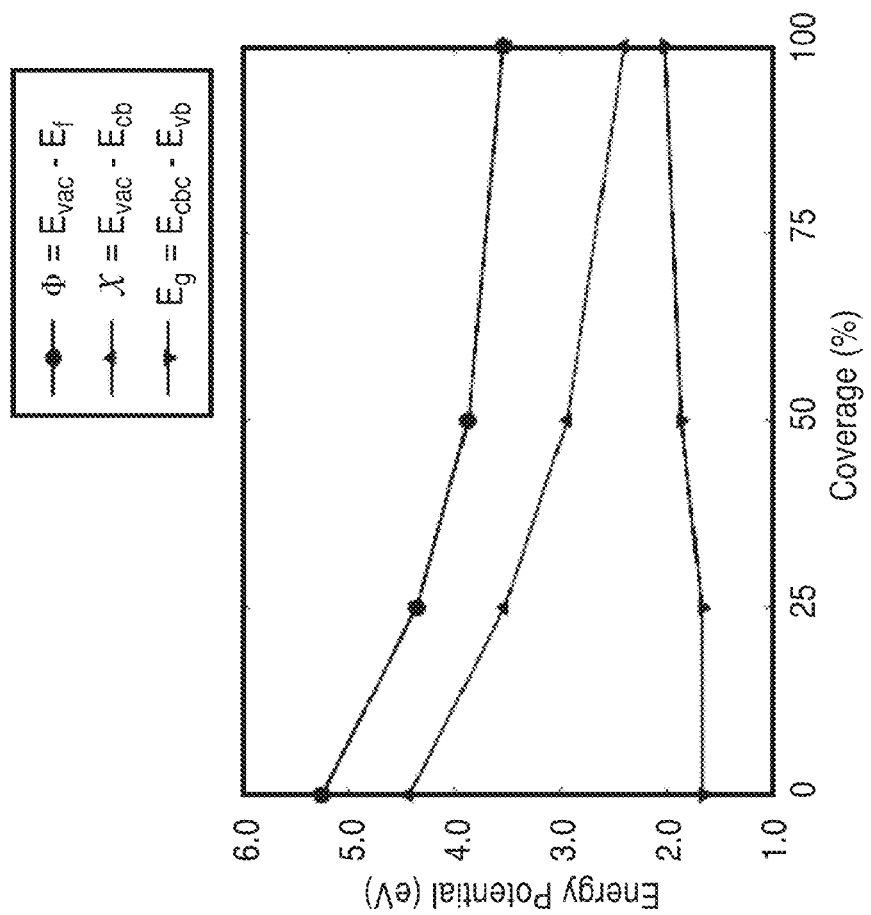
FIG. 15C is a graph of Energy/Potential in eV vs. percentage of coverage.

Refer now to FIG. 15C, which is a graph of Energy/Potential in eV vs. percentage of coverage. After adsorption, it was found that the electron affinity $\chi$, as well as the work function $\phi$, of ZnO nanowires in contact with ethanol molecules was substantially altered. The change of the electron affinity scales approximately with the surface coverage, but shows a non-linear behavior that qualitatively agrees with our experimental observations. Under the minimum energy interaction configurations, FIG. 15C indicates that the absolute value of electron affinity $\chi$ of clean ZnO surface decreases from 4.5 eV to 2.4 eV when the surface coverage of ethanol increases from 0 to 100%, whereas the band gap remains fairly constant. It is noted that the electron affinity changes from these calculations are about one order of magnitude higher than those that were measured from experiments, possibly due to the reasons that (1) the calculations used clean ZnO surfaces such that their interactions with molecules are stronger, and (2) the change of the electron affinity may not completely reflect on the measured potentials, as the thermodynamic re-equilibration process tends to reduce the potentials. Nonetheless, the change of the electron affinity of ZnO when exposed to ethanol solvents is consistent with the qualitative picture depicted in FIG. 15C and appears to be the main reason that leads to the large electric potential difference between the two contacts of ZnO nanowires. In addition to the surface coverage, the calculations here also revealed that the dipole moment of the solvent molecules and its orientations relevant to the ZnO surfaces have direct impacts on the magnitude of the electron affinity change. Since different organic molecules have different dipole moments, this characteristic makes our nanosensors promising to detect different types of chemical- or bio-molecules.

In summary, two different types of batteryless sensing platforms have been demonstrated at room temperature using either vertically-aligned ZnO or randomly-aligned silicon nanowires. Unlike traditional chemical or biological sensors, the sensing platforms described herein rely on the changes of charge carriers that induce electric potentials along nanowires or between different nanowires when exposed to chemical species. Since these nanosensors do not hinge on equilibrium thermodynamic variables, they have fast response time (better than 1 s), relatively high sensitivity, and more importantly, do not require external power sources. As such, the power-consumption of these nanosensors is no longer a major concern. Since most organic molecules in living systems have a tangible dipole moment, it is expected that the chemical sensor reported here is also applicable to biological systems.

Experimental and Modeling

The vertically-aligned ZnO nanowires with the diameter in the range of 60-120 nm were grown on an a-plane sapphire substrate using a chemical vapor transport and condensation (CVTC) process. The growth temperature and time are 915-930° C. and 3-5 min., respectively. After growth, the ZnO nanowire forest was filled with poly(vinyl chloride-co-vinyl-co-2-hydroxypropyl acrylate) (PVC), which is cured at room temperature for 24 hours. An oxygen plasma etching process was employed to preferentially etch away the PVC and expose the NW tips. This process was carried out on a reactive ion etching system with an operation power of 300 W and an oxygen flow rate of 90 standard cubic centimeters per minute (sccm). The etching time is 3-5 minutes. The top metal contact of ZnO nanosensor was deposited by e-beam evaporation, and the bottom contact was prepared by applying the silver paste.

Randomly-aligned Si nanowires were fabricated using a vapor-liquid-solid (VLS) process. The Si nanowires were grown on 2 mm×4 mm <111> Si substrate covered with 250 nm native oxide layer. Gold nanoparticles (Ted Pella, Inc.) with an average diameter of 30 nm were used as the catalyst. $SiH_4$ (Voltaix, Inc.) was used as the precursor and $B_2H_6$ (Voltaix, Inc.) as a dopant. The ratio of $SiH_4$ to $B_2H_6$ was set to 4000:1. The nanowires were grown at 420° C.-460° C. for 30 minutes. Both contacts of the Si nanowire device were prepared by e-beam evaporation. All the electrical measurements were carried out using a Keithley 2602 System Source Meter with a custom-built Labview controlling program.

To model the interactions between the ethanol and the clean ZnO surface, the quantum mechanical calculations were carried out within the framework of density functional theory in the generalized gradient approximation (GGA) using the Vienna ab-initio simulation package. The atomic cores were replaced by pseudopotentials in the projector augmented wave formalism, and the Zn-3d electrons were treated as valence electrons. As the band gap of ZnO is treated poorly by the GGA, we also applied the GGA+U method by Dudarev et al. with U-J=7 eV. The occupation numbers where determined using a Gaussian smearing of 0.1 eV. For the bulk this yielded the lattice parameters a=3.196 Å and c=5.132 Å, together with the internal parameter u=0.381. Slab models were created from 16 atomic and 16 vacuum layers along the [10$\bar{1}$0] direction. For these systems the Brillouin zone was sampled using a 2×2×1 Monkhorst-Pack sampling for a cell with 2×2 cross section. Structures were converged until the forces were below 30 meV/Å.

Randomly Aligned Silicon Nanowire Nanodevice or Nanosensor Implementations

Figure 16A:
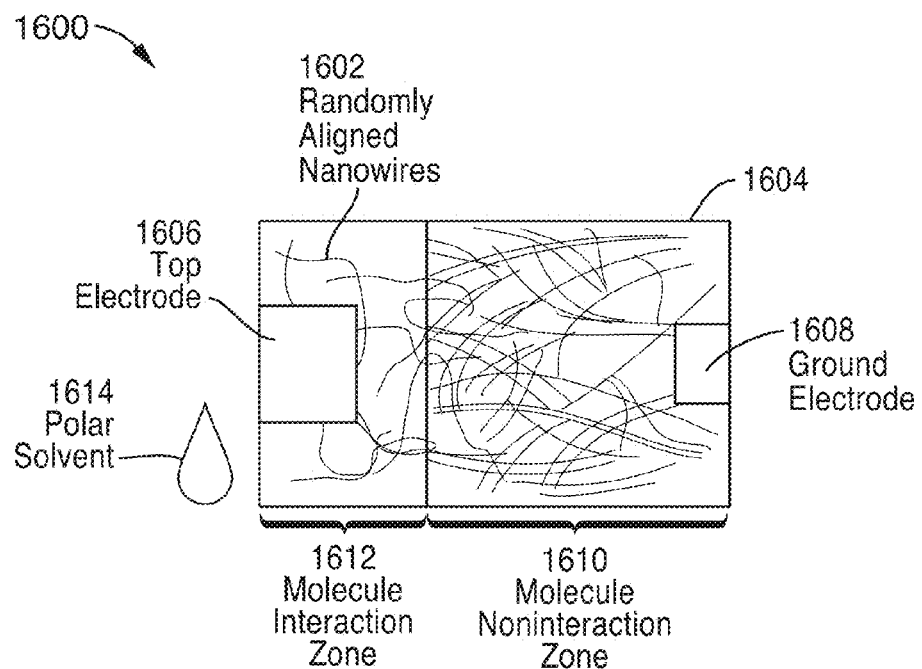
FIG. 16A is a top view of a randomly aligned silicon nanowire nanoconverter or nanosensor.
Figure 16B:
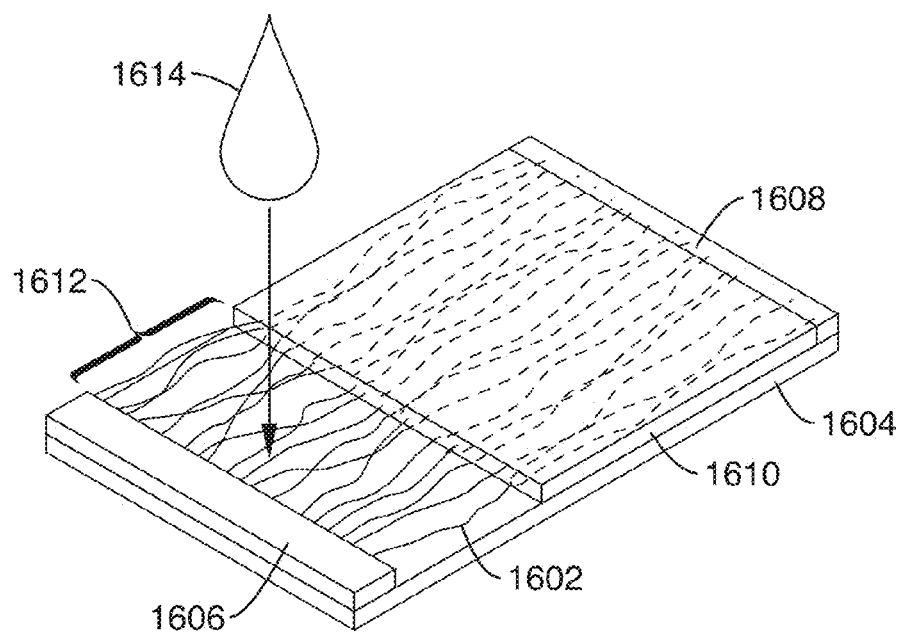
FIG. 16B is a perspective view of the same device as FIG. 16A with minor electrode geometry modifications.

Refer now to FIGS. 16A and 16B. FIG. 16A is a top view of a randomly aligned silicon nanowire nanodevice or nanosensor 1600. FIG. 16B is a perspective view of the same device as FIG. 16A with minor electrode geometry modifications.

The nanodevice is designated generally by the reference numeral 1600. In this approach, randomly-aligned silicon nanowires 1602 are fabricated through a chemical vapor deposition process. These silicon nanowires 1602 form an interconnected nanowire network on the substrate 1604. After nanowire growth, a top electrode 1606 and a ground electrode 1608, which are in contact with nanowires 1602, are constructed on one side of the substrate 1604. Then part of the randomly-aligned nanowire network is sealed with epoxy 1610 (to form a molecule noninteraction zone), leaving another unsealed section 1612 (to form a molecule interaction zone) of the nanowire area that can be exposed to molecules in a molecule interaction zone. Electric voltage and current is generated when polar solvents 1614 are dripped onto the unsealed section 1612. This device can also be used for batteryless sensing purpose, i.e., a new type of sensors without the need for external driven powers. The nanodevice 1600 is applicable to other types of semiconductor nanowires that are grown randomly on the substrate.

Arrays of Individual Nanoconverters

Figure 17:
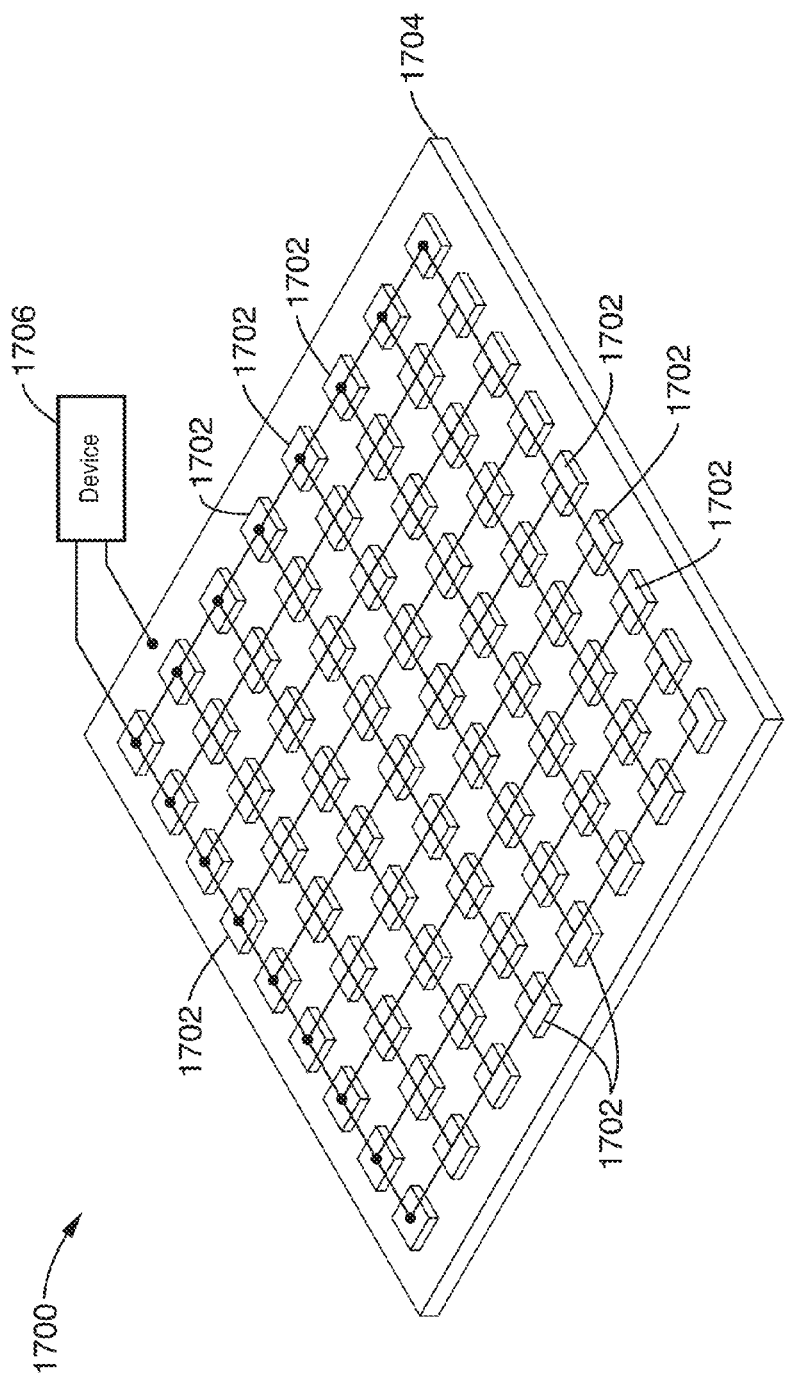
FIG. 17 is a perspective view of an array of individual nanoconverters arranged on a substrate.

Refer now to FIG. 17, which is a perspective view 1700 of an array of individual nanoconverters 1702 shown arranged on a substrate 1704. The individual nanoconverters 1702 are shown arranged on a substrate 1704. The individual nanoconverters 1702 are electrically connected as required in series and parallel to provide increased voltage and current to power an external device 1706. The array 1700 shown in FIG. 17 consists of sixty four nanoconverters 1702. The number of nanoconverters can be adjusted for the amount of power required to run a specific device 1706.

Nanoconverters Generating Electricity From Molecules

Refer now to FIG. 18, which is an array 1800 of individual nanoconverters 1802 arranged on a substrate 1804 that will directly generate electricity through interactions with molecules 1806. The array 1800 and individual nanoconverters 1802 are exposed to molecules 1806. The exposure of the nanowires or nanotubes (not shown in this drawing) in the nanoconverters 1802 to molecules 1806 allows the nanoconverters 1802 to generate an electric current. The molecules contain chemical energy. When interacting with certain types of materials, these molecules can either be decomposed (through catalytic activities) or directly interact with semiconductor surfaces through charge-transfer or dipole-interactions. The array 1800 of nanoconverters 1802 is connected by electrical leads 1806 and 1808 to an external device (not shown) that will be powered by the nanoconverters 1802.

Figure 18A:
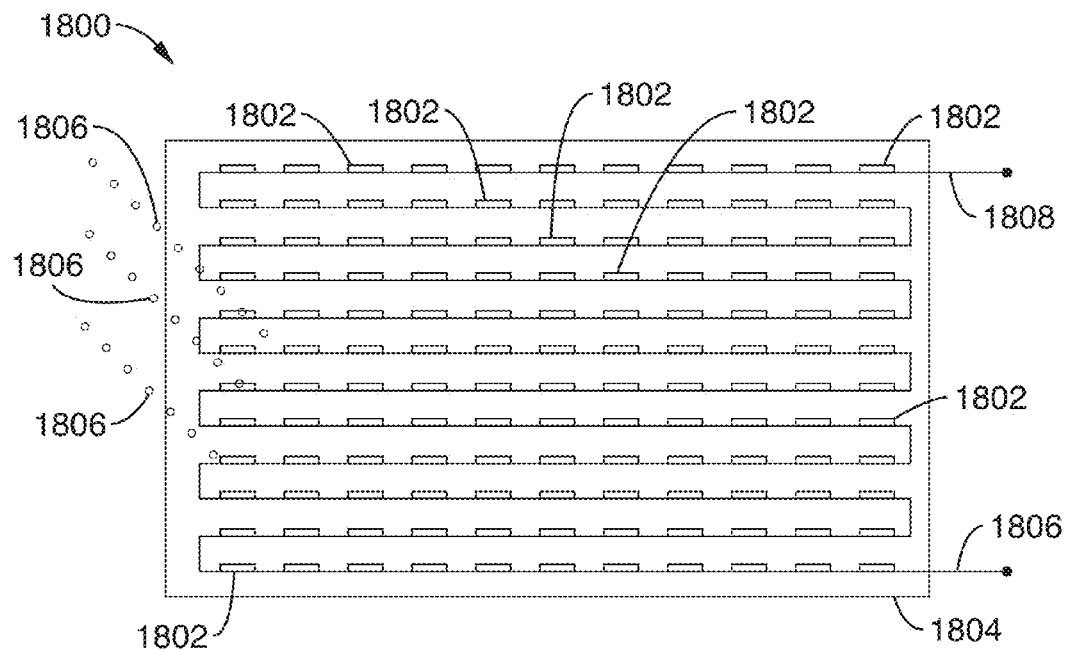
FIG. 18A is a perspective view of an array of individual nanoconverters that will directly generate electricity through interactions with molecules.
Figure 18B:
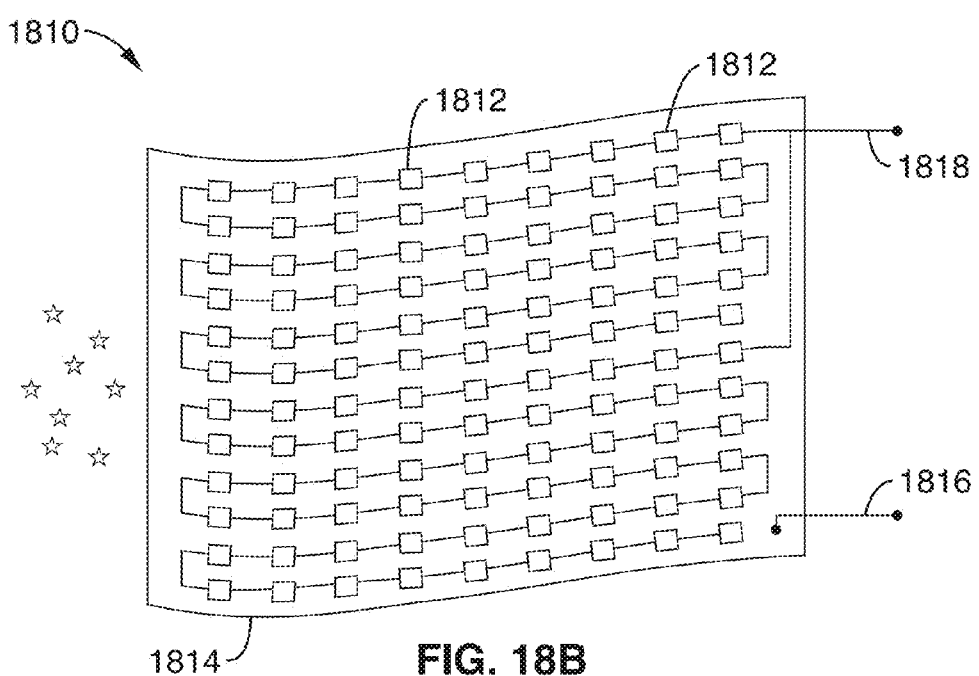
FIG. 18B is a perspective view of an array of nanoconverters somewhat similar to the one previously described in FIG. 18A, but with a flexible substrate, and arranged in a series parallel fashion to achieve increased voltage and current outputs.

Refer now to FIG. 18B, which is a perspective view of an array 1810 of nanoconverters 1812 somewhat similar to the one previously described in FIG. 18A, but with a flexible substrate 1814, and arranged in a series parallel fashion to achieve increased voltage and current outputs at power output leads 1816 and 1818.

With the advent of a flexible substrate, nanoconverter arrays may be stacked to form a three dimensional lattice for increased power supply. Alternatively, the substrates may be rolled into rolls, while still allowing input of solvent molecules, and minimizing volume.

From the discussion above it will be appreciated that the invention can be embodied in various ways, including but not limited to the following:

1. A nanoconverter, comprising: one or more nanostructures; and means for generating power from the one or more nanostructures.

2. The nanoconverter of embodiment 1, wherein the means for generating power comprises: a molecule interaction zone wherein the nanostructures are capable of interaction with molecules.

3. The nanoconverter of embodiment 2, wherein the means for generating power further comprises: a molecule non interaction zone wherein the nanostructures are incapable of interaction with molecules.

4. The nanoconverter of embodiment 1, wherein the nanostructures are selected from a group consisting of: a nanotube, a nanowire, a nanosheet, and a nanoribbon.

5. The nanoconverter of embodiment 1, wherein the nanostructures are selected from a group consisting of: a ZnO nanowire, a silicon nanowire, a carbon nanotube, and a semiconductor nanostructure.

6. The nanoconverter of embodiment 1, wherein the nanostructures are aligned or randomly aligned.

7. The nanoconverter of embodiment 1, wherein the means for generating power comprises: an interaction of the nanostructures with a molecule in a molecule interaction zone.

8. The nanoconverter of embodiment 7, wherein the molecule originates from a source selected from a group consisting of: an exhalation, a gas, and a liquid.

9. The nanoconverter of embodiment 8, wherein the exhalation originates from a source selected from a group consisting of: human breath, non-human animal breath, bacterial outgas, and plant outgas.

10. An array of one or more nanoconverters of embodiment 1 that forms a nanoconverter array, arranged to generate a specified current and voltage output when supplied with a molecule.

11. The array of embodiment 10, wherein the molecule is a dipole containing organic species.

12. The array of embodiment 10, wherein the molecule is selected from a group of dipole containing organic species consisting of: alcohols, amines, amides, carboxylic acids, esters, furans, pyridines, aldehydes, ketones, sulfoxides, carbohydrates, and similar or equivalent dipole containing species.

13. The array of embodiment 10, wherein the molecule is selected from a group of molecules consisting of: methanol, ethanol, toluene, trichoromethane, n-butanol, 1-propanol, 1-octanol, tetrahydrofuran, pyridine, acetone, N,N-dimethyacetamide, N,N-dimethyformamide, dimethyl sulfoxide, glucose, and their combinations.

14. The array of embodiment 10, wherein the nanoconverter operates as a nanosensor to detect molecules by generation of a voltage.

15. The array of embodiment 14, further comprising a membrane permeable to the molecule that surrounds the molecule interaction zone.

16. The array of embodiment 10, wherein the means for generating power generates output power for one or more devices selected from a group consisting of: a cell phone, a smart phone, a glucose monitor, a pacemaker, a therapeutic or diagnostic device, a drug delivery device, an insulin pump, a left ventricular assist device, a pacemaker, a cardioverter defibrillator, or a artificial muscle device, a cochlear implant, a batteryless device, a powered nanomachine, and an artificial vision device.

17. The array of embodiment 10, wherein the means for generating power generates output power for an insulin control system, the insulin control system comprising: a nanosensor glucose monitor that produces a voltage proportional to a glucose molecule concentration; a controller that senses the nanosensor glucose monitor voltage; and an insulin pump controlled by the controller whereby insulin is disseminated when the nanosensor glucose monitor voltage is exceeded.

18. The nanoconverter of embodiment 3, wherein the molecule non interaction zone is permeated by a sealant selected from the group of sealants consisting of: epoxy, and poly (vinyl chloride-co-vinyl-co-2-hydroxypropyl acrylate) (PVC) polymer.

19. The nanoconverter of embodiment 3, further comprising: an electrode that electrically connects to the nanostructure in the molecule interaction zone; and an electrode that electrically connects to the nanostructure in the molecule noninteraction zone.

20. A nanoconverter apparatus, comprising: a nanostructure with first and second ends; an electrode electrically connected to the nanostructure proximal to a molecule interaction zone at the first end of the nanostructure; a sealant matrix that surrounds at least a portion of the nanostructure, wherein the surrounded portion of the nanostructure forms a molecule noninteraction zone; and an electrode electrically connected to the nanostructure proximal to the molecule noninteraction zone at the second end of the nanostructure; wherein the nanostructure generates a voltage and a current when the molecule interaction zone interacts with a molecule.

21. The apparatus of embodiment 20, wherein within the molecule noninteraction zone the nanostructures are incapable of interaction with molecules.

22. The apparatus of embodiment 20, wherein the nanostructure is selected from a group consisting of: a nanotube, a nanowire, a nanosheet, and a nanoribbon.

23. The apparatus of embodiment 20, wherein the nanostructure is selected from a group consisting of: a ZnO nanowire, a silicon nanowire, a carbon nanotube, and a semiconductor nanostructure.

24. The apparatus of embodiment 20, wherein the nanostructure is an element of an aligned or randomly aligned forest of nanostructures.

25. The apparatus of embodiment 20, wherein the nanostructure generates the voltage and the current through physisorption of the molecule onto the nanostructure.

26. The apparatus of embodiment 20, wherein the molecule originates from a source selected from a group consisting of: an exhalation, a gas, and a liquid.

27. The apparatus of embodiment 26, wherein the exhalation originates from a source selected from a group consisting of: human breath, non-human animal breath, bacterial outgas, and plant outgas.

28. The apparatus of embodiment 20, wherein the molecule noninteraction zone sealant matrix is permeated by a sealant selected from the group of sealants consisting of: epoxy, and poly(vinyl chloride-co-vinyl-co-2-hydroxypropyl acrylate) (PVC) polymer.

29. A nanoconverter array, comprising: an array of one or more nanoconverters of embodiment 20; wherein the nanoconverters are arranged to generate a specified current output and voltage output when supplied with the molecule.

30. The array of embodiment 29, wherein the molecule is a dipole containing organic species.

31. The array of embodiment 29, wherein the molecule is selected from a group of dipole containing organic species consisting of: alcohols, amines, amides, carboxylic acids, esters, furans, pyridines, aldehydes, ketones, sulfoxides, carbohydrates, and similar and/or equivalent dipole containing species.

32. The array of embodiment 29, wherein the molecule is selected from a group of molecules consisting of: methanol, ethanol, toluene, trichoromethane, n-butanol, 1-propanol, 1-octanol, tetrahydrofuran, pyridine, acetone, N,N-dimethyacetamide, N,N-dimethyformamide, dimethyl sulfoxide, glucose, and their combinations.

33. The array of embodiment 29, wherein the molecule is substantially polar.

34. The array of embodiment 29, wherein the nanoconverter operates as a nanosensor to detect molecules by generation of the voltage output.

35. The array of embodiment 34, further comprising: a permeable membrane to the molecule that surrounds the molecule interaction zone; wherein the permeable membrane preferentially allows transmission of a specific molecule.

36. The array of embodiment 29, wherein the nanostructure generated voltage and current outputs power for one or more devices selected from the group consisting of: a cell phone, a smart phone, a glucose monitor, a pacemaker, a therapeutic or diagnostic device, a drug delivery device, an insulin pump, a left ventricular assist device, a pacemaker, a cardioverter defibrillator, or a artificial muscle device, a cochlear implant, a batteryless device, a powered nanomachine, and an artificial vision device.

37. The array of embodiment 29, wherein the nanostructure generated voltage output and current output powers an insulin control system, the insulin control system comprising:

a nanosensor glucose monitor that produces a voltage proportional to a glucose molecule concentration; a controller that senses the nanosensor glucose monitor voltage; and an insulin pump controlled by the controller whereby insulin is disseminated when the nanosensor glucose monitor voltage is exceeded.

38. A method of constructing a nanoconverter, comprising: providing a substrate; growing one or more nanostructures on the substrate; permeating the nanostructures with a sealant to form a molecule noninteraction zone around the nanostructures; selectively etching the molecule noninteraction zone around the nanostructures to form a molecule interaction zone; and electrically connecting the nanostructures at two ends, wherein the two end have disposed between them the molecule interaction zone and the molecule noninteraction zone.

39. The method of embodiment 38, further comprising: exposing the molecule interaction zone to one or more molecules, thereby generating electrical power.

40. The method of embodiment 38, wherein within the molecule noninteraction zone the nanostructures are substantially incapable of interaction with molecules.

41. The method of embodiment 38, wherein the nanostructures are selected from a group consisting of: a nanotube, a nanowire, a nanosheet, and a nanoribbon.

42. The method of embodiment 38, wherein the nanostructures are selected from a group consisting of: a ZnO nanowire, a silicon nanowire, a carbon nanotube, and a semiconductor nanostructure.

43. The method of embodiment 42, wherein the nanostructures are aligned or randomly aligned.

44. The method of embodiment 38, wherein the nanostructures generate the electrical power through physisorption of the molecules onto the nanostructures.

45. The method of embodiment 44, wherein the molecules originate from a source selected from a group consisting of: an exhalation, a gas, and a liquid.

46. The method of embodiment 45, wherein the exhalation originates from a source selected from a group consisting of: human breath, non-human animal breath, bacterial outgas, and plant outgas.

47. The method of embodiment 39, wherein the molecules are dipole containing organic species.

48. The method of embodiment 39, wherein the molecules are selected from a group of dipole containing organic species consisting of: alcohols, amines, amides, carboxylic acids, esters, furans, pyridines, aldehydes, ketones, sulfoxides, carbohydrates, and similar or equivalent dipole containing species.

49. The method of embodiment 39, wherein the molecules are selected from a group of molecules consisting of: methanol, ethanol, toluene, trichoromethane, n-butanol, 1-propanol, 1-octanol, tetrahydrofuran, pyridine, acetone, N,N-dimethyacetamide, N,N-dimethyformamide, dimethyl sulfoxide, glucose, and their combinations.

50. The method of embodiment 39, wherein the molecules are substantially polar.

51. The method of embodiment 38, wherein the molecule noninteraction zone sealant is permeated by a sealant selected from the group of sealants consisting of: epoxy and poly (vinyl chloride-co-vinyl-co-2-hydroxypropyl acrylate) (PVC) polymer.

52. A nanoconverter array, comprising: an array of one or more nanoconverters constructed according to the method of embodiment 38; wherein the nanoconverters are arranged to generate a specified current output and voltage output when supplied with a molecule.

53. The array of embodiment 52, wherein the nanoconverter operates as a nanosensor to detect the molecules by generation of the voltage output.

54. The array of embodiment 52, further comprising: a membrane permeable to the molecule that surrounds the molecule interaction zone; wherein the membrane preferentially allows transmission of a specific molecule.

55. The array of embodiment 52, wherein the nanostructure generated specified current output and voltage output is output to one or more of the group of devices consisting of: a cell phone, a smart phone, a glucose monitor, a pacemaker, a therapeutic or diagnostic device, a drug delivery device, an insulin pump, a left ventricular assist device, a cardioverter defibrillator, an artificial muscle device, a cochlear implant, a batteryless device, a powered nanomachine, and an artificial vision device.

56. The array of embodiment 52, wherein the nanostructure generated specified current output and voltage output is output to an insulin control system, the insulin control system comprising: a nanosensor glucose monitor that produces a sensor voltage proportional to a glucose molecule concentration; a controller that senses the sensor voltage; and an insulin pump controlled by the controller whereby insulin is disseminated when the sensor voltage exceeds a preset level.

57. A nanoconverter, comprising: a nanostructure; and means for generating power from the nanostructure.

58. The nanoconverter of embodiment 57, wherein the means for generating power from the nanostructure comprises: a molecular interaction zone of the nanostructure that interacts with molecules to generate power.

59. A nanoconverter, comprising: a nanostructure comprising a molecule interaction zone that interacts with molecules in the molecule interaction zone to generate power through physisorption.

60. A device powered by the nanoconverter of embodiment 59, wherein the device has no other power source.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for.

TABLE 1

| Solvent | Chemical formula | Heat of vaporization (kJ/mol) | Dipole moment (D) | Surface tension (mN/m) | Generated voltage (mV) |
|---|---|---|---|---|---|
| Benzene | $C_6H_6$ | 33.83 | 0 | 28.22 | ~0 |
| Hexane | $C_6H_{14}$ | 31.56 | 0 | 17.89 | ~0 |
| Toluene | $C_7H_8$ | 38.01 | 0.38 | 27.73 | 17 |
| 1,4 Dioxane | $C_4H_8O_2$ | 38.60 | 0.45 | 32.75 | ~0 |
| Trichloromethane | $CHCl_3$ | 31.28 | 1.04 | 26.67 | 35 |
| n-Butanol | $C_4H_{10}O$ | 52.35 | 1.66 | 24.93 | 40 |
| 1-Propanol | $C_3H_8O$ | 47.45 | 1.58 | 23.32 | 102 |
| Ethanol | $C_2H_6O$ | 42.32 | 1.69 | 21.97 | 133 |
| Methanol | $CH_4O$ | 37.43 | 1.70 | 22.07 | 130 |
| 1-Octanol | $C_6H_{18}O$ | 70.98 | 1.76 | 27.10 | 36 |
| Tetrahydrofuran | $C_4H_8O$ | 31.99 | 1.75 | 26.40 | 75 |
| Water | $H_2O$ | 43.98 | 1.85 | 71.99 | ~0 |
| Pyridine | $C_5H_5N$ | 40.21 | 2.22 | 36.56 | −80 |
| Acetone | $C_3H_6O$ | 30.99 | 2.88 | 22.72 | 245 |
| N,N-Dimethyl-acetamide | $C_4H_9NO$ | 50.24 | 3.70 | 34 | 60 |
| N,N-Dimethyl-formamide | $C_3H_7NO$ | 46.89 | 3.82 | 35.74 | 79 |
| Dimethyl sulfoxide | $C_2H_6OS$ | 37.86 | 3.96 | 42.92 | 65 |

What is claimed is:

1. A nanoconverter array, comprising:
   (i) a nanoconverter, comprising:
      (a) a nanostructure with first and second ends;
      (b) an electrode electrically connected to the nanostructure proximal to a molecule interaction zone at the first end of the nanostructure;
      (c) a sealant matrix that surrounds at least a portion of the nanostructure, wherein the surrounded portion of the nanostructure forms a molecule noninteraction zone; and
      (d) an electrode electrically connected to the nanostructure proximal to the molecule noninteraction zone at the second end of the nanostructure;
      (e) wherein the nanostructure generates a voltage and a current when the molecule interaction zone interacts with a molecule; and
   (ii) an array of one or more said nanoconverters;
   (iii) wherein the nanoconverters are arranged to generate a specified current output and voltage output when supplied with the molecule.

2. The array of claim 1, wherein the molecule is a dipole containing organic species.

3. The array of claim 1, wherein the molecule is selected from a group of dipole containing organic species consisting of: alcohols, amines, amides, carboxylic acids, esters, furans, pyridines, aldehydes, ketones, sulfoxides, carbohydrates, and similar and/or equivalent dipole containing species.

4. The array of claim 1, wherein the molecule is selected from a group of molecules consisting of: methanol, ethanol, toluene, trichoromethane, n-butanol, 1-propanol, 1-octanol, tetrahydrofuran, pyridine, acetone, N,N-dimethyacetamide, N,N-dimethyformamide, dimethyl sulfoxide, glucose, and their combinations.

5. The array of claim 1, wherein the molecule is substantially polar.

6. The array of claim 1, wherein the nanoconverter operates as a nanosensor to detect molecules by generation of the voltage output.

7. The array of claim 6, further comprising:
   a permeable membrane to the molecule that surrounds the molecule interaction zone;
   wherein the permeable membrane preferentially allows transmission of a specific molecule.

\* \* \* \* \*